(12) United States Patent
Yang et al.

(10) Patent No.: US 10,648,038 B2
(45) Date of Patent: May 12, 2020

(54) BIOMARKERS TO IDENTIFY PATIENTS THAT WILL RESPOND TO TREATMENT AND TREATING SUCH PATIENTS

(71) Applicant: Acetylon Pharmaceuticals, Inc., Boston, MA (US)

(72) Inventors: Min Yang, Newton, MA (US); Simon Steward Jones, Harvard, MA (US)

(73) Assignee: Acetylon Pharmaceuticals, Inc., Boston, MA (US)

( * ) Notice: Subject to any disclaimer, the term of this patent is extended or adjusted under 35 U.S.C. 154(b) by 81 days.

(21) Appl. No.: 15/497,397

(22) Filed: Apr. 26, 2017

(65) Prior Publication Data

US 2017/0327895 A1 Nov. 16, 2017

Related U.S. Application Data

(62) Division of application No. 13/866,367, filed on Apr. 19, 2013, now Pat. No. 9,663,825.

(60) Provisional application No. 61/778,260, filed on Mar. 12, 2013, provisional application No. 61/664,471, filed on Jun. 26, 2012, provisional application No. 61/635,336, filed on Apr. 19, 2012.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57415* (2013.01); *C12Q 2600/106* (2013.01); *C12Q 2600/156* (2013.01); *C12Q 2600/158* (2013.01); *G01N 2333/71* (2013.01)

(58) Field of Classification Search
CPC .................................................. C12Q 1/6886
USPC ........................................................ 435/7.1
See application file for complete search history.

(56) References Cited

U.S. PATENT DOCUMENTS

| | | | |
|---|---|---|---|
| 8,148,526 B1 | 4/2012 | Van Duzer et al. |
| 8,394,810 B2 | 3/2013 | Van Duzer et al. |
| 8,609,678 B2 | 12/2013 | Van Duzer et al. |
| 8,614,223 B2 | 12/2013 | Van Duzer et al. |
| 9,096,549 B2 | 8/2015 | van Duzer et al. |
| 9,139,583 B2 | 9/2015 | Van Duzer et al. |
| 9,145,412 B2 | 9/2015 | Van Duzer et al. |
| 9,278,963 B2 | 3/2016 | Van Duzer et al. |
| 9,403,779 B2 | 8/2016 | Tamang et al. |
| 9,409,890 B2 | 8/2016 | Van Duzer et al. |
| 9,421,212 B2 | 8/2016 | Van Duzer et al. |
| 9,464,073 B2 | 10/2016 | Mazitschek et al. |
| 9,562,013 B2 | 2/2017 | Van Duzer et al. |
| 2005/0123896 A1 | 6/2005 | Benz |
| 2008/0233562 A1 | 9/2008 | Sasakawa et al. |
| 2009/0023149 A1 | 1/2009 | Knudsen |
| 2011/0092447 A1 | 4/2011 | Hentsch et al. |
| 2012/0083504 A1 | 4/2012 | Van Duzer et al. |
| 2013/0225543 A1 | 8/2013 | Jones et al. |
| 2014/0011767 A1 | 1/2014 | Yang et al. |
| 2014/0142104 A1 | 5/2014 | Van Duzer et al. |
| 2014/0142117 A1 | 5/2014 | Van Duzer et al. |
| 2014/0243345 A1 | 8/2014 | Van Duzer et al. |
| 2014/0249148 A1 | 9/2014 | Van Duzer et al. |
| 2014/0357512 A1 | 12/2014 | Jones et al. |
| 2015/0045380 A1 | 2/2015 | Van Duzer et al. |
| 2015/0099744 A1 | 4/2015 | Yang et al. |
| 2015/0105358 A1 | 4/2015 | Quayle et al. |
| 2015/0105383 A1 | 4/2015 | Quayle et al. |
| 2015/0105384 A1 | 4/2015 | Jones et al. |
| 2015/0105409 A1 | 4/2015 | Quayle et al. |
| 2015/0150871 A1 | 6/2015 | Quayle et al. |
| 2015/0176076 A1 | 6/2015 | Yang et al. |
| 2016/0030458 A1 | 2/2016 | Jones et al. |
| 2016/0137630 A1 | 5/2016 | Shearstone et al. |
| 2016/0158231 A1 | 6/2016 | Jarpe et al. |
| 2016/0168093 A1 | 6/2016 | Van Duzer et al. |
| 2016/0228434 A1 | 8/2016 | Reilly et al. |
| 2016/0279128 A1 | 9/2016 | Van Duzer et al. |
| 2016/0339022 A1 | 11/2016 | Tamang et al. |
| 2016/0346279 A1 | 12/2016 | Kavelaars et al. |
| 2016/0355486 A1 | 12/2016 | Seyedi et al. |
| 2016/0375021 A1 | 12/2016 | Van Duzer et al. |
| 2017/0001965 A1 | 1/2017 | Van Duzer et al. |
| 2017/0020872 A1 | 1/2017 | Tamang et al. |

(Continued)

FOREIGN PATENT DOCUMENTS

| | | |
|---|---|---|
| JP | 2010-503637 | 3/2008 |
| JP | 2009-509910 A | 3/2009 |

(Continued)

OTHER PUBLICATIONS

Cao et al (Cancer Biology and Therapy, 2004, 3(11): 1081-1089).*
Sato et al (BJU Int, 2012, 109(8): 1258-1268).*
Pitts et al (Mol Cancer Ther, 2009, 8(2): 342-349).*
Atadja et al. (2009) "Development of the pan-DAC inhibitor panobinostat (LBH589): Successes and challenges," Cancer Letters. 280:233-241.
Huang et al. (2011) "HDAC inhibitor SNDX-275 enhances efficacy of trastuzumab in erbB2-overexpressing breast cancer cells and exhibits potential to overcome trastuzumab resistance," Cancer Letters. 307(1):72-79.
Koeppen et al. (2001) "Overexpression of HER2/neu in solid tumours: an immunohistochemical survey," Histopathology. 38:96-104.

(Continued)

*Primary Examiner* — Sean E Aeder
(74) *Attorney, Agent, or Firm* — Lathrop GPM LLP; Brian C. Trinque

(57) ABSTRACT

The invention relates to methods for using biomarkers to identify cancer patients that will or are likely to respond to treatment. Specifically, the invention relates to the use of one or more of three association studies of cancer types, gene mutations, or gene expression levels in order to identify cancer patients that will or are likely to respond to treatment with a histone deacetylase (HDAC) inhibitor, alone or in combination with another cancer treatment. The methods may, optionally, further include treating such patient with an HDAC inhibitor, alone or in combination with another cancer treatment.

7 Claims, 6 Drawing Sheets

(56) References Cited

U.S. PATENT DOCUMENTS

| | | |
|---|---|---|
| 2017/0044144 A1 | 2/2017 | Van Duzer et al. |
| 2017/0096403 A1 | 4/2017 | Van Duzer et al. |
| 2017/0096413 A1 | 4/2017 | Mazitschek et al. |

FOREIGN PATENT DOCUMENTS

| | | |
|---|---|---|
| JP | 2009-523011 A | 6/2009 |
| WO | 2004/074478 A1 | 9/2004 |
| WO | 2006/102557 A2 | 9/2006 |
| WO | 2007/067476 A2 | 6/2007 |
| WO | 2007/072225 A2 | 6/2007 |
| WO | 2008/095050 A1 | 8/2008 |
| WO | 2011/091213 A2 | 7/2011 |
| WO | 2013/158984 A1 | 10/2013 |

OTHER PUBLICATIONS

La Bonte et al. (2011) "The Dual EGFR/HER2 Inhibitor Lapatinib Synergistically Enhances the Antitumor Activity of the Histone Deacetylase Inhibitor Panobinostat in Colorectal Cancer Models," Cancer Res. 71(10):3635-3648.

Lai et al. (2010) "CUDC-101, a multitargeted inhibitor of histone deacetylase, epidermal growth factor receptor, and human epidermal growth factor receptor 2, exerts potent anticancer activity," Cancer Research. 70(9):3647-3656.

Lee et al. (2008) "The cytoplasmic deacetylase HDAC6 is required for efficient oncogenic tumorigenesis," Cancer Res. 68(18):7561-7569.

Stimson et al. (2009) "Biomarkers for predicting clinical responses to HDAC inhibitors," Cancer Letters. 280 (2):177-183.

Wang et al. (2010) "Increasing CD44+/CD24− tumor stem cells, and upregulation of COX-2 and HDAC6, as major functions of HER2 in breast tumorigenesis," Molecular Cancer 9:288. pp. 1-15.

Zilli et al. (2009) "Molecular mechanisms of endocrine resistance and their implication in the therapy of breast ancer," Biochimica et Biophysics Acta. 1795(1):62-81.

Extended European Search Report with Written Opinion corresponding to European Patent Application No. 13778809.7, dated Nov. 19, 2015.

International Search Report and Written Opinion, PCT/US2013/037355, dated Aug. 8, 2013, 7 pages.

Mishra et al. (2001) "Dynamic chromatin remodeling on the HER2 promoter in human breast cancer cells," FEBS Lett. 507:88-94.

U.S. Appl. No. 15/389,838, filed Dec. 23, 2016, John H. van Duzer.

Buggy et al., "CRA-024781: a novel synthetic inhibitor of histone deacetylase enzymes with antitumor activity in vitro and in vivo", Molecular Cancer Therapeutics, May 2006, vol. 5, No. 5, pp. 1309-1317.

Santo et al., "Preclinical activity, pharmacodynamic, and pharmacokinetic properties of a selective HDAC6 inhibitor, ACY-1215, in combination with bortezomib in multiple myeloma", Blood, Lymphoid Neoplasia, Mar. 15, 2012, vol. 119, No. 11, pp. 2579-2589.

Scott et al., "Destabilization of ERBB2 Transcripts by Targeting 3' Untranslated Region Messenger RNA Associated HuR and Histone Deacetylase-6", Mol Cancer Res, Jul. 2008, vol. 6, No. 7, pp. 1250-1258.

* cited by examiner # BIOMARKERS TO IDENTIFY PATIENTS THAT WILL RESPOND TO TREATMENT AND TREATING SUCH PATIENTS

CROSS REFERENCE TO RELATED APPLICATIONS

This application is a divisional of U.S. application Ser. No. 13/866,367, filed Apr. 19, 2013, which claims the benefit of U.S. Provisional Application No. 61/778,260, filed Mar. 12, 2013; U.S. Provisional Application No. 61/664,471, filed Jun. 26, 2012; and U.S. Provisional Application No. 61/635,336, filed Apr. 19, 2012. The contents of each of these applications are incorporated herein by reference in their entireties.

FIELD OF THE INVENTION

Provided herein are methods for using biomarkers to identify cancer patients who will or are likely to respond to treatment. Specifically, the methods relate to the use of one or more of three association studies of cancer types, gene mutations, or gene expression levels in order to identify cancer patients who will or are likely to respond to treatment with a histone deacetylase (HDAC) inhibitor, alone or in combination with another cancer treatment. The methods can, optionally, further include treating such patients with an HDAC inhibitor, alone or in combination with another cancer treatment. Additional methods and uses for these biomarkers and association studies are also disclosed.

BACKGROUND OF THE INVENTION

Cancer is one of the leading causes of death in the United States and in the world. It is estimated that approximately 1.6 million new cases of cancer will occur in the United States in 2012. It is also estimated that approximately 575,000 people will die from cancer in the United States in 2012.

Cancer grows out of normal cells in the body. Normal cells multiply when the body needs them, and die when the body doesn't need them. Cancer occurs when the cells in the body grow and multiply out of control. There are many different types of cancer, which can develop in almost any organ or tissue in the body.

There are many causes of cancer, such as exposure to carcinogenic chemicals, use of tobacco, drinking excess alcohol, exposure to environmental toxins, exposure to excessive sunlight, genetic problems, obesity, radiation, and viruses. In addition, the cause of many cancers remains unknown.

The symptoms of cancer depend on the type and location of the cancer.

Most cancers are diagnosed by biopsy. Depending on the location of the tumor, the biopsy may be a simple procedure or a serious operation.

Treatment varies based on the type of cancer, its stage of progression, and whether it has spread to other parts of the body. Treatment options include surgery to remove the cancer, radiation therapy (the use of high-powered x-rays, particles, or radioactive seeds to kill the cancer cells), chemotherapy (the use of drugs to kill the cancer cells), or a combination of the above.

Cancer therapy has many side effects. For example, radiation therapy is most harmful to rapidly growing cells, such as cancer cells, and specifically damages the DNA of cancer cells. However, radiation therapy also affects normal cells. People that receive radiation therapy often have hair loss; skin pain; red, burning skin; shedding of the outer layer of the skin; increased skin coloring; thinning of skin tissue; itching; fatigue and malaise; low blood counts; difficulty or painful swallowing; edema; changes in taste; loss of appetite; nausea; vomiting; and increased susceptibility to infection. Similar to radiation therapy, chemotherapy affects cells that divide often, such as cancer cells. However, chemotherapy also affects normal cells, such as those found in the blood, hair, and lining of the gastrointestinal tract. People that receive chemotherapy are more likely to have infections; become tired more easily; bleed too much; feel pain from damage to the nerves; have a dry mouth, mouth sores, or swelling of the mouth; have a poor appetite and lose weight; and have upset stomach, vomiting, and diarrhea.

Accordingly, there is a need to quickly and reliably choose a course of cancer treatment that will achieve the best outcome for the person receiving treatment while exposing the person to the least amount of chemotherapy drugs as possible, which will keep side effects to a minimum.

SUMMARY OF THE INVENTION

To meet this and other needs, provided herein are methods for using biomarkers to identify cancer patients who will or are likely to respond to treatment. Specifically, the methods relate to the use of one or more of three association studies of cancer types, gene mutations, or gene expression levels in order to identify cancer patients who will or are likely to respond to treatment with a histone deacetylase (HDAC) inhibitor, alone or in combination with another cancer treatment, therapy or drug.

An embodiment of the invention comprises an association study of cancer types, which associates treatment effect by tumor type.

Another embodiment of the invention comprises an association study of gene mutations, which associates gene mutation analysis with treatment type and tumor type.

A further embodiment of the invention comprises an association study of gene expression levels, which associates gene expression analysis with tumor type.

An embodiment of the invention provides a method for using a biomarker to identify a cancer patient who will or is likely to respond to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to predict whether a cancer patient will or is likely to respond to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to predict the response of a cancer patient to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to predict cancer cell inhibition in response to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to predict tumor cell killing in response to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to predict the sensitivity of cancer cell growth to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to predict the sensitivity of tumor cell growth to treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for using a biomarker to identify a cancer patient who is likely to benefit from treatment with a histone deacetylase (HDAC) inhibitor, alone or in combination with another cancer treatment, by interpreting data from one or more of the above three association studies of cancer types, gene mutations, or gene expression levels.

An embodiment of the invention provides a method for treating cancer comprising administering a histone deacetylase (HDAC) inhibitor, alone or in combination with another cancer treatment, to a patient who, according to data from one or more of the above three association studies of cancer types, gene mutations, or gene expression levels, will or is likely to respond to such treatment.

An embodiment of the invention provides a method for treating cancer in a patient comprising the steps of predicting whether a cancer patient will respond to treatment with a histone deacetylase (HDAC) inhibitor, alone or in combination with another cancer treatment, by interpreting data from one or more of the above three association studies of cancer types, gene mutations, or gene expression levels, and administering to the patient a therapeutically effective amount of a histone deacetylase (HDAC) inhibitor, alone or in combination with another cancer treatment, if it is determined that the patient will or likely to respond to such treatment.

An embodiment of the invention provides a method for re-treating cancer in a patient comprising the steps of predicting whether a cancer patient will respond to treatment with a histone deacetylase (HDAC) inhibitor, alone or in combination with another cancer treatment, by interpreting data from one or more of the above three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

An embodiment of the invention provides a method for modifying cancer treatment in a patient comprising the steps of predicting whether a cancer patient will respond to treatment with a histone deacetylase (HDAC) inhibitor, alone or in combination with another cancer treatment, by interpreting data from one or more of the above three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

An embodiment of the invention provides a method for optimizing cancer treatment in a patient comprising the steps of predicting whether a cancer patient will respond to treatment with a histone deacetylase (HDAC) inhibitor, alone or in combination with another cancer treatment, by interpreting data from one or more of the above three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

In a specific embodiment of the invention, the invention provides a method for predicting whether a breast cancer patient will respond to treatment with a histone deacetylase (HDAC) inhibitor comprising the steps of: a) determining whether the human epidermal growth factor receptor 2 (Her2) protein is overexpressed, as compared to a normalized protein expression level of the protein, in a biological sample from the breast cancer patient; and b) correlating the presence of such overexpression as an indication that the patient will respond to such treatment, or correlating the absence of such overexpression as an indication that the patient will not respond to such treatment.

In another specific embodiment of the invention, the invention provides a method for predicting whether a colorectal cancer patient will respond to combination treatment with a histone deacetylase (HDAC) inhibitor and a proteasome inhibitor comprising the steps of: a) determining whether a gene mutation in the SMAD family member 4 (SMAD4) gene is present in a biological sample from the colorectal cancer patient; and b) correlating the presence of a gene mutation as an indication that the patient will respond to such treatment, or correlating the absence of a gene mutation as an indication that the patient will not respond to such treatment.

In yet another specific embodiment of the invention, the invention provides a method for predicting whether a cancer patient will respond to combination treatment with a histone deacetylase (HDAC) inhibitor and a proteasome inhibitor comprising the steps of: a) determining whether a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL), is present in a biological sample from the cancer patient; and b) correlating the presence of one or more such mutations as an indication that the patient will respond to such treatment, or correlating the absence of such mutations as an indication that the patient will not respond to such treatment.

In another specific embodiment of the invention, the invention provides a method for predicting whether a cancer patient will respond to treatment with a histone deacetylase (HDAC) inhibitor comprising the steps of: a) measuring the expression level of a gene selected from the group consisting of pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); and abhydrolase domain containing 14A (ABHD14A) in a biological sample from the cancer patient; and b) correlating a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4 as an indication that the patient will respond to such treatment; or correlating a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A as an indication that the patient will respond to such treatment.

In yet another specific embodiment of the invention, the invention provides a method for predicting whether a cancer patient will respond to combination treatment with a histone deacetylase (HDAC) inhibitor and a proteasome inhibitor comprising the steps of: a) measuring the expression level of a gene selected from the group consisting of UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); in a biological sample from the cancer patient; and b) correlating a low expression level, as compared to a normalized gene expression level of the gene, of any one or more of the genes UGDH, H2AFY2, MYO5C, NPNT, and KIAA1598 as an indication that the patient will respond to such treatment; or correlating a high expression level, as compared to a normalized gene expression level of the gene, of any one or more of the genes SRGN, COL6A3, GPSM3, HSD11B1, PEX6, RAC2, SSX5, and ACBD3 as an indication that the patient will respond to such treatment.

In a further specific embodiment of the invention, the invention provides a method for predicting whether a cancer patient will respond to treatment with a histone deacetylase (HDAC) inhibitor, alone or in combination with a proteasome inhibitor, comprising the steps of: a) evaluating the data from one or more association studies comprising: 1) an association study that associates treatment effect by tumor type, wherein brain/neuron cancer, breast cancer, lymphoid cancer, kidney cancer, colon/large intestine cancer, and skin cancer are determined to be sensitive to combination treatment with a histone deacetylase inhibitor and a proteasome inhibitor, 2) an association study that associates gene mutation analysis with treatment type and tumor type, wherein i) the overexpression of the human epidermal growth factor receptor 2 (Her2) protein, as compared to a normalized protein expression level of the protein, in a biological sample from a breast cancer patient is an indication that the patient will respond to treatment with a histone deacetylase inhibitor, ii) the presence of a gene mutation in the SMAD family member 4 (SMAD4) gene in a biological sample from a colorectal cancer patient is an indication that the patient will respond to combination treatment with a histone deacetylase inhibitor and a proteasome inhibitor, or iii) the presence of one or more gene mutations in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL) in a biological sample from a cancer patient is an indication that the patient will respond to combination treatment with a histone deacetylase inhibitor and a proteasome inhibitor, or 3) an association study that associates gene expression analysis with treatment type, comprising i) measuring the expression level of a gene selected from the group consisting of pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); and abhydrolase domain containing 14A (ABHD14A) in a biological sample from the cancer patient; and a) correlating a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4 as an indication that the patient will respond to treatment with a histone deacetylase inhibitor; or correlating a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A as an indication that the patient will respond to treatment with a histone deacetylase inhibitor, or ii) measuring the expression level of a gene selected from the group consisting of UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); in a biological sample from the cancer patient; and a) correlating a low expression level, as compared to a normalized gene expression level of the gene, of any one or more of the genes UGDH, H2AFY2, MYO5C, NPNT, and KIAA1598 as an indication that the patient will respond to combination treatment with a histone deacetylase inhibitor and a proteasome inhibitor; or correlating a high expression level, as compared to a normalized gene expression level of the gene, of any one or more of the genes SRGN, COL6A3, GPSM3, HSD11B1, PEX6, RAC2, SSX5, and ACBD3 as an indication that the patient will respond to combination treatment with a histone deacetylase inhibitor and a proteasome inhibitor, and b) evaluating the data regarding cancer types, gene mutations, or gene expression levels to determine whether the patient will respond to such treatment.

In preferred specific embodiments of the invention, the cancer is selected from the group consisting of: brain/neuronal cancer, breast cancer, cancer of the central nervous system, haematopoietic and lymphoid tissue cancer, kidney cancer, cancer of the large intestine, liver cancer, lung cancer, cancer of the oesophagus, pancreatic cancer, prostate cancer, skin cancer, soft tissue cancer, and stomach cancer.

In preferred specific embodiments of the invention, the HDAC inhibitor is a HDAC6 inhibitor. In more preferred specific embodiments of the invention, the HDAC6 inhibitor is a compound of formula I:

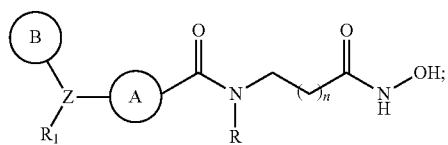

(I)

or a pharmaceutically acceptable salt, ester or prodrug thereof. In most preferred specific embodiments of the invention, the compound of formula I is

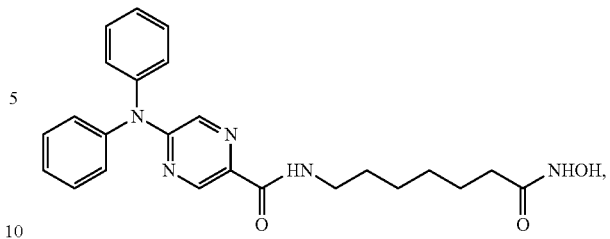

which is referred to herein as Compound A.

In preferred specific embodiments of the invention, the proteasome inhibitor is bortezomib.

In preferred specific embodiments of the invention, the biological sample is a biopsy sample.

In preferred specific embodiments of the invention, the methods further comprise the step of administering to the patient a therapeutically effective amount of a HDAC inhibitor. In alternative preferred specific embodiments of the invention, the methods further comprise the step of administering to the patient a therapeutically effective amount of a HDAC inhibitor and a proteasome inhibitor.

A preferred embodiment of the invention provides a kit comprising a nucleic acid that hybridizes under stringent conditions with any one of the genes selected from the group consisting of erythroblastic leukemia viral oncogene homolog 2 (ERBB2); SMAD family member 4 (SMAD4); phosphatase and tensin homolog (PTEN); epidermal growth factor receptor oncogene (EGFR); histone-lysine N-methyltransferase (EZH2); SET domain containing 2 (SETD2); von Hippel-Lindau tumor suppressor (VHL); pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexyzme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); abhydrolase domain containing 14A (ABHD14A); UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3);

G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); and instructions for use of the nucleic acid to detect the presence of the gene or the expression level of the gene.

Another preferred embodiment of the invention provides a kit comprising an antibody that binds to a protein produced by any one of the genes selected from the group consisting of erythroblastic leukemia viral oncogene homolog 2 (ERBB2); SMAD family member 4 (SMAD4); phosphatase and tensin homolog (PTEN); epidermal growth factor receptor oncogene (EGFR); histone-lysine N-methyltransferase (EZH2); SET domain containing 2 (SETD2); von Hippel-Lindau tumor suppressor (VHL); pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); abhydrolase domain containing 14A (ABHD14A); UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); and instructions for use of the antibody to detect the presence of the gene or the expression level of the gene.

Another preferred embodiment of the invention provides a method for predicting whether a breast cancer patient will respond to treatment with a histone deacetylase (HDAC) inhibitor comprising the steps of:
 a) measuring the expression level of each of the following genes: transforming growth factor beta-3 (TGFB3); CD44 molecule (Indian blood group) (CD44); cytochrome p450, family 4, subfamily Z, polypeptide 2 pseudogene (CYP4Z2P); interferon-induced protein 44 (IFI44); solute carrier family 9, subfamily A (NHE6, cation proton antiporter 6), member 6 (SLC9A6); v-erb-b2 erythroblastic leukemia viral oncogene homolog 2, neuro/glioblastoma derived oncogene homolog (avian) (ERBB2); v-yes-1 Yamaguchi sarcoma viral related oncogene homolog (LYN); pleckstrin homology-like domain, family A, member 1 (PHLDA1); peroxisome proliferator-activated receptor gamma (PPARG); dicarbonyl/L-xylulose reductase (DCXR); uridine phosphorylase 1 (UPP1); ATP-binding cassette, subfamily C (CFTR/MRP), member 11 (ABCC11); aldo-keto reductase family 1, member C2 (dihydrodiol dehydrogenase 2; bile acid binding protein; 3-alpha hydroxysteroid dehydrogenase, type III) (AKR1C2); BCL2-associated athanogene 2 (BAG2); TLR4 interactor with leucine-rich repeats (TRIL); uncharacterized LOC440335 (LOC440335); inhibin, beta B (INHBB); dickkopf 1 homolog (*Xenopus laevis*) (DKK1); insulin receptor substrate 2 (IRS2); chromosome 17 open reading frame 28 (C17orf28); LIM domain kinase 2 (LIMK2); like-glycosyltransferase (LARGE); coiled-coil domain containing 82 (CCDC82); solute carrier family 40 (iron-regulated transporter), member 1 (SLC40A1); interferon-induced protein with tetratricopeptide repeats 1 (IFIT1); formin-like 2 (FMNL2); leukemia inhibitory factor (LIF); transforming growth factor, beta recetor 2 (70/80 kDa) (TGFBR2); G protein-coupled receptor 160 (GPR160); cytokine inducible SH2-containing protein (CISH); phospholipase C, beta 4 (PLCB4); B-cell linker (BLNK); phospholipase C, gamma 2 (phosphatidylinositol-specific) (PLCG2); caveolin 2 (CAV2); proline dehydrogenase (oxidase) 1 (PRODH); ras homolog family member B (RHOB); interferon-induced protein with tetratricopeptide repeats 3 (IFIT3); calbindin 2 (CALB2); TSPY-like 5 (TSPYL5); chromosome X open reading frame 61 (CXorf61); hematopoietically expressed homeobox (HHEX); cAMP responsive element binding protein 3-like4 (CREB3L4); X-box binding protein 1 (XBP1); SAM pointed domain containing ets trsanscription factor (SPDEF); nuclear receptor coactivator 7 (NCOA7); galanin prepropeptide (GAL); HECT and RLD domain containing E3 ubiquitin protein ligase 5 (HERC5); major histocompatibility complex, class I, A (HLA-A); centromere protein V (CENPV); frequently rearranged in advanced T-cell lymphomas 2 (FRAT2); phospholipase B domain containing 1 (PLBD1); adenosine A2b receptor (ADORA2B); G protein-coupled receptor, family C, group 5, member A (GPRC5A); enoyl CoA hydratase domain containing 1 (ECHDC1); guanylate binding protein 1, interferon-inducible (GBP1); sulfatase 2 (SULF2), uncharacterized LOC100507463 (LOC100507463), and KIAA1324 (KIAA1324) in a biological sample from the breast cancer patient; and
 b) correlating a high expression level, as compared to a normalized gene expression level of the gene, of the following genes TGFB3, CYP4Z2P, ERBB2, DCXR, ABCC11, TRIL, LOC440335, INHBB, C17orf28, LIMK2, LARGE, SLC40A1, GPR160, CISH, PLCB4, BLNK, PRODH, RHOB, CREB3L4, XBP1, SPDEF, FRAT2, and KIAA1324 as an indication that the patient will respond to such treatment; and correlating a low expression level, as compared to a normalized gene expression level of the gene, of the following genes CD44, 1E144, SLC9A6, LYN, PHLDA1, PPARG, UPP1, AKR1C2, BAG2, DKK1, IRS2, IFIT1, FMNL2, LIF, TGFBR2, PLCG2, CAV2, IFIT3, CALB2, TSPYL5, CXorf61, HHEX, NCOA7, GAL, HERC5, HLA-A, CENPV, PLBD1, ADORA2B, GPRC5A, ECHDC1, GBP1, SULF2, and LOC100507463 as an indication that the patient will respond to such treatment. In a further preferred embodiment of the invention, the method further comprises the step of administering to the patient a therapeutically effective amount of a HDAC inhibitor.

DETAILED DESCRIPTION OF THE INVENTION

Definitions

Figure 1:
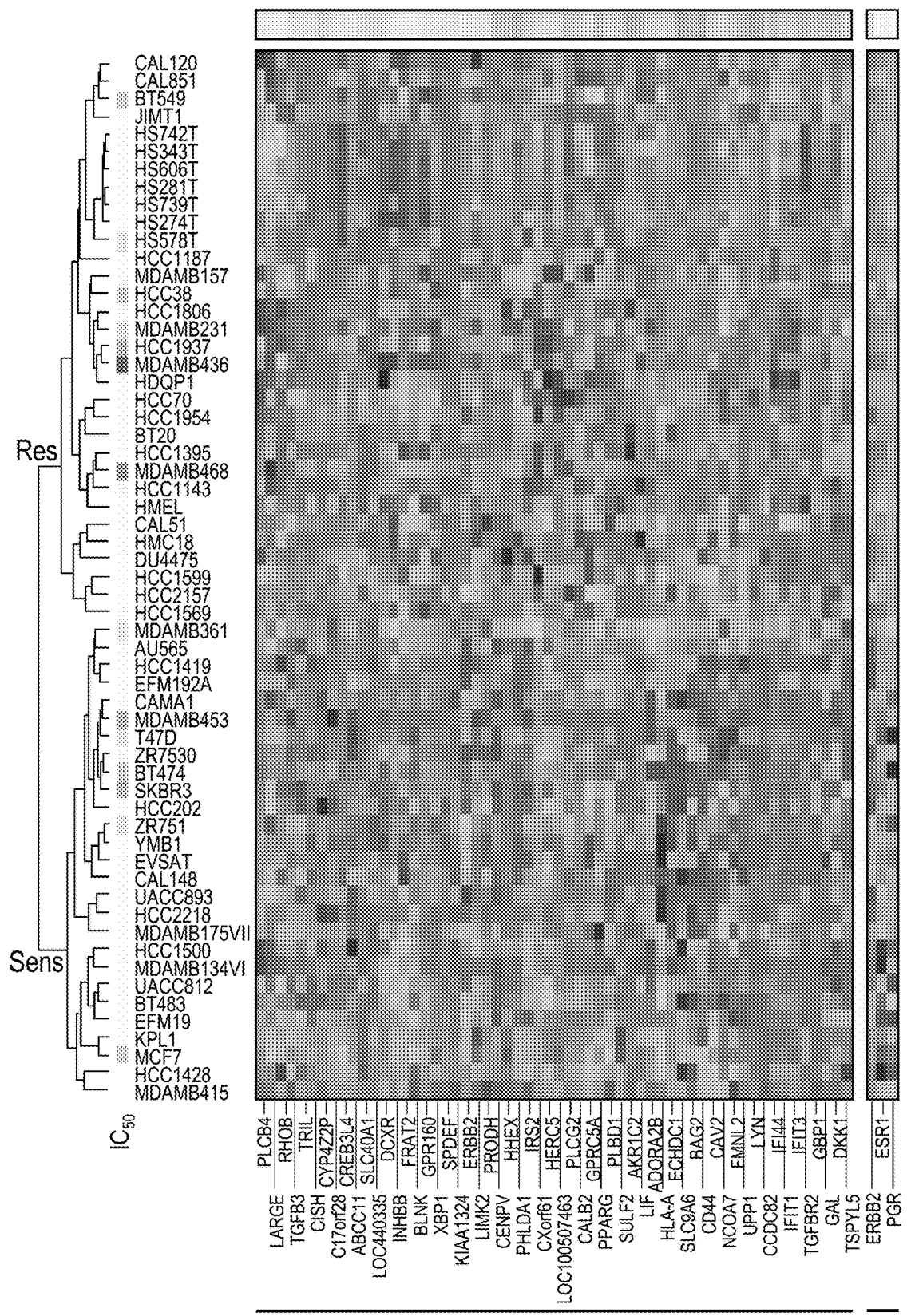
FIG. 1 is a picture of the 58 gene signature heatmap in 59 CCLE breast cancer cell lines.

Unless defined otherwise, all technical and scientific terms used herein have the same meaning as is commonly understood by one of ordinary skill in the art.

The articles "a" and "an" are used herein to refer to one or to more than one (i.e., to at least one) of the grammatical object of the article. By way of example, "a biomarker" means one biomarker or more than one biomarker.

The terms "administer" or "administration" refer to the act of injecting or otherwise physically delivering a substance as it exists outside the body (e.g., a formulation of the invention) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

An antibody that "binds" an antigen of interest is one capable of binding that antigen with sufficient affinity such that the antibody is useful in detecting the presence of the antigen.

The term "biological sample" shall generally mean any biological sample obtained from an individual, body fluid, cell line, tissue culture, or other source. Body fluids are, for example, blood, lymph, sera, plasma, urine, semen, synovial fluid, and spinal fluid. Methods for obtaining tissue biopsies and body fluids from mammals are well known in the art. If the term "sample" is used alone, it shall still mean that the "sample" is a "biological sample", i.e., the terms are used interchangeably.

The terms "composition" and "formulation" are intended to encompass a product containing the specified ingredients (e.g., an HDAC inhibitor) in, optionally, the specified amounts, as well as any product which results, directly or indirectly, from the combination of the specified ingredients in, optionally, the specified amounts.

The term "excipients" refers to inert substances that are commonly used as a diluent, vehicle, preservative, binder, stabilizing agent, etc. for drugs and includes, but is not limited to, proteins (e.g., serum albumin, etc), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

The phrases "respond to treatment with a HDAC inhibitor" or "respond to treatment with a HDAC6 inhibitor" or similar phrases refer to the clinical benefit imparted to a patient suffering from a disease or condition, such as cancer, from or as a result of the treatment with the HDAC inhibitor (e.g., a HDAC6 inhibitor). A clinical benefit includes a complete remission, a partial remission, a stable disease (without progression), progression-free survival, disease free survival, improvement in the time-to-progression (of the disease), improvement in the time-to-death, or improvement in the overall survival time of the patient from or as a result of the treatment with the HDAC inhibitor. There are criteria for determining a response to therapy and those criteria allow comparisons of the efficacy to alternative treatments (Slapak and Kufe, Principles of Cancer Therapy, in Harrisons's Principles of Internal Medicine, 13th edition, eds. Isselbacher et al., McGraw-Hill, Inc., 1994). For example, a complete response or complete remission of cancer is the disappearance of all detectable malignant disease. A partial response or partial remission of cancer may be, for example, an approximately 50 percent decrease in the product of the greatest perpendicular diameters of one or more lesions or where there is not an increase in the size of any lesion or the appearance of new lesions.

The term "progression of cancer" includes and may refer to metastasis, a recurrence of cancer, or an at least approximately 25 percent increase in the product of the greatest perpendicular diameter of one lesion or the appearance of new lesions. The progression of cancer is "inhibited" if recurrence or metastasis of the cancer is reduced, slowed, delayed, or prevented.

"Nucleotides" are nucleosides that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide" or a "polynucleotide". Nucleotides are the units of deoxyribonucleic acid (DNA) and ribonucleic acid (RNA). As used herein, the term "polynucleotide" is synonymous with "nucleic acid".

The term "probe" refers to synthetically or biologically produced nucleic acids (DNA or RNA) which, by design or selection, contain specific nucleotide sequences that allow them to hybridize under defined predetermined stringencies specifically (i.e., preferentially) to "nucleic acids". A "probe" can be identified as a "capture probe" meaning that it "captures" the nucleic acid so that it can be separated from undesirable materials which might obscure its detection. Once separation is accomplished, detection of the captured "target nucleic acid" can be achieved using a suitable procedure. "Capture probes" are often already attached to a solid phase.

The term hybridization under "stringent conditions" is given the same meaning as in Sambrook et al. (Molecular Cloning, A Laboratory Manual, Cold Spring Harbor Laboratory Press (1989), paragraph 1.101-1.104). For example, a "stringent hybridization" is the case when a hybridization signal is still detectable after washing for 1 hour with 1×SSC and 0.1% SDS at 50° C., preferably at 55° C., more preferably at 62° C., and most preferably at 68° C., and more preferably for 1 hour with 0.2×SSC and 0.1% SDS at 50° C., preferably at 55° C., more preferably at 62° C., and most preferably at 68° C. The composition of the SSC buffer is described in Sambrook et al. (Molecular Cloning, A Laboratory Manual, Cold Spring Harbor Laboratory Press (1989)).

A "transcribed polynucleotide" is a polynucleotide (e.g., a RNA, a cDNA, or an analog of one of an RNA or cDNA) that is complementary to or homologous with all or a portion of a mature RNA made by transcription of a gene, such as the marker gene, and normal post-transcriptional processing (e.g., splicing), if any, of the transcript. The term "cDNA" is an abbreviation for complementary DNA, the single-stranded or double-stranded DNA copy of a mRNA. The term "mRNA" is an abbreviation for messenger RNA, the RNA that serves as a template for protein synthesis.

The terms "marker gene" or "biomarker gene" include a gene that is useful for identifying a cancer patient that will or is likely to respond to treatment with a HDAC inhibitor, alone or in combination with another cancer treatment.

The terms "marker polynucleotide" or "biomarker polynucleotide" include a nucleotide transcript (hnRNA or mRNA) encoded by a biomarker gene, or cDNA derived from the nucleotide transcript, or a segment of said transcript or cDNA.

The terms "marker protein", "marker polypeptide", "biomarker protein", or "biomarker polypeptide" include a protein or polypeptide encoded by a biomarker gene or a fragment thereof.

The terms "marker" and "biomarker" are used interchangeably and refer to a biomarker gene, biomarker polynucleotide, or biomarker protein, as defined above.

The term "gene product" refers to a biomarker polynucleotide, or biomarker protein encoded by a biomarker gene.

The expression of a biomarker gene differs from the level of expression of the biomarker gene in a reference sample or a normalized gene expression level if the level of expression of the biomarker gene in a sample from the patient differs from the level in a sample from the reference subject or a normalized gene expression level by an amount greater than the standard error of the assay employed to assess expression, and preferably at least 10%, and more preferably 25%, 50%, 75%, 100%, 125%, 150%, 175%, 200%, 300%, 400%, 500% or 1,000% of that amount. For example, expression of the biomarker gene in the patient can be considered "lower" than the level of expression in a control subject or a normalized gene expression level if the level of expression in a sample from the patient is lower than the level in a sample from the control subject or a normalized gene expression level by an amount greater than the standard error of the assay employed to assess expression, and preferably at least 10%, and more preferably 25%, 50%, 75%, 100%, 125%, 150%, 175%, 200%, 300%, 400%, 500% or 1,000% of that amount. Alternatively, expression of the biomarker gene in the patient can be considered "higher" than the level of expression in a control subject or a normalized gene expression level if the level of expression in a sample from the patient is higher than the level in a sample from the control subject or a normalized gene expression level by an amount greater than the standard error of the assay employed to assess expression, and preferably at least 10%, and more preferably 25%, 50%, 75%, 100%, 125%, 150%, 175%, 200%, 300%, 400%, 500% or 1,000% of that amount.

The terms "level of expression" or "expression level" are used interchangeably and generally refer to the amount of a polynucleotide or an amino acid product or protein in a biological sample. "Expression" generally refers to the process by which gene encoded information is converted into the structures present and operating in the cell. Therefore, the "expression" of a gene may refer to transcription into a polynucleotide, translation into a protein or even posttranslational modification of the protein. Fragments of the transcribed polynucleotide, the translated protein or the postranslationally modified protein shall also be regarded as expressed whether they originate from a transcript generated by alternative splicing, a degraded transcript, or from a posttranslational processing of the protein, e.g., by proteolysis. "Expressed genes" include those that are transcribed into a polynucleotide as mRNA and then translated into a protein; and also include expressed genes that are transcribed into RNA but not translated into a protein (for example, transfer and ribosomal RNAs).

The term "mutation" refers to a change or alteration in a gene or protein, such as an insertion, deletion, substitution, or modification of one or more nucleic acids or amino acids in the gene or protein, respectively. For example, the mutation may be a single point mutation, multiple point mutations, a frame-shift mutation, deletion, insertion, inversion, or DNA expression mutation.

The terms "overexpression", "increased expression" or "high expression" refer to an upward deviation in levels of expression, as compared to the baseline expression level in a sample used as a control or a normalized gene expression level or normalized protein expression level.

The terms "underexpression", "decreased expression" or "low expression" refer to a downward deviation in levels of expression, as compared to the baseline expression level in a sample used as a control or a normalized gene expression level or normalized protein expression level.

The phrase "normalized gene expression level" refers to an average gene expression level between individual cell lines.

The phrase "normalized protein expression level" refers to an average protein expression level between individual cell lines.

A "kit" is any manufacture (e.g., a package or container) comprising at least one reagent, e.g., a probe, for specifically detecting a biomarker gene or protein. The manufacture is preferably promoted, distributed, or sold as a unit for performing the methods of the invention.

The term "therapy" refers to any protocol, method, and/or agent that can be used in the prevention, management, treatment, and/or amelioration of a disease.

The term "alkyl," as used herein, refers to saturated, straight- or branched-chain hydrocarbon moieties containing, in certain embodiments, between one and six, or one and eight carbon atoms, respectively. Examples of $C_1$-$C_6$ alkyl moieties include, but are not limited to, methyl, ethyl, propyl, isopropyl, n-butyl, tert-butyl, neopentyl, n-hexyl moieties; and examples of $C_1$-$C_8$ alkyl moieties include, but are not limited to, methyl, ethyl, propyl, isopropyl, n-butyl, tert-butyl, neopentyl, n-hexyl, heptyl, and octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl moiety.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," or "arylalkyl," as used herein, refers to an alkyl residue attached to an aryl ring. Examples include, but are not limited to, benzyl, phenethyl and the like.

The term "carbocyclic," as used herein, denotes a monovalent group derived from a monocyclic or polycyclic saturated, partially unsaturated, or fully unsaturated carbocyclic ring compound. Examples of carbocyclic groups include groups found in the cycloalkyl definition and aryl definition.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, moieties or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "hal," "halo" and "halogen," as used herein, refer to an atom selected from fluorine, chlorine, bromine and iodine.

The term "oxo" as used herein, refers to an oxygen that is attached to a carbon, preferably by a double bond (e.g., carbonyl).

As described herein, compounds used in the methods of the invention may optionally be substituted with one or more substituents, such as are illustrated generally in formula I, or as exemplified by particular classes, subclasses, and species of the invention. It will be appreciated that the phrase "optionally substituted" is used interchangeably with the phrase "substituted or unsubstituted". In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl,"

"optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

alkyl, alkenyl, alkynyl, cycloalkyl, aryl, heterocycloalkyl, heteroaryl, arylalkyl, heteroarylalkyl, —F, —Cl, —Br, —I, —OH, protected hydroxy, oxygen, oxo,

—$NO_2$, —CN,

—$NH_2$, protected amino, —NH—$C_1$-$C_{12}$-alkyl, —NH-aryl, -dialkylamino, —O—C1-C12-alkyl, —O-aryl,

—C(O)—, —C(O)O—, —C(O)NH—, —OC(O)—, —OC(O)O—, —OC(O)NH—, —NHC(O)—, —NHC(O)O—,

—C(O)— $C_1$-$C_{12}$-alkyl, —C(O)—$C_3$-$C_{12}$-cycloalkyl, —C(O)-aryl, —C(O)-heteroaryl, —C(O)— heterocycloalkyl, —C(O)O— $C_1$-$C_{12}$-alkyl, —C(O)O—$C_3$-$C_{12}$-cycloalkyl, —C(O)O-aryl, —C(O)O-heteroaryl, —C(O)O-heterocycloalkyl, —$CONH_2$, —CONH— $C_1$-$C_{12}$-alkyl, —CONH-aryl, —$OCO_2$— $C_1$-$C_{12}$-alkyl, —$OCO_2$-aryl, —$OCONH_2$, —OCONH— $C_1$-$C_{12}$-alkyl, —OCONH-aryl, —NHC(O)— $C_1$-$C_{12}$-alkyl, —NHC(O)-aryl, —$NHCO_2$— $C_1$-$C_{12}$-alkyl, —$NHCO_2$— aryl, —S(O)—$C_1$-$C_{12}$-alkyl, —S(O)-aryl, —$SO_2$NH—$C_1$-$C_{12}$-alkyl, —$SO_2$NH-aryl, —$NHSO_2$—$C_1$-$C_{12}$-alkyl, —$NHSO_2$-aryl, —SH, —S—$C_1$-$C_{12}$-alkyl, or —S-aryl.

In certain embodiments, the optionally substituted groups include the following: $C_1$-$C_{12}$-alkyl, $C_2$-$C_{12}$-alkenyl, $C_2$-$C_{12}$-alkynyl, $C_3$-$C_{12}$-cycloalkyl, $C_3$-$C_{12}$-aryl, $C_3$-$C_{12}$-heterocycloalkyl, $C_3$-$C_{12}$-heteroaryl, $C_4$-$C_{12}$-arylalkyl, or $C_2$-$C_{12}$-heteroarylalkyl.

It is understood that the aryls, heteroaryls, alkyls, and the like can be further substituted.

As used herein, the term "metal chelator" refers to any molecule or moiety that is capable of forming a complex (i.e., "chelates") with a metal ion. In certain exemplary embodiments, a metal chelator refers to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, $Ca^{2+}$, $Fe^{3+}$, $Zn^{2+}$, $Na^+$, etc. In certain embodiments, the metal chelator binds $Zn^{2+}$. In certain embodiments, molecules of moieties that precipitate metal ions are not considered to be metal chelators.

As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. In certain other preferred embodiments, natural-product-like small molecules are utilized.

The terms "subject" or "patient" as used herein refer to a mammal. A subject therefore refers to, for example, dogs, cats, horses, cows, pigs, guinea pigs, and the like. Preferably the subject is a human.

"Treat", "treating" and "treatment" refer to a method of alleviating or abating a disease and/or its attendant symptoms.

As used herein, the term "pharmaceutically acceptable salt" refers to those salts of the compounds formed by the process disclosed herein which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977).

As used herein, the term "pharmaceutically acceptable ester" refers to esters of the compounds formed by the process disclosed herein which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process disclosed herein which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae disclosed herein. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

Methods

The invention provides methods for using a biomarker to identify a cancer patient who will or is likely to respond to treatment. Specifically, the invention relates to the use of one or more of three association studies of cancer types, gene mutations, or gene expression levels in order to identify a cancer patient who will or is likely to respond to treatment with a histone deacetylase (HDAC) inhibitor, alone or in combination with another cancer treatment. The methods may, optionally, further include treating such patient with an HDAC inhibitor, alone or in combination with another cancer treatment.

An embodiment of the invention comprises an association study of cancer types, which associates treatment effect by tumor type.

Another embodiment of the invention comprises an association study of gene mutations, which associates gene mutation analysis with treatment type and tumor type.

A further embodiment of the invention comprises an association study of gene expression levels, which associates gene expression analysis with tumor type.

An embodiment of the invention provides a method for using a biomarker to identify a cancer patient who will or is likely to respond to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to predict whether a cancer patient will or is likely to respond to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to predict the response of a cancer patient to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to predict cancer cell inhibition in response to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to predict tumor cell killing in response to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to predict the sensitivity of cancer cell growth to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to predict the sensitivity of tumor cell growth to treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for using a biomarker to identify a cancer patient who is likely to benefit from treatment with a histone deacetylase (HDAC) inhibitor, alone or in combination with another cancer treatment, by interpreting data from one or more of the three association studies of cancer types, gene mutations, or gene expression levels.

An embodiment of the invention provides a method for treating cancer comprising administering a histone deacetylase (HDAC) inhibitor, alone or in combination with another cancer treatment, to a patient who, according to data from one or more of the three association studies of cancer types, gene mutations, or gene expression levels, will or is likely to respond to such treatment.

An embodiment of the invention provides a method for treating cancer in a patient comprising the steps of predicting whether a cancer patient will respond to treatment with a histone deacetylase (HDAC) inhibitor, alone or in combination with another cancer treatment, by interpreting data from one or more of the three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

An embodiment of the invention provides a method for re-treating cancer in a patient comprising the steps of predicting whether a cancer patient will respond to treatment with a histone deacetylase (HDAC) inhibitor, alone or in combination with another cancer treatment, by interpreting data from one or more of the three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

An embodiment of the invention provides a method for modifying cancer treatment in a patient comprising the steps of predicting whether a cancer patient will respond to treatment with a histone deacetylase (HDAC) inhibitor, alone or in combination with another cancer treatment, by interpreting data from one or more of the three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

An embodiment of the invention provides a method for optimizing cancer treatment in a patient comprising the steps of predicting whether a cancer patient will respond to treatment with a histone deacetylase (HDAC) inhibitor, alone or in combination with another cancer treatment, by interpreting data from one or more of the three association studies of cancer types, gene mutations, or gene expression levels, and administering to the patient a therapeutically effective amount of a histone deacetylase (HDAC) inhibitor, alone or in combination with another cancer treatment, if it is determined that the patient will or is likely to respond to such treatment.

An embodiment of the invention provides a method for treating breast cancer in a patient in need thereof comprising the steps of:

a) determining whether the human epidermal growth factor receptor 2 (Her2) protein is overexpressed, as compared to a normalized protein expression level of the protein, in a biological sample from the breast cancer patient;

b) correlating the presence of such overexpression as an indication that the patient will respond to such treatment, or correlating the absence of such overexpression as an indication that the patient will not respond to such treatment; and c) administering to a patient that will respond to treatment a therapeutically effective amount of a histone deacetylase (HDAC) inhibitor.

An embodiment of the invention provides a method for treating cancer in a patient in need thereof comprising the steps of:

a) measuring the expression level of a gene selected from the group consisting of pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (S. cerevisiae) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); and abhydrolase domain containing 14A (ABHD14A) in a biological sample from the cancer patient;

b) correlating a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4 as an indication that the patient will respond to such treatment; or correlating a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A as an indication that the patient will respond to such treatment; and c) administering to a patient that will respond to treatment a therapeutically effective amount of a histone deacetylase (HDAC) inhibitor.

An embodiment of the invention provides a method for treating colorectal cancer in a patient in need thereof comprising the steps of:

a) determining whether a gene mutation in the SMAD family member 4 (SMAD4) gene is present in a biological sample from the colorectal cancer patient;

b) correlating the presence of a gene mutation as an indication that the patient will respond to such treatment, or correlating the absence of a gene mutation as an indication that the patient will not respond to such treatment; and c) administering to a patient that will respond to treatment a therapeutically effective amount of a histone deacetylase (HDAC) inhibitor and a proteasome inhibitor.

An embodiment of the invention provides a method for treating cancer in a patient in need thereof comprising the steps of:

a) determining whether a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL), is present in a biological sample from the cancer patient;

b) correlating the presence of one or more such mutations as an indication that the patient will respond to such treatment, or correlating the absence of such mutations as an indication that the patient will not respond to such treatment; and c) administering to a patient that will respond to treatment a therapeutically effective amount of a histone deacetylase (HDAC) inhibitor and a proteasome inhibitor.

An embodiment of the invention provides a method for treating cancer in a patient in need thereof comprising the steps of:

a) measuring the expression level of a gene selected from the group consisting of UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); in a biological sample from the cancer patient;

b) correlating a low expression level, as compared to a normalized gene expression level of the gene, of any one or more of the genes UGDH, H2AFY2, MYO5C, NPNT, and KIAA1598 as an indication that the patient will respond to such treatment; or correlating a high expression level of the gene, as compared to a normalized gene expression level, of any one or more of the genes SRGN, COL6A3, GPSM3, HSD11B1, PEX6, RAC2, SSX5, and ACBD3 as an indication that the patient will respond to such treatment; and c) administering to a patient that will respond to treatment a therapeutically effective amount of a histone deacetylase (HDAC) inhibitor and a proteasome inhibitor.

An embodiment of the invention provides a method for treating cancer in a patient in need thereof comprising the steps of:

a) evaluating the data from one or more association studies comprising:

1) an association study that associates treatment effect by tumor type, wherein brain/neuron cancer, breast cancer, lymphoid cancer, kidney cancer, colon/large intestine cancer, and skin cancer are determined to be sensitive to combination treatment with a histone deacetylase inhibitor and a proteasome inhibitor, 2) an association study that associates gene mutation analysis with treatment type and tumor type, wherein
   i) the overexpression of the human epidermal growth factor receptor 2 (Her2) protein, as compared to a normalized protein expression level of the protein, in a biological sample from a breast cancer patient is an indication that the patient will respond to treatment with a histone deacetylase inhibitor,
   ii) the presence of a gene mutation in the SMAD family member 4 (SMAD4) gene in a biological sample from a colorectal cancer patient is an indication that the patient will respond to combination treatment with a histone deacetylase inhibitor and a proteasome inhibitor, or
   iii) the presence of one or more gene mutations in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL) in a biological sample from a cancer patient is an indication that the patient will respond to combination treatment with a histone deacetylase inhibitor and a proteasome inhibitor, or 3) an association study that associates gene expression analysis with treatment type, comprising
   i) measuring the expression level of a gene selected from the group consisting of pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); and abhydrolase domain containing 14A (ABHD14A) in a biological sample from the cancer patient; and
   a) correlating a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4 as an indication that the patient will respond to treatment with a histone deacetylase inhibitor; or correlating a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A as an indication that the patient will respond to treatment with a histone deacetylase inhibitor, or
   ii) measuring the expression level of a gene selected from the group consisting of UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); in a biological sample from the cancer patient; and
   a) correlating a low expression level, as compared to a normalized gene expression level of the gene, of any one or more of the genes UGDH, H2AFY2, MYO5C, NPNT, and KIAA1598 as an indication that the patient will respond to combination treatment with a histone deacetylase inhibitor and a proteasome inhibitor; or correlating a high expression level of the gene, as compared to a normalized gene expression level, of any one or more of the genes SRGN, COL6A3, GPSM3, HSD11B1, PEX6, RAC2, SSX5, and ACBD3 as an indication that the patient will respond to combination treatment with a histone deacetylase inhibitor and a proteasome inhibitor, b) evaluating the data regarding cancer types, gene mutations, or gene expression levels to determine whether the patient will respond to such treatment; and c) administering to a patient that will respond to treatment a therapeutically effective amount of a histone deacetylase (HDAC) inhibitor and a proteasome inhibitor.

An embodiment of the invention provides a method for treating breast cancer in a patient in need thereof comprising the steps of:

a) measuring the expression level of each of the following genes: transforming growth factor beta-3 (TGFB3); CD44 molecule (Indian blood group) (CD44); cytochrome p450, family 4, subfamily Z, polypeptide 2 pseudogene (CYP4Z2P); interferon-induced protein 44 (IFI44); solute carrier family 9, subfamily A (NHE6, cation proton antiporter 6), member 6 (SLC9A6); v-erb-b2 erythroblastic leukemia viral oncogene homolog 2, neuro/glioblastoma derived oncogene homolog (avian) (ERBB2); v-yes-1 Yamaguchi sarcoma viral related oncogene homolog (LYN); pleckstrin homology-like domain, family A, member 1 (PHLDA1); peroxisome proliferator-activated receptor gamma (PPARG); dicarbonyl/L-xylulose reductase (DCXR); uridine phosphorylase 1 (UPP1); ATP-binding cassette, subfamily C (CFTR/MRP), member 11 (ABCC11); aldo-keto reductase family 1, member C2 (dihydrodiol dehydrogenase 2; bile acid binding protein; 3-alpha hydroxysteroid dehydrogenase, type III) (AKR1C2); BCL2-associated athanogene 2 (BAG2); TLR4 interactor with leucine-rich repeats (TRIL); uncharacterized LOC440335 (LOC440335); inhibin, beta B (INHBB); dickkopf 1 homolog (*Xenopus laevis*) (DKK1); insulin receptor substrate 2 (IRS2); chromosome 17 open reading frame 28 (C17orf28); LIM domain kinase 2 (LIMK2); like-glycosyltransferase (LARGE); coiled-coil domain containing 82 (CCDC82); solute carrier family 40 (iron-regulated transporter), member 1 (SLC40A1); interferon-induced protein with tetratricopeptide repeats 1 (IFIT1); formin-like 2 (FMNL2); leukemia inhibitory factor (LIF); transforming growth factor, beta recetor 2 (70/80 kDa) (TGFBR2); G protein-coupled receptor 160 (GPR160); cytokine inducible SH2-containing protein (CISH); phospholipase C, beta 4 (PLCB4); B-cell linker (BLNK); phospholipase C, gamma 2 (phosphatidylinositol-specific) (PLCG2); caveolin 2 (CAV2); proline dehydrogenase (oxidase) 1 (PRODH); ras homolog family member B (RHOB); interferon-induced protein with tetratricopeptide repeats 3 (IFIT3); calbindin 2 (CALB2); TSPY-like 5 (TSPYL5); chromosome X open reading frame 61 (CXorf61); hematopoietically expressed homeobox (HHEX); cAMP responsive element binding protein 3-like4 (CREB3L4); X-box binding protein 1 (XBP1); SAM pointed domain containing ets trsanscription factor (SPDEF); nuclear receptor coactivator 7 (NCOA7); galanin prepropeptide (GAL); HECT and RLD domain containing E3 ubiquitin protein ligase 5 (HERC5); major histocompatibility complex, class I, A (HLA-A); centromere protein V (CENPV); frequently rearranged in advanced T-cell lymphomas 2 (FRAT2); phospholipase B domain containing 1 (PLBD1); adenosine A2b receptor (ADORA2B); G protein-coupled receptor, family C, group 5, member A (GPRC5A); enoyl CoA hydratase domain containing 1 (ECHDC1); guanylate binding protein 1, interferon-inducible (GBP1); sulfatase 2 (SULF2), uncharacterized LOC100507463 (LOC100507463), and KIAA1324 (KIAA1324) in a biological sample from the breast cancer patient;

b) correlating a high expression level, as compared to a normalized gene expression level of the gene, of the following genes TGFB3, CYP4Z2P, ERBB2, DCXR, ABCC11, TRIL, LOC440335, INHBB, C17orf28, LIMK2, LARGE, SLC40A1, GPR160, CISH, PLCB4, BLNK, PRODH, RHOB, CREB3L4, XBP1, SPDEF, FRAT2, and KIAA1324 as an indication that the patient will respond to such treatment; and correlating a low expression level, as compared to a normalized gene expression level of the gene, of the following genes CD44, IFI44, SLC9A6, LYN, PHLDA1, PPARG, UPP1, AKR1C2, BAG2, DKK1, IRS2, IFIT1, FMNL2, LIF, TGFBR2, PLCG2, CAV2, IFIT3, CALB2, TSPYL5, CXorf61, HHEX, NCOA7, GAL, HERC5, HLA-A, CENPV, PLBD1, ADORA2B, GPRC5A, ECHDC1, GBP1, SULF2, and LOC100507463 as an indication that the patient will respond to such treatment;

c) administering to a patient that will respond to treatment a therapeutically effective amount of a histone deacetylase (HDAC) inhibitor.

An embodiment of the invention provides a histone deacetylase (HDAC) inhibitor for use in treating breast cancer in a patient who overexpresses the human epidermal growth factor receptor 2 (Her2) protein, as compared to a normalized protein expression level of the protein.

An embodiment of the invention provides the combination of a histone deacetylase (HDAC) inhibitor and a proteasome inhibitor for use in treating colorectal cancer in a patient having a gene mutation in the SMAD family member 4 (SMAD4) gene.

An embodiment of the invention provides the combination of a histone deacetylase (HDAC) inhibitor and a proteasome inhibitor for use in treating cancer in a patient having a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL).

An embodiment of the invention provides a histone deacetylase (HDAC) inhibitor for use in treating cancer in a patient who has a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4, or a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A.

An embodiment of the invention provides the combination of a histone deacetylase (HDAC) inhibitor and a proteasome inhibitor for use in treating cancer in a patient who has a low expression level, as compared to a normalized gene expression level of the gene, of any one or more of the genes UGDH, H2AFY2, MYO5C, NPNT, and KIAA1598, or a high expression level, as compared to a normalized gene expression level, of any one or more of the genes SRGN, COL6A3, GPSM3, HSD11B1, PEX6, RAC2, SSX5, and ACBD3.

An embodiment of the invention provides a histone deacetylase (HDAC) inhibitor for use in treating breast cancer in a patient who overexpresses the human epidermal growth factor receptor 2 (Her2) protein, as compared to a normalized protein expression level of the protein, wherein the patient has been tested and found to have the Her2 protein.

An embodiment of the invention provides the combination of a histone deacetylase (HDAC) inhibitor and a proteasome inhibitor for use in treating colorectal cancer in a patient having a gene mutation in the SMAD family member 4 (SMAD4) gene, wherein the patient has been tested and found to have a mutation in the SMAD4 gene.

An embodiment of the invention provides the combination of a histone deacetylase (HDAC) inhibitor and a proteasome inhibitor for use in treating cancer in a patient having a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL), wherein the patient has been tested and found to have a mutation in any one of the PTEN, EGFR, EZH2, SETD2, and VHL genes.

An embodiment of the invention provides a histone deacetylase (HDAC) inhibitor for use in treating cancer in a patient who has a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4, or a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A, wherein the patient has been tested and found to have a low expression level of any one or more of the genes PCBD1, PPP2R2C, NEDD4, P4HA2, SLC2A4RG, SULF2, LAPTM4A, PAPSS2, AKR1C1, PTPN12, and DCUN1D4, or a high expression level of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A.

An embodiment of the invention provides the combination of a histone deacetylase (HDAC) inhibitor and a proteasome inhibitor for use in treating cancer in a patient who has a low expression level, as compared to a normalized gene expression level of the gene, of any one or more of the genes UGDH, H2AFY2, MYO5C, NPNT, and KIAA1598, or a high expression level, as compared to a normalized gene expression level, of any one or more of the genes SRGN, COL6A3, GPSM3, HSD11B1, PEX6, RAC2, SSX5, and ACBD3, wherein the patient has been tested and found to have a low expression level of any one or more of the genes UGDH, H2AFY2, MYO5C, NPNT, and KIAA1598, or a high expression level of any one or more of the genes UGDH, H2AFY2, MYO5C, NPNT, and KIAA1598.

An embodiment of the invention provides a histone deacetylase (HDAC) inhibitor for use in treating breast cancer in a patient wherein the treatment comprises testing the patient for overexpression of the human epidermal growth factor receptor 2 (Her2) protein, as compared to a normalized protein expression level of the protein, and administering the HDAC inhibitor if the patient overexpresses the Her2 protein.

An embodiment of the invention provides the combination of a histone deacetylase (HDAC) inhibitor and a proteasome inhibitor for use in treating colorectal cancer in a patient wherein the treatment comprises testing the patient for a gene mutation in the SMAD family member 4 (SMAD4) gene and administering the combination if a mutation in the SMAD4 gene is found.

An embodiment of the invention provides the combination of a histone deacetylase (HDAC) inhibitor and a proteasome inhibitor for use in treating cancer in a patient wherein the treatment comprises testing the patient for a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL), and administering the combination if a mutation in any one of the PTEN, EGFR, EZH2, SETD2, and VHL genes is found.

An embodiment of the invention provides a histone deacetylase (HDAC) inhibitor for use in treating cancer in a patient wherein the treatment comprises testing the patient for a low expression level, as compared to a normalized gene expression level of the gene, of any one or more of the genes PCBD1, PPP2R2C, NEDD4, P4HA2, SLC2A4RG, SULF2, LAPTM4A, PAPSS2, AKR1C1, PTPN12, and DCUN1D4, or a high expression level, as compared to a normalized gene expression level of the gene, of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A, and administering the combination if a low expression level of any one or more of the genes PCBD1, PPP2R2C, NEDD4, P4HA2, SLC2A4RG, SULF2, LAPTM4A, PAPSS2, AKR1C1, PTPN12, and DCUN1D4, or a high expression level of any one or more of the genes RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A is found.

An embodiment of the invention provides the combination of a histone deacetylase (HDAC) inhibitor and a proteasome inhibitor for use in treating cancer in a patient wherein the treatment comprises testing the patient for a low expression level, as compared to a normalized gene expression level of the gene, of any one or more of the genes UGDH, H2AFY2, MYO5C, NPNT, and KIAA1598, or a high expression level, as compared to a normalized gene expression level, of any one or more of the genes SRGN, COL6A3, GPSM3, HSD11B1, PEX6, RAC2, SSX5, and ACBD3, and administering the combination if a low expression level of any one or more of the genes UGDH, H2AFY2, MYO5C, NPNT, and KIAA1598, or a high expression level of any one or more of the genes UGDH, H2AFY2, MYO5C, NPNT, and KIAA1598 is found.

An embodiment of the invention provides a method of testing for responsiveness of a patient to treatment with a histone deacetylase (HDAC) inhibitor, the method comprising testing for overexpression, as compared to a normalized protein expression level of the protein, of the human epidermal growth factor receptor 2 (Her2) protein. In a specific embodiment, the testing is performed in vitro.

An embodiment of the invention provides for use of the overexpression, as compared to a normalized protein expression level of the protein, of the human epidermal growth factor receptor 2 (Her2) protein for assessing responsiveness of a patient to treatment with a histone deacetylase (HDAC) inhibitor.

An embodiment of the invention provides for use of a probe for the human epidermal growth factor receptor 2 (Her2) protein for assessing responsiveness of a patient to treatment with a histone deacetylase (HDAC) inhibitor.

An embodiment of the invention provides the overexpression, as compared to a normalized protein expression level of the protein, of the human epidermal growth factor receptor 2 (Her2) protein for use in treating breast cancer in a patient in need thereof wherein the treatment comprises identifying the overexpression of the Her2 protein in a patient and then administering a histone deacetylase (HDAC) inhibitor if the patient is found to overexpress the Her2 protein.

An embodiment of the invention provides a gene mutation in the SMAD family member 4 (SMAD4) gene for use in treating colorectal cancer in a patient in need thereof wherein the treatment comprises identifying a mutation in the SMAD4 gene in a patient and then administering the combination of a histone deacetylase (HDAC) inhibitor and a proteasome inhibitor if the patient is found to have a mutation in the SMAD4 gene.

An embodiment of the invention provides a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL) for use in treating cancer in a patient in need thereof wherein the treatment comprises identifying a mutation in any one of the PTEN, EGFR, EZH2, SETD2, and VHL genes in a patient wherein the treatment comprises identifying the presence of the mutation in any one of the PTEN, EGFR, EZH2, SETD2, and VHL genes and then administering a histone deacetylase (HDAC) inhibitor and a proteasome inhibitor if the patient is found to have a mutation in any one of the PTEN, EGFR, EZH2, SETD2, and VHL genes.

An embodiment of the invention provides a probe for the human epidermal growth factor receptor 2 (Her2) protein for use in treating breast cancer in a patient in need thereof wherein the treatment comprises using the probe to identify the overexpression, as compared to a normalized protein expression level of the protein, of the Her2 protein in a patient and then administering a histone deacetylase (HDAC) inhibitor if the patient is found to overexpress the Her2 protein.

In certain embodiments of the methods and uses described above, the HDAC6 inhibitor is a compound of formula I:

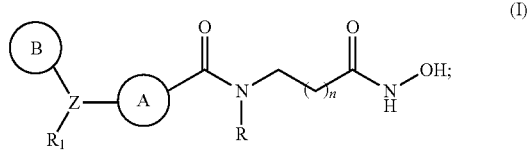

or a pharmaceutically acceptable salt, ester or prodrug thereof.

In certain embodiments of the methods and uses described above, the HDAC6 inhibitor is Compound A.

Association Study of Cancer Types

An embodiment of the invention comprises an association study of cancer types, which associates treatment effect by tumor type.

Preferably, numerous cancer cell lines are used in the association study. For example, the cell lines can be specific for breast cancer, hematologic cancer, colorectal cancer, lung cancer, skin cancer, brain cancer, renal cancer, liver cancer, prostate cancer, ovarian cancer, and stomach cancer. However, cell lines specific for other forms of cancer may be used. In addition, multiple cell lines that are specific for one form of cancer, such as breast cancer, may be used.

In this association study of cancer types, each cell line is cultured and treated with an HDAC inhibitor, with or without another cancer treatment. The viabilities of the cell lines are then measured at the end of the treatments. Viability may be measured by any means known in the art. Preferably, the sensitivities of the cell lines are described using the concentration of HDAC inhibitor that provides 50% inhibition of cell viabilities ($IC_{50}$).

For example, a specific embodiment of this study that is described in more detail in the Examples determined that brain/neuronal cancer, breast cancer, lymphoid cancer, kidney cancer, colon cancer, cancer of the large intestine, and skin cancer were each sensitive to combination treatment with a HDAC inhibitor and another cancer treatment. In addition, the specific embodiment of this study determined that hematologic malignant cancer was the most sensitive to treatment with both a HDAC inhibitor alone, or combination treatment with a HDAC inhibitor and another cancer treatment.

Association Study of Gene Mutations

Another embodiment of the invention comprises an association study of gene mutations, which associates gene mutation analysis with treatment type and tumor type.

Preferably, numerous cancer cell lines are used in the association study. For example, the cell lines can be specific for breast cancer, hematologic cancer, colorectal cancer, lung cancer, skin cancer, brain cancer, renal cancer, liver cancer, prostate cancer, ovarian cancer, and stomach cancer. However, cell lines specific for other forms of cancer may be used. In addition, multiple cell lines that are specific for one form of cancer, such as breast cancer, may be used.

In this association study of gene mutations, each cell line is cultured and treated with an HDAC inhibitor, with or without another cancer treatment. The viabilities of the cell lines are then measured at the end of the treatments. Viability may be measured by any means known in the art. Preferably, the sensitivities of the cell lines are described using the concentration of HDAC inhibitor that provides 50% inhibition of cell viabilities ($IC_{50}$).

Preferably numerous oncogene/tumor suppressor genes are analyzed to generate the results of this study. For example, in the present methods, numerous common oncogene/tumor suppressor genes can be analyzed.

The genes are analyzed to determine an association between the genotype and the cell sensitivities to the treatments.

The mutation profiles of the cell lines may be analyzed by any means known in the art. Preferably, the mutation profiles of the cell lines are downloaded from the Sanger COSMIC DB on the Internet: www dot sanger dot ac dot uk/cosmic.

The statistical significance of the association between the genotype and the cell sensitivities to the treatments may be analyzed by any means known in the art. For each gene locus, it is preferable to use the "Fisher's Exact Test" to calculate statistical significance ($p<0.05$) of association between the genotype and the cell sensitivities to the treatments.

For example, a specific embodiment of this study that is described in more detail in the Examples correlated epidermal growth factor receptor 2 (Her2) protein overexpression, as compared to a normalized protein expression level of the protein, caused by erythroblastic leukemia viral oncogene homolog 2 (ERBB2) gene amplification or by any other means, in a biological sample from a breast cancer patient as an indication that the patient will respond to treatment with an HDAC inhibitor. The specific embodiment of this study also correlated the presence of a gene mutation in the SMAD family member 4 (SMAD4) gene in a biological sample from a colorectal cancer patient as an indication that the patient will respond to combination treatment with a HDAC inhibitor and another cancer treatment. The specific embodiment of this study further correlated the presence of a gene mutation in a gene selected from the group consisting of phosphatase and tensin homolog (PTEN), epidermal growth factor receptor oncogene (EGFR), histone-lysine N-methyltransferase (EZH2), SET domain containing 2 (SETD2), and von Hippel-Lindau tumor suppressor (VHL) in a biological sample from a cancer patient as an indication that the patient will respond to combination treatment with a HDAC inhibitor and another cancer treatment.

However, the specific embodiment of this study correlated the presence of the basal-type or triple negative mutations (estrogen receptor-negative, progesterone receptor-negative and HER2/neu-negative) in a biological sample from a breast cancer patient as an indication that the patient will not respond to treatment with an HDAC inhibitor.

Association Study of Gene Expression

A further embodiment of the invention comprises an association study of gene expression levels, which associates gene expression levels with tumor type.

Preferably, numerous cancer cell lines are used in the association study. For example, the cell lines can be specific for breast cancer, hematologic cancer, colorectal cancer, lung cancer, skin cancer, brain cancer, renal cancer, liver cancer, prostate cancer, ovarian cancer, and stomach cancer. However, cell lines specific for other forms of cancer may be used. In addition, multiple cell lines that are specific for one form of cancer, such as breast cancer, may be used.

In this association study of gene expression, each cell line is cultured and treated with an HDAC inhibitor, with or without another cancer treatment. The viabilities of the cell lines are then measured at the end of the treatments. Viability may be measured by any means known in the art. Preferably, the sensitivities of the cell lines are described using the concentration of HDAC inhibitor that provides 50% inhibition of cell viabilities ($IC_{50}$).

The gene expression profiles of the cell lines used in the study should be obtained. These may be obtained by any means known in the art. Preferably, the gene expression profiles are obtained from the ArrayExpress (AE) database on the Internet: www dot ebi dot ac dot uk/arrayexpress/, which is maintained by the European Bioinformatics Institute. Alternatively, the gene expression profiles are obtained from the caArray database on the Internet: <URL:https://cabig.nci.nih.gov/caArray_GSKdata/>, which is from NIH. More preferably, the gene expression profiles of the cell lines are obtained from a combination of the above two databases.

Next, the expression intensity of the individual genes should be obtained and normalized between individual cell lines. This may be done by any means known in the art. It is preferable to download the Affymetrix CEL files, which contain the expression intensity of individual genes from these public databases, and then use the R/BioConductor packages on the Internet: <URL:http://bioconductor.org> in order to normalize the gene-expression values between individual cell lines. The correlation coefficient and its significance ($p<0.001$) may be calculated using the CORTEST function of R package between the $IC_{50}$ values and the normalized gene expression levels for each probe-set. For validation, only genes with all probe sets showing significant correlations should be reported; and genes should be removed if any of its probe-sets are non-significant.

Alternatively, the level of expression of a biomarker gene in a sample may be assessed by detecting the level of expression of a biomarker protein encoded by the biomarker gene. The level of expression of the biomarker protein may be detected using a reagent that specifically binds with the marker protein. Preferably, the reagent is selected from the group consisting of an antibody, a fragment of an antibody, and an antibody derivative.

There are many different types of immunoassays that may be used in the method of the present invention, e.g., enzyme linked immunoabsorbent assay (ELISA), fluorescent immunosorbent assay (FIA), chemical linked immunosorbent assay (CLIA), radioimmuno assay (RIA), and immunoblotting. For a review of the different immunoassays which may be used, see: Lottspeich and Zorbas (eds.), Bioanalytik, $1^{st}$ edition 1998, Spektrum Akademischer Verlag, Heidelberg, Berlin, Germany. Therefore, the level of expression may be determined using a method selected from the group consisting of proteomics, flow cytometry, immunocytochemistry, immunohistochemistry, enzyme-linked immunosorbent assay, multi-channel enzyme-linked immunosorbent assay, and variations of these methods.

Alternatively, the level of expression of a biomarker gene in a biological sample may be assessed by detecting the level of expression of a transcribed biomarker polynucleotide encoded by the biomarker gene. For example, the transcribed biomarker polynucleotide is a cDNA, mRNA or hnRNA.

The step of detecting may further comprise amplifying the transcribed polynucleotide. The amplification can be performed with the polymerase chain reaction which specifically amplifies nucleic acids to detectable amounts. Other possible amplification reactions are the Ligase Chain Reaction (LCR; Wu D. Y. and Wallace R. B., Genomics 4 (1989) 560-569; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh, D. Y. et al., Proc. Natl. Acad. Sci. USA 86 (1989) 1173-1177; Guatelli, J. C. et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qβ-amplification (for a review see e.g. Whelen, A. C. and Persing, D. H., Annu. Rev. Microbiol. 50 (1996) 349-373; Abramson, R. D. and Myers T. W., Curr. Opin. Biotechnol. 4 (1993) 41-47). For example, the step of detecting can use the method of quantitative reverse transcriptase polymerase chain reaction.

Other suitable polynucleotide detection methods are known in the field and are described in standard textbooks, such as Sambrook J. et al., Molecular Cloning: A Laboratory Manual, Cold Spring Harbor Laboratory Press, Cold Spring Harbor, N.Y., 1989; and Ausubel, F. et al., Current Protocols in Molecular Biology, 1987, J. Wiley and Sons, NY. There may be also further purification steps before the polynucleotide detection step is carried out as, for example, a precipitation step. The detection methods may include but are not limited to the binding or intercalating of specific dyes as ethidiumbromide, which intercalates into the double-stranded polynucleotides and changes their fluorescence thereafter. The purified polynucleotide may also be separated by electrophoretic methods optionally after a restriction digest and visualized thereafter. There are also probe-based assays which exploit the oligonucleotide hybridisation to specific sequences and subsequent detection of the hybrid. It is also possible to sequence the DNA after further steps known in the field. A preferred template-dependent DNA polymerase is Taq polymerase.

Alternatively, the level of expression of a biomarker gene is assessed by detecting the presence of the transcribed marker polynucleotide in a sample with a probe that anneals with the transcribed marker polynucleotide under stringent hybridization conditions. This method may be performed in a homogeneous assay system. An example of a "homogeneous" assay system is the TaqMan™ system that has been detailed in U.S. Pat. Nos. 5,210,015, 5,804,375 and 5,487,972. Briefly, the method is based on a double-labelled probe and the 5'-3' exonuclease activity of Taq DNA polymerase. The probe is complementary to the target sequence to be amplified by the PCR process and is located between the two PCR primers during each polymerisation cycle step. The probe has two fluorescent labels attached to it. One is a reporter dye, such as 6-carboxyfluorescein (FAM), which has its emission spectra quenched by energy transfer due to the spatial proximity of a second fluorescent dye, 6-carboxy-tetramethyl-rhodamine (TAMRA). In the course of each amplification cycle, the Taq DNA polymerase in the process of elongating a primed DNA strand displaces and degrades the annealed probe, the latter due to the intrinsic 5'-3' exonuclease activity of the polymerase. The mechanism also frees the reporter dye from the quenching activity of TAMRA. As a consequence, the fluorescent activity increases with an increase in cleavage of the probe, which is proportional to the amount of PCR product formed. Accordingly, an amplified target sequence is measured by detecting the intensity of released fluorescence label. Another example for "homogeneous" assay systems are provided by the formats used in the LightCycler™ instrument (see e.g. U.S. Pat. No. 6,174,670), some of them sometimes called "kissing probe" formats. Again, the principle is based on two interacting dyes which, however, are characterized in that the emission wavelength of a donor-dye excites an acceptor-dye by fluorescence resonance energy transfer. The COBAS™ AmpliPrep instrument (Roche Diagnostics GmbH, D-68305 Mannheim, Germany) was introduced to expand automation by isolating target sequences using biotinylated sequence-specific capture probes along with streptavidin-coated magnetic particles (Jungkind, D., J. Clin. Virol. 20 (2001) 1-6; Stelzl, E. et al., J. Clin. Microbiol. 40 (2002) 1447-1450). It has lately been joined by an additional versatile tool, the Total Nucleic Acid Isolation (TNAI) Kit (Roche Diagnostics). This laboratory-use reagent allows the generic, not sequence-specific isolation of all nucleic acids from plasma and serum on the COBAS™ AmpliPrep instrument based essentially on the method developed by Boom, R. et al., J. Clin. Microbiol. 28 (1990) 495-503.

For example, a specific embodiment of this study that is described in more detail in the Examples correlated a low expression level, as compared to a normalized gene expression level of the gene, of any one or more of the genes selected from the group consisting of pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); and DCN1, defective in cullin neddylation 1, domain containing 4 (S. cerevisiae) (DCUN1D4) in a biological sample from a cancer patient as an indication that the patient will respond to treatment with an HDAC inhibitor. The specific embodiment of this study also correlated a high expression level, as compared to a normalized gene expression level of the gene, of any one or more of the genes selected from the group consisting of ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); and abhydrolase domain containing 14A (ABHD14A) in a biological sample from a cancer patient as an indication that the patient will respond to treatment with an HDAC inhibitor. In addition, the specific embodiment of this study correlated a low expression level, as compared to a normalized gene expression level of the gene, of any one or more of the genes selected from the group consisting of UDP-glucose dehydrogenase (UGDH); H2A histone family, member Y2 (H2AFY2); myosin VC (MYO5C); nephronectin (NPNT); and KIAA1598 (KIAA1598) in a biological sample from a cancer patient as an indication that the patient will respond to combination treatment with an HDAC inhibitor and another cancer treatment. Further, the specific embodiment of this study correlated a high expression level, as compared to a normalized gene expression level of the gene, of any one or more of the genes selected from the group consisting of serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3) in a biological sample from a cancer patient as an indication that the patient will respond to combination treatment with an HDAC inhibitor and another cancer treatment.

58 Gene Signature Prediction Model for Breast Cancer

An embodiment of the invention comprises a 58 gene signature prediction model that can be used to identify breast cancer patients that will respond to treatment with an HDAC inhibitor.

Breast cancer cell lines were studied to produce a 58 gene signature prediction model using a correlation analysis of their IC50 values and their gene expression data published at the CCLE database (www dot broad institute dot org/ccle/home).

For the 58 genes in the "signature", 35 low expression and 23 high expression genes related to the "sensitive" signature, while 35 high expression and 23 low expression related to the "resistant" signature (see FIG. 1). The names of the 58 genes are: transforming growth factor beta-3 (TGFB3); CD44 molecule (Indian blood group) (CD44); cytochrome p450, family 4, subfamily Z, polypeptide 2 pseudogene (CYP4Z2P); interferon-induced protein 44 (IFI44); solute carrier family 9, subfamily A (NHE6, cation proton antiporter 6), member 6 (SLC9A6); v-erb-b2 erythroblastic leukemia viral oncogene homolog 2, neuro/glioblastoma derived oncogene homolog (avian) (ERBB2); v-yes-1 Yamaguchi sarcoma viral related oncogene homolog (LYN); pleckstrin homology-like domain, family A, member 1 (PHLDA1); peroxisome proliferator-activated receptor gamma (PPARG); dicarbonyl/L-xylulose reductase (DCXR); uridine phosphorylase 1 (UPP1); ATP-binding cassette, subfamily C (CFTR/MRP), member 11 (ABCC11); aldo-keto reductase family 1, member C2 (dihydrodiol dehydrogenase 2; bile acid binding protein; 3-alpha hydroxysteroid dehydrogenase, type III) (AKR1C2); BCL2-associated athanogene 2 (BAG2); TLR4 interactor with leucine-rich repeats (TRIL); uncharacterized LOC440335 (LOC440335); inhibin, beta B (INHBB); dickkopf 1 homolog (Xenopus laevis) (DKK1); insulin receptor substrate 2 (IRS2); chromosome 17 open reading frame 28 (C17orf28); LIM domain kinase 2 (LIMK2); like-glycosyltransferase (LARGE); coiled-coil domain containing 82

(CCDC82); solute carrier family 40 (iron-regulated transporter), member 1 (SLC40A1); interferon-induced protein with tetratricopeptide repeats 1 (IFIT1); formin-like 2 (FMNL2); leukemia inhibitory factor (LIF); transforming growth factor, beta recetor 2 (70/80 kDa) (TGFBR2); G protein-coupled receptor 160 (GPR160); cytokine inducible SH2-containing protein (CISH); phospholipase C, beta 4 (PLCB4); B-cell linker (BLNK); phospholipase C, gamma 2 (phosphatidylinositol-specific) (PLCG2); caveolin 2 (CAV2); proline dehydrogenase (oxidase) 1 (PRODH); ras homolog family member B (RHOB); interferon-induced protein with tetratricopeptide repeats 3 (IFIT3); calbindin 2 (CALB2); TSPY-like 5 (TSPYL5); chromosome X open reading frame 61 (CXorf61); hematopoietically expressed homeobox (HHEX); cAMP responsive element binding protein 3-like4 (CREB3L4); X-box binding protein 1 (XBP1); SAM pointed domain containing ets trsanscription factor (SPDEF); nuclear receptor coactivator 7 (NCOA7); galanin prepropeptide (GAL); HECT and RLD domain containing E3 ubiquitin protein ligase 5 (HERC5); major histocompatibility complex, class I, A (HLA-A); centromere protein V (CENPV); frequently rearranged in advanced T-cell lymphomas 2 (FRAT2); phospholipase B domain containing 1 (PLBD1); adenosine A2b receptor (ADORA2B); G protein-coupled receptor, family C, group 5, member A (GPRC5A); enoyl CoA hydratase domain containing 1 (ECHDC1); guanylate binding protein 1, interferon-inducible (GBP1); sulfatase 2 (SULF2), uncharacterized LOC100507463 (LOC100507463), and KIAA1324 (KIAA1324).

Of the 58 genes above, the following high expression genes are related to the "sensitive" signature: TGFB3, CYP4Z2P, ERBB2, DCXR, ABCC11, TRIL, LOC440335, INHBB, C17orf28, LIMK2, LARGE, SLC40A1, GPR160, CISH, PLCB4, BLNK, PRODH, RHOB, CREB3L4, XBP1, SPDEF, FRAT2, and KIAA1324; and the following low expression genes are related to the "sensitive" signature: CD44, IFI44, SLC9A6, LYN, PHLDA1, PPARG, UPP1, AKR1C2, BAG2, DKK1, IRS2, IFIT1, FMNL2, LIF, TGFBR2, PLCG2, CAV2, IFIT3, CALB2, TSPYL5, CXorf61, HHEX, NCOA7, GAL, HERC5, HLA-A, CENPV, PLBD1, ADORA2B, GPRC5A, ECHDC1, GBP1, SULF2, and LOC100507463.

Of the 58 genes above, the following low expression genes are related to the "resistant" signature: TGFB3, CYP4Z2P, ERBB2, DCXR, ABCC11, TRIL, LOC440335, INHBB, C17orf28, LIMK2, LARGE, SLC40A1, GPR160, CISH, PLCB4, BLNK, PRODH, RHOB, CREB3L4, XBP1, SPDEF, FRAT2, and KIAA1324; and the following high expression genes are related to the "resistant" signature: CD44, IFI44, SLC9A6, LYN, PHLDA1, PPARG, UPP1, AKR1C2, BAG2, DKK1, IRS2, IFIT1, FMNL2, LIF, TGFBR2, PLCG2, CAV2, IFIT3, CALB2, TSPYL5, CXorf61, HHEX, NCOA7, GAL, HERC5, HLA-A, CENPV, PLBD1, ADORA2B, GPRC5A, ECHDC1, GBP1, SULF2, and LOC100507463.

This 58 gene signature prediction model may then be used to predict the sensitivity of breast tumor tissue samples from patients in order to determine the tumor's sensitivity or resistance to treatment with an HDAC inhibitor.

The sensitive group of breast tumor tissues was enriched for three clinical breast cancer diagnosis markers: ER positive, PR positive, and low grade breast tumors. The resistant group of breast tumor tissues was associated with a triple negative (ER-PR-Her2/neu-) marker. Likewise, these three clinical breast cancer diagnosis markers may be used to predict the sensitivity of breast tumor tissue samples from patients in order to determine the tumor's sensitivity or resistance to treatment with an HDAC inhibitor.

Histone Deacetylase (HDAC) Inhibitors

An HDAC inhibitor used in the methods of the invention can be any HDAC inhibitor, such as a small molecule organic compound, an antibody, a siRNA, an aptamer, a nucleic acid, a protein, or a peptide. Preferably, the HDAC inhibitor is a small molecule organic compound.

Preferably, the HDAC inhibitor is an HDAC6 inhibitor. This means that the HDAC inhibitor selectively inhibits HDAC6 over other forms of HDAC.

In one aspect, the HDAC6 inhibitor is a compound of formula I:

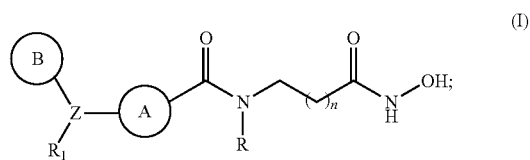

or a pharmaceutically acceptable salt, ester or prodrug thereof,
wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, $C(O)-R_2$, $C(O)O-R_2$, or $S(O)_p$, each of which may be optionally substituted; or (ii) when Z is CR*, $R_1$ may be optionally substituted branched alkyl, $OR_3$, or $N(R_3)(R_3)$, $-CH_2CH_2OH$, $OCH_2CH_2OH$, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocloalkyl, aryl, or heteroaryl, each of which is optionally substituted;

each $R_3$ is independently alkyl, cycloalkyl, heterocloalkyl, aryl, or heteroaryl, each of which is optionally substituted;

n is 4, 5, 6, 7 or 8; and p is 0, 1, or 2.

In one embodiment, the ring A is phenyl, naphthyl, anthracenyl, pyridinyl, pyrimidinyl, pyrazinyl, indolyl, imidazolyl, oxazolyl, furyl, thienyl, thiazolyl, triazolyl, isoxazolyl, quinolinyl, pyrrolyl, pyrazolyl, or 5,6,7,8-tetrahydroisoquinoline; each of which may be optionally substituted.

In another embodiment, the ring B is phenyl, naphthyl, anthracenyl, pyridinyl, pyrimidinyl, pyrazinyl, indolyl, imidazolyl, oxazolyl, furyl, thienyl, thiazolyl, triazolyl, isoxazolyl, quinolinyl, pyrrolyl, pyrazolyl, or 5,6,7,8-tetrahydroisoquinoline; each of which may be optionally substituted.

In certain embodiments, $R_1$ is H, optionally substituted alkyl, optionally substituted aryl, or optionally substituted heteroaryl, or $R_1$ is OH or alkoxy.

In a further embodiment, $R_1$ is H, methyl, ethyl, propyl, i-propyl, butyl, i-butyl, t-butyl, pentyl, hexyl, phenyl, naphthyl, pyridinyl, OH, $OCH_3$, $OCH_2CH_3$, O—Pr, O-iPr, O-Bu, O-sBu, or O-tBu; each of which may be optionally substituted.

In various embodiments, $R_1$ is OH, alkoxy, $NH_2$, NH(alkyl), N(alkyl)(alkyl), NH-aryl, NH-heteroaryl, N(aryl)(aryl), N(aryl)(heteroaryl), or N(heteroaryl)(heteroaryl).

In other embodiments, the carbonyl and the Z group attached to ring A are disposed para to each other.

In other embodiments, the carbonyl and Z group attached to ring A are disposed meta to each other.

In another embodiment, the carbonyl and the Z group attached to ring A are disposed ortho to each other.

In one embodiment, the HDAC6 inhibitor is a compound formula II:

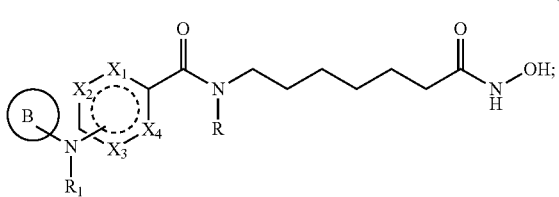

(II)

or a pharmaceutically acceptable salt, ester or prodrug thereof,
wherein,
each of $X_1$, $X_2$, $X_3$, or $X_4$ is independently N, CR', O, S, NCR', CR'CR', OCR', SCR', or absent, or $X_1$ or $X_4$ may be joined with R to form a bicyclic ring; wherein up to three of $X_1$, $X_2$, $X_3$, or $X_4$ may be N;
ring B is an optionally substituted aryl or an optionally substituted heteroaryl;
$R_1$ is H, alkyl, haloalkyl, alkenyl, aryl, arylalkyl, heteroaryl, heterocyclic, carbocyclic, C(O)—$R_2$, or C(O)O—$R_2$, each of which may be optionally substituted;
R is H or an optionally substituted alkyl; or R and $X_1$ or $X_4$ may be joined to form a fused bicyclic ring which may be optionally substituted;
each R' is independently H, optionally substituted alkyl, halo, OH, $NH_2$, NHR", haloalkyl, CN, $N_3$, $NO_2$;
R" is H or alkyl; and
$R_2$ is alkyl, cycloalkyl, heterocycloalkyl, aryl, or heteroaryl, each of which is optionally substituted.

In certain embodiments, $X_1$, $X_2$, $X_3$, and $X_4$ are all CR'.

In other embodiments, $X_2$ and $X_3$, are N and $X_1$ and $X_4$ are CR'.

In another embodiment, $X_2$ and $X_3$, are CR' and $X_1$ and $X_4$ are N.

In still other embodiments, $X_2$, is N; $X_3$ is S, N or O; $X_1$ is CR' and $X_4$ is absent.

In one embodiment, ring B is phenyl, pyridinyl, pyrimidinyl, or pyrazinyl; each of which may be optionally substituted.

In a further embodiment, ring B is substituted by alkyl, aryl, heteroaryl, cycloalkyl, heterocycloalkyl, aralkyl, haloalkyl, hal, OH, $NH_2$, NHR", CN, $N_3$, or $NO_2$.

In certain embodiments, $R_1$ is H, alkyl, aryl, arylalkyl, or heteroaryl, each of which may be optionally substituted.

In another embodiment, the HDAC6 inhibitor is a compound of formula III:

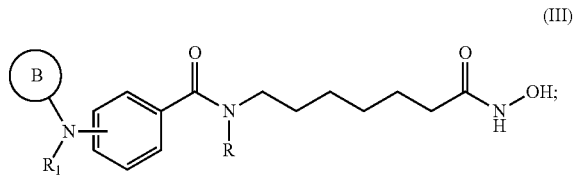

(III)

or a pharmaceutically acceptable salt, ester or prodrug thereof,
wherein,
ring B is an optionally substituted aryl or an optionally substituted heteroaryl;
$R_1$ is H, alkyl, haloalkyl, alkenyl, aryl, arylalkyl, heteroaryl, heterocyclic, carbocyclic, C(O)—$R_2$, or C(O)O—$R_2$, each of which may be optionally substituted;
$R_2$ is optionally substituted heteroaryl, and
R is H or an optionally substituted alkyl; or R and the phenyl ring may be joined to form a fused [6,5] bicyclic ring which may be optionally substituted.

In one embodiment, ring B is phenyl, pyridinyl, pyrimidinyl, or pyrazinyl; each of which may be optionally substituted.

In a further embodiment, ring B is substituted by alkyl, aryl, aralkyl, haloalkyl, hal, OH, $NH_2$, CN, or $NO_2$.

In other embodiments, $R_1$ is H, alkyl, aryl, arylalkyl, heteroaryl, C(O)—$R_2$, or C(O)O—$R_2$, each of which may be optionally substituted.

In various embodiments, $R_2$ is optionally substituted pyridinyl.

In another embodiment, the HDAC6 inhibitor is a compound of formula IV:

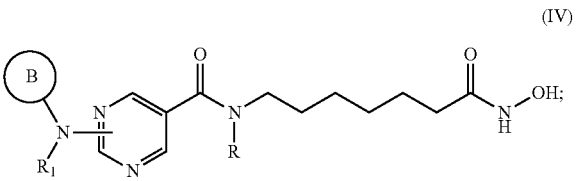

(IV)

or a pharmaceutically acceptable salt, ester or prodrug thereof,
wherein,
ring B is an optionally substituted aryl or an optionally substituted heteroaryl;
$R_1$ is H, alkyl, haloalkyl, alkenyl, aryl, arylalkyl, heteroaryl, heterocyclic, or carbocyclic, each of which may be optionally substituted;
or ring B and $R_1$ may together with the atom to which each is attached, form an optionally substituted heterocyclic, or an optionally substituted heteroaryl, and
R is H or an optionally substituted alkyl; or R and the 1,3-pyrimidinyl ring may be joined to form a fused bicyclic ring which may be optionally substituted.

In certain embodiments, ring B is phenyl, pyridinyl, pyrimidinyl, or pyrazinyl; each of which may be optionally substituted.

In a further embodiment, ring B is substituted by alkyl, aryl, aralkyl, haloalkyl, halo, OH, NH$_2$, CN, or NO$_2$.

In other embodiments, R$_1$ is H, alkyl, aryl, arylalkyl, or heteroaryl, each of which may be optionally substituted.

In another embodiment, R$_1$ is substituted by OH or halo.

In certain embodiments, the ring formed by ring B and R$_1$ is piperidine, pyrrolidine, tetrahydroquinoline, morpholine, piperazine, tetrahydro-triazolo pyrazine, or diazepane, each of which is optionally substituted.

In another embodiment, the HDAC6 inhibitor is a compound of formula V:

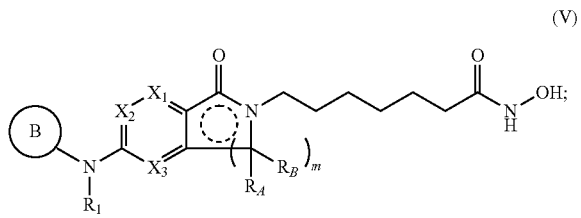

(V)

or a pharmaceutically acceptable salt, ester or prodrug thereof,
wherein,
each of X$_1$, X$_2$, or X$_3$ is independently N or CR';
ring B is an optionally substituted aryl or an optionally substituted heteroaryl;
R$_1$ is H, alkyl, haloalkyl, alkenyl, aryl, arylalkyl, heteroaryl, heterocyclic, or carbocyclic, each of which may be optionally substituted;
each R$_A$ and R$_B$ is independently H, NH(R$_C$), N(R$_C$)(R$_C$), N(R$_C$)CO(R$_C$), CO$_2$H, C(O)R$_C$, C(O)OR$_C$, C(O)NH$_2$, C(O)NH(R$_C$), C(O)N(R$_C$)(R$_C$), SO$_2$R$_C$, SOR$_C$, SR$_C$, alkyl, aryl, arylalkyl, alkoxy, heteroaryl, heterocyclic, and carbocyclic, each of which may be further substituted; or R$_A$ and R$_B$ together with the carbon to which they are attached form a carbonyl;
each R$_C$ is independently H, alkyl, alkenyl, aryl, heteroaryl, cycloalkyl, or heterocyclic, each of which may be further substituted;
R' is H, optionally substituted alkyl, halo, OH, NH$_2$, NHR", haloalkyl, CN, N$_3$, NO$_2$;
R" is H or alkyl; and
m is 1 or 2.

In a related embodiment, the HDAC6 inhibitor is a compound of formula Va:

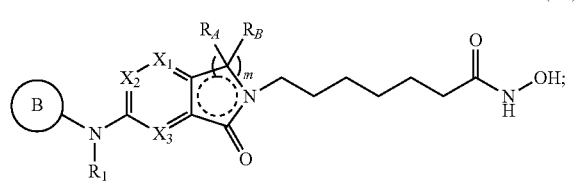

(Va)

or a pharmaceutically acceptable salt, ester or prodrug thereof,
wherein,
each of X$_1$, X$_2$, or X$_3$ is independently N or CR';
ring B is an optionally substituted aryl or an optionally substituted heteroaryl;
R$_1$ is H, alkyl, haloalkyl, alkenyl, aryl, arylalkyl, heteroaryl, heterocyclic, or carbocyclic, each of which may be optionally substituted;
each R$_A$ and R$_B$ is independently H, NH(R$_C$), N(R$_C$)(R$_C$), N(R$_C$)CO(R$_C$), CO$_2$H, C(O)R$_C$, C(O)OR$_C$, C(O)NH$_2$, C(O)NH(R$_C$), C(O)N(R$_C$)(R$_C$), SO$_2$R$_C$, SOR$_C$, SR$_C$, alkyl, aryl, arylalkyl, alkoxy, heteroaryl, heterocyclic, and carbocyclic, each of which may be further substituted; or R$_A$ and R$_B$ together with the carbon to which they are attached form a carbonyl;
each R$_C$ is independently H, alkyl, alkenyl, aryl, heteroaryl, cycloalkyl, or heterocyclic, each of which may be further substituted;
R' is H, optionally substituted alkyl, halo, OH, NH$_2$, NHR", haloalkyl, CN, N$_3$, NO$_2$;
R" is H or alkyl; and
m is 1 or 2.

In one embodiment, X$_1$, X$_2$, and X$_3$, are all independently CR'.

In another embodiment, ring B is phenyl, pyridinyl, pyrimidinyl, or pyrazinyl; each of which may be optionally substituted.

In a further embodiment, ring B is substituted by alkyl, aryl, heteroaryl, cycloalkyl, heterocycloalkyl, aralkyl, haloalkyl, halo, OH, NH$_2$, NHR", CN, N$_3$, or NO$_2$.

In certain embodiments, R$_1$ is H, alkyl, aryl, arylalkyl, or heteroaryl, each of which may be optionally substituted.

In another embodiment, the HDAC6 inhibitor is a compound of formula VI:

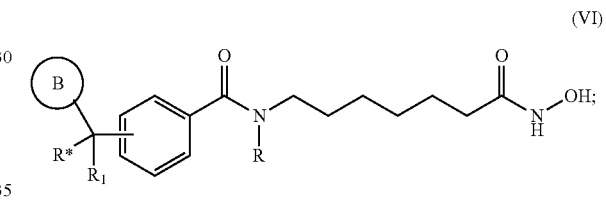

(VI)

or a pharmaceutically acceptable salt, ester or prodrug thereof,
wherein,
ring B is an optionally substituted aryl or an optionally substituted heteroaryl;
R* is an optionally substituted alkyl, an optionally substituted aryl or an optionally substituted heteroaryl;
R$_1$ is H, alkyl, aryl, arylalkyl, heteroaryl, heterocyclic, carbocyclic, OH, alkoxy, NH$_2$, NH(alkyl), or N(alkyl)(alkyl);
or R* and R$_1$ together with the atom to which each is attached, may form an optionally substituted carbocyclic, optionally substituted heterocyclic, optionally substituted aryl or optionally substituted heteroaryl ring; and
R is H or an optionally substituted alkyl.

In one embodiment, ring B is phenyl, pyridinyl, pyrimidinyl, pyrazinyl, or thiazole; each of which may be optionally substituted.

In another embodiment, R* is methyl, trifluoromethyl, phenyl, pyridinyl, pyrimidinyl, pyrazinyl, or thiazole; each of which may be optionally substituted.

In certain embodiments, R$_1$ is OH, methoxy, or ethoxy.

In various embodiments, ring B and R* are each independently substituted with one or more of alkyl, halogen, or C(O)NR$_X$R$_Y$, wherein R$_X$ is H or alkyl, and R$_Y$ is H or alkyl.

In other embodiments, ring B and R* are each independently substituted with one or more of methyl, F, or C(O)N(Me)$_2$.

Representative compounds of the invention include, but are not limited to, the following compounds of Table 1 below.

TABLE 1
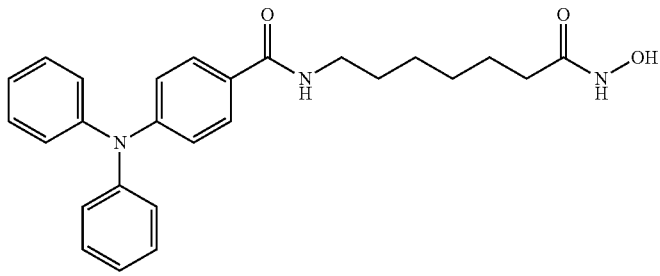
4-(diphenylamino)-N-(7-(hydroxyamino)-7-oxoheptyl)benzamide
IC$_{50}$(nM) HDAC6 = 18 HDAC3 = 316
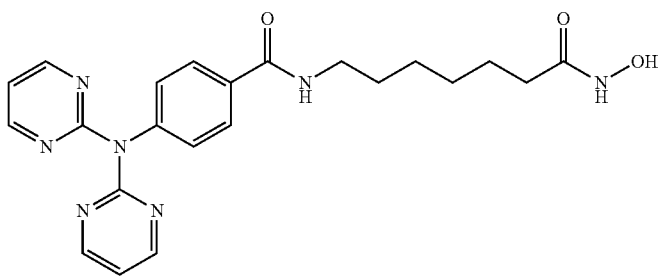
4-(dipyrimidin-2-ylamino)-N-(7-(hydroxyamino)-7-oxoheptyl)benzamide
IC$_{50}$(nM) HDAC6 = 174 HDAC3 = 1089
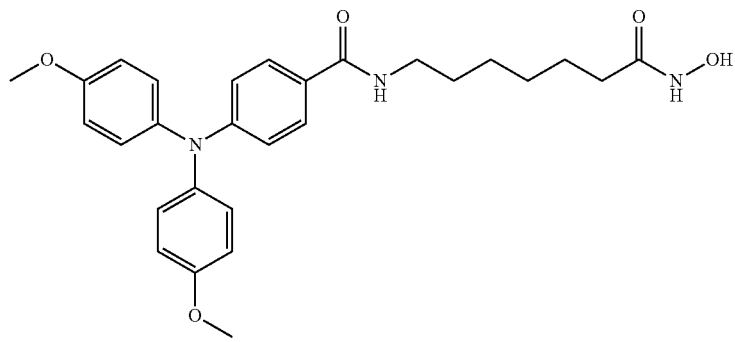
4-(bis(4-methoxyphenyl)amino)-N-(7-(hydroxyamino)-7-oxoheptyl)benzamide
IC$_{50}$(nM) HDAC6 = 200 HDAC3 = 2001
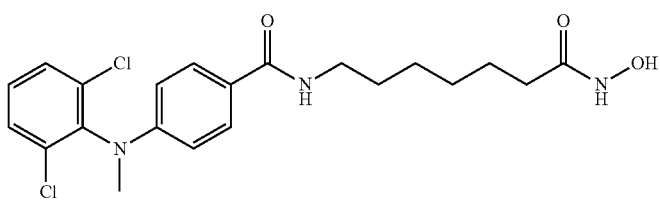
4-((2,6-dichlorophenyl)(methyl)amino)-N-(7-(hydroxyamino)-7-oxoheptyl)benzamide
IC$_{50}$(nM) HDAC6 = 3 HDAC3 = 29

TABLE 1-continued

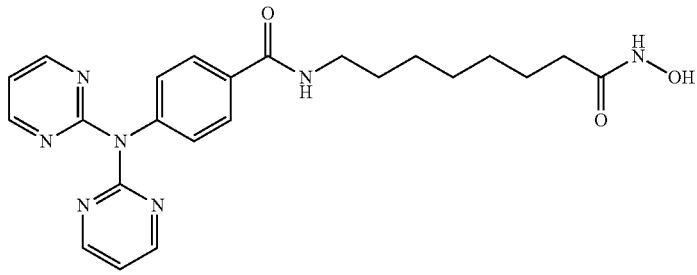

4-(dipyrimidin-2-ylamino)-N-(8-(hydroxyamino)-8-oxooctyl)benzamide
IC$_{50}$(nM) HDAC6 = 110 HDAC3 = 208

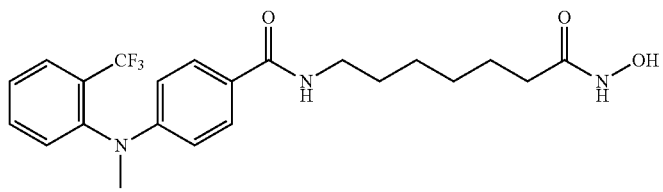

N-(7-(hydroxyamino)-7-oxoheptyl)-4-(methyl(2-
(trifluoromethyl)phenyl)amino)benzamide
IC$_{50}$(nM) HDAC6 = 3 HDAC3 = 36

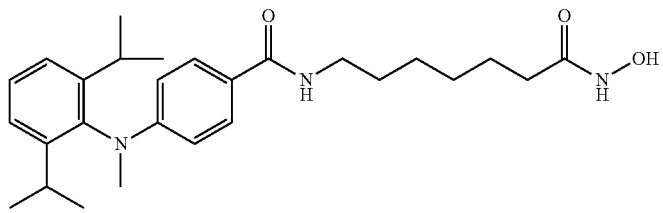

4-((2,6-diisopropylphenyl)(methyl)amino)-N-(7-(hydroxyamino)-7-
oxoheptyl)benzamide
IC$_{50}$(nM) HDAC6 = 45 HDAC3 = 1074

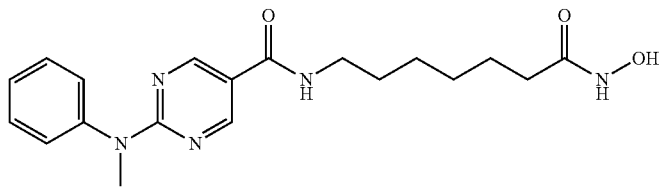

N-(7-(hydroxyamino)-7-oxoheptyl)-2-(methyl(phenyl)amino)pyrimidine-
5-carboxamide
IC$_{50}$(nM) HDAC6 = 6 HDAC3 = 47

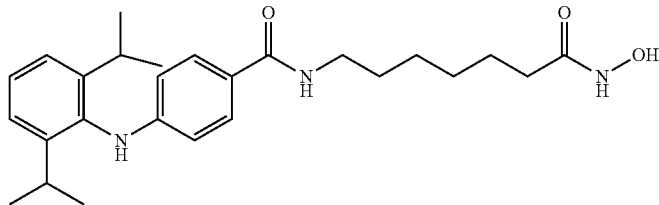

4-(2,5-diisopropylphenylamino)-N-(7-(hydroxyamino)-7-oxoheptyl)benzamide
IC$_{50}$(nM) HDAC6 = 20 HDAC3 = 369

TABLE 1-continued

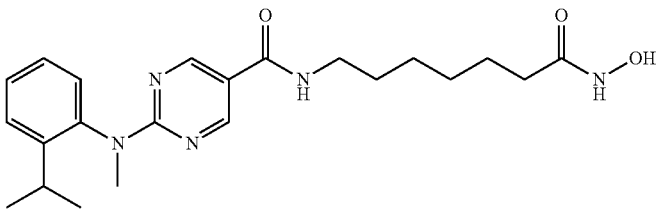

N-(7-(hydroxyamino)-7-oxoheptyl)-2-((2-isopropylphenyl)(methyl)amino)pyrimidine-5-carboxamide
IC$_{50}$(nM) HDAC6 = 7 HDAC3 = 73

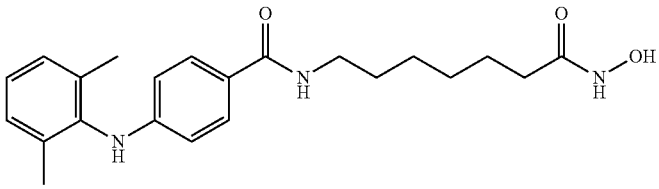

4-(2,6-dimethylphenylamino)-N-(7-(hydroxyamino)-7-oxoheptyl)benzamide
IC$_{50}$(nM) HDAC6 = 3 HDAC3 = 59

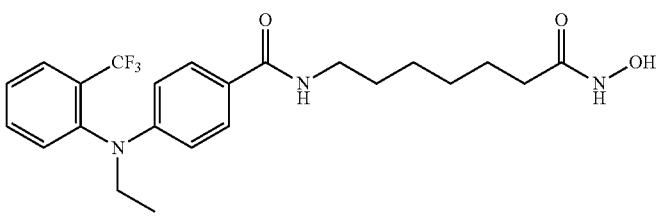

4-(ethyl(2-(trifluoromethyl)phenyl)amino)-N-(7-(hydroxyamino)-7-oxoheptyl) benzamide
IC$_{50}$(nM) HDAC6 = 5 HDAC3 = 46

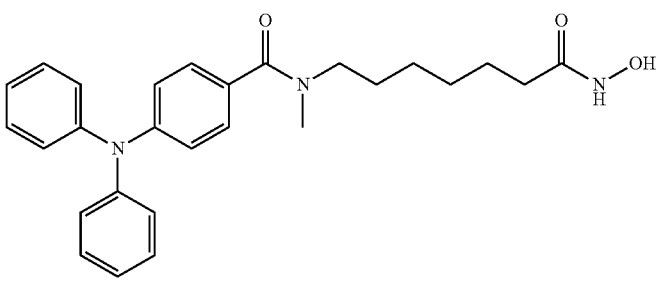

4-(diphenylamino)-N-(7-(hydroxyamino)-7-oxoheptyl)-N-methylbenzamide
IC$_{50}$(nM) HDAC6 = 82 HDAC3 = 313

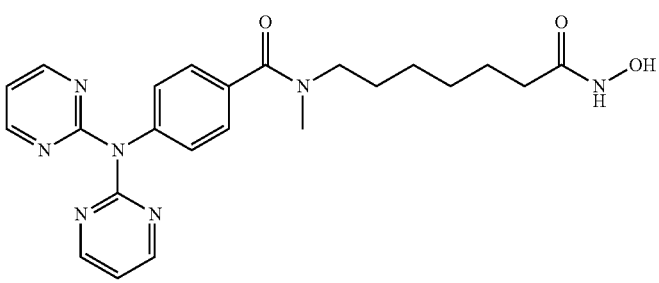

4-(dipyrimidin-2-ylamino)-N-(7-(hydroxyamino)-7-oxoheptyl)-N-methylbenzamide
IC$_{50}$(nM) HDAC6 = 198 HDAC3 = 1237

TABLE 1-continued

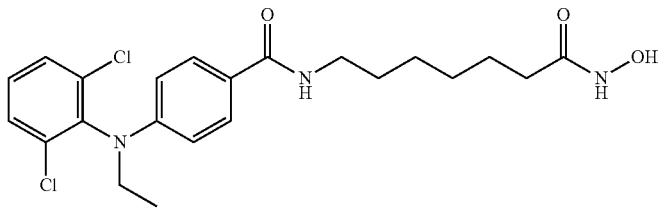

4-((2,6-dichlorophenyl)(ethyl)amino)-N-(7-(hydroxyamino)-7-oxoheptyl)benzamide
IC$_{50}$(nM) HDAC6 = 8 HDAC3 = 71

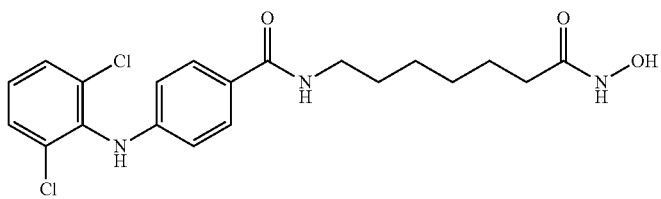

4-(2,6-dichlorophenylamino)-N-(7-(hydroxyamino)-7-oxoheptyl)benzamide
IC$_{50}$(nM) HDAC6 = 3 HDAC3 = 28

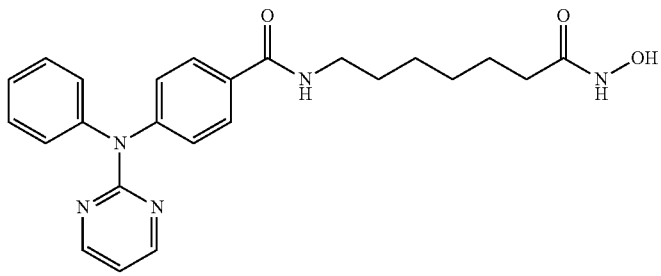

N-(7-(hydroxyamino)-7-oxoheptyl)-4-(phenyl(pyrimidin-2-yl)amino)benzamide
IC$_{50}$(nM) HDAC6 = 3 HDAC3 = 65

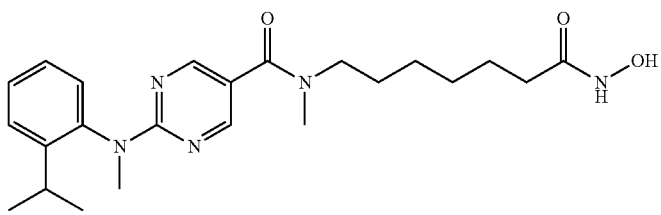

N-(7-(hydroxyamino)-7-oxoheptyl)-2-((2-isopropylphenyl)(methyl)amino)-N-methylpyrimidine-5-carboxamide
IC$_{50}$(nM) HDAC6 = 50 HDAC3 = 642

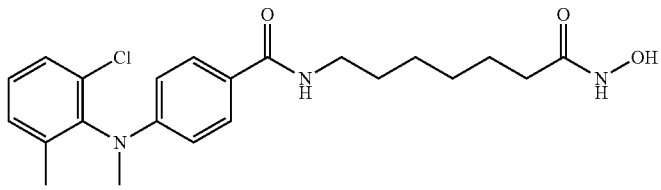

4-((2-chloro-6-methylphenyl)(methyl) amino)-N-(7-(hydroxyamino)-7-oxoheptyl) benzamide
IC$_{50}$(nM) HDAC6 = 4 HDAC3 = 58

TABLE 1-continued

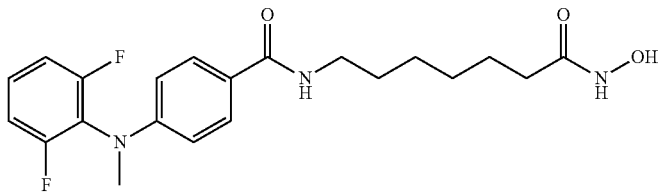

4-((2,6-difluorophenyl)(methyl)amino)-N-(7-(hydroxyamino)-7-oxoheptyl) benzamide
IC$_{50}$(nM) HDAC6 = 2 HDAC3 = 17

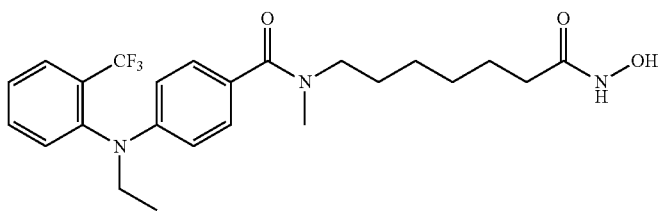

4-(ethyl(2-(trifluoromethyl)phenyl)amino)-N-(7-(hydroxyamino)-7-
oxoheptyl)-N-methylbenzamide
IC$_{50}$(nM) HDAC6 = 39 HDAC3 = 58

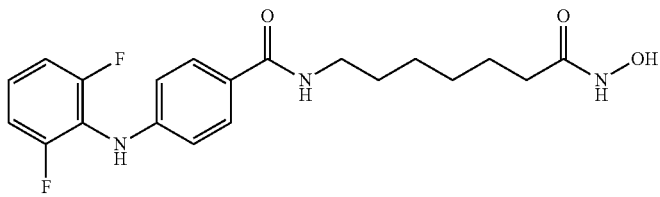

4-(2,6-difluorophenylamino)-N-(7-(hydroxyamino)-7-oxoheptyl)benzamide
IC$_{50}$(nM) HDAC6 = 3 HDAC3 = 25

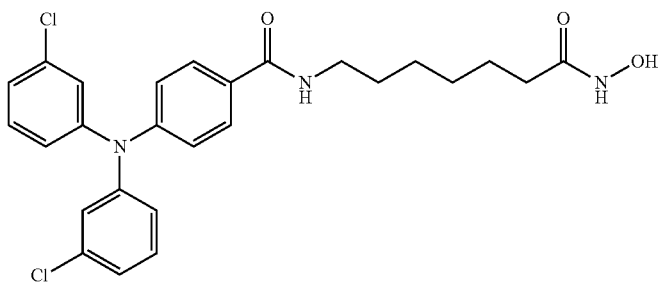

4-(bis(3-chlorophenyl)amino)-N-(7-(hydroxyamino)-7-oxoheptyl)benzamide
IC$_{50}$(nM) HDAC6 = 858 HDAC3 = 11813

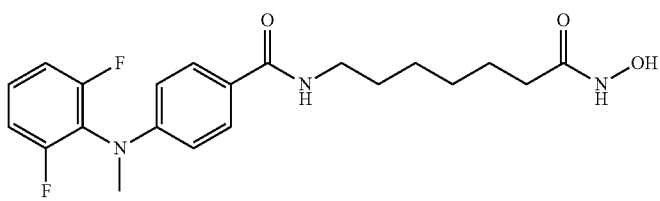

7-(4-((2,6-difluorophenyl)(methyl)amino)benzylamino)-N-hydroxy heptanamide
IC$_{50}$(nM) HDAC6 = 121 HDAC3 = 67

TABLE 1-continued

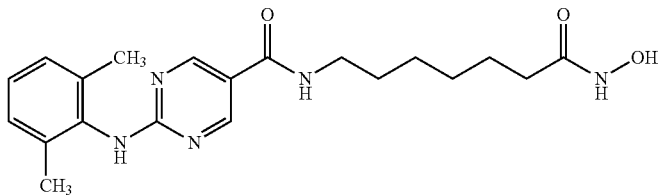

2-(2,6-dimethylphenylamino)-N-(7-(hydroxyamino)-7-oxoheptyl)pyrimidine-
5-carboxamide
IC$_{50}$(nM) HDAC6 = 33 HDAC3 505

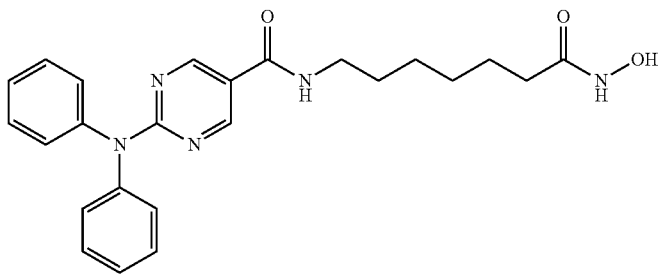

2-(diphenylamino)-N-(7-(hydroxyamino)-7-oxoheptyl)pyrimidine-5-carboxamide
IC$_{50}$(nM) HDAC6 = 10 HDAC3 = 84

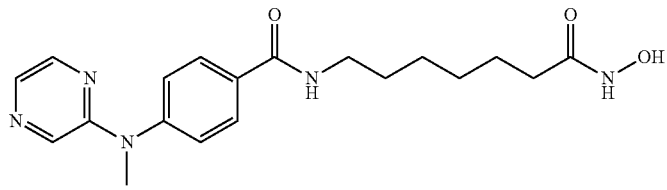

N-(7-(hydroxyamino)-7-oxoheptyl)-4-(methyl(pyrazin-2-yl)amino)benzamide
IC$_{50}$(nM) HDAC6 = 21 HDAC3 = 93

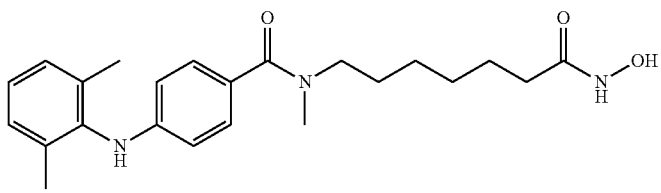

4-(2,6-dimethylphenylamino)-N-(7-(hydroxyamino)-7-oxoheptyl)-N-methylbenzamide
IC$_{50}$(nM) HDAC6 = 7 HDAC3 = 304

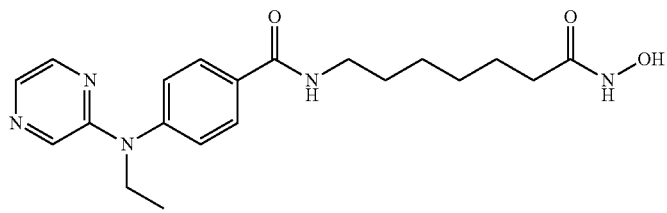

4-(ethyl(pyrazin-2-yl)amino)-N-(7-(hydroxyamino)-7-oxoheptyl)benzamide
IC$_{50}$(nM) HDAC6 = 11 HDAC3 = 93

TABLE 1-continued

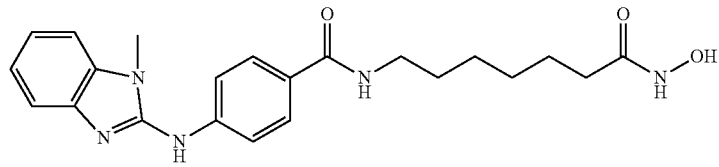

N-(7-(hydroxyamino)-7-oxoheptyl)-4-(1-methyl-1H-benzo[d]imidazol-2-ylamino)benzamide
IC$_{50}$(nM) HDAC6 = 9 HDAC3 = 57

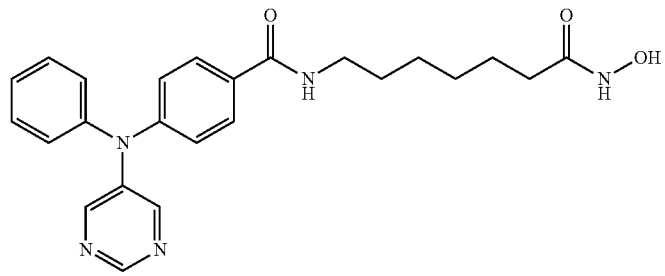

N-(7-(hydroxyamino)-7-oxoheptyl)-4-(phenyl(pyrimidin-5-yl)amino)benzamide
IC$_{50}$(nM) HDAC6 = 12 HDAC3 = 92

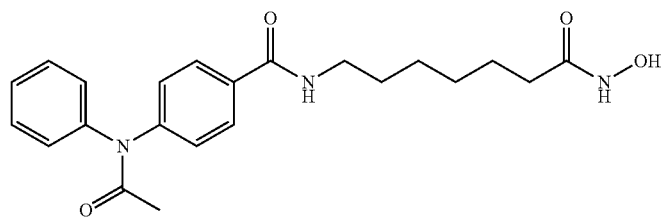

N-(7-(hydroxyamino)-7-oxoheptyl)-4-(N-phenylacetamido)benzamide
IC$_{50}$(nM) HDAC6 = 3 HDAC3 = 67

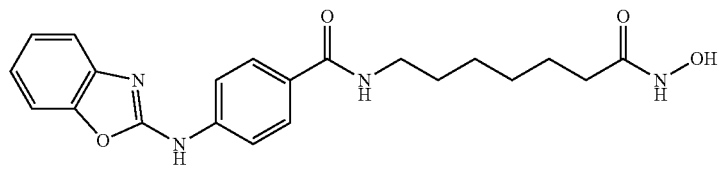

4-(benzo[d]oxazol-2-ylamino)-N-(7-(hydroxyamino)-7-oxoheptyl)benzamide
IC$_{50}$(nM) HDAC6 = 3 HDAC3 = 22

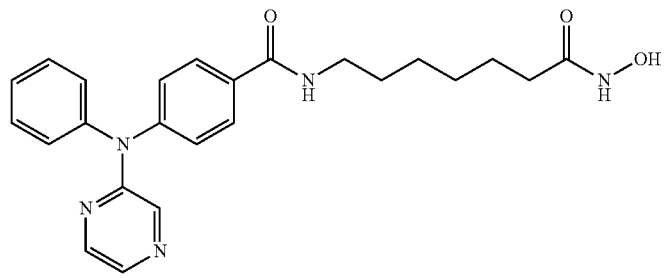

N-(7-(hydroxyamino)-7-oxoheptyl)-4-(phenyl(pyrazin-2-yl)amino)benzamide
IC$_{50}$(nM) HDAC6 = 14 HDAC3 = 64

TABLE 1-continued

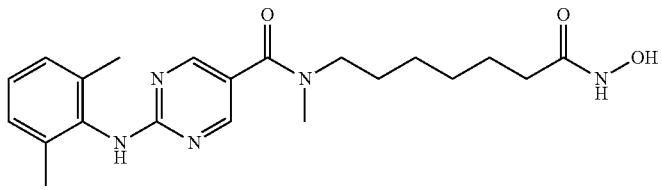

2-(2,6-dimethylphenylamino)-N-(7-(hydroxyamino)-7-oxoheptyl)-N-
methylpyrimidine-5-carboxamide
IC$_{50}$(nM) HDAC6 = 33 HDAC3 = 387

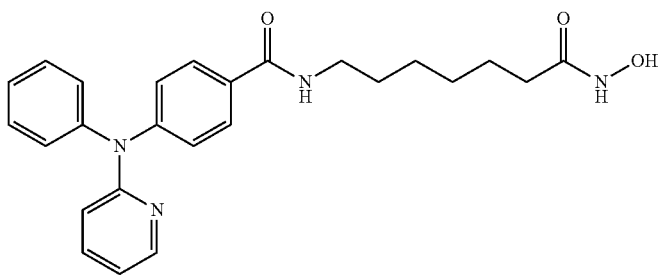

N-(7-(hydroxyamino)-7-oxoheptyl)-4-(phenyl(pyridin-2-yl)amino)benzamide
IC$_{50}$(nM) HDAC6 = 14 HDAC3 = 61

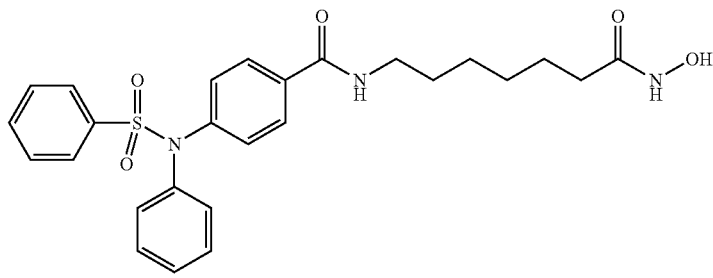

N-(7-(hydroxyamino)-7-oxoheptyl)-4-(N-phenylphenylsulfonamido)benzamide
IC$_{50}$(nM) HDAC6 = 15 HDAC3 = 84

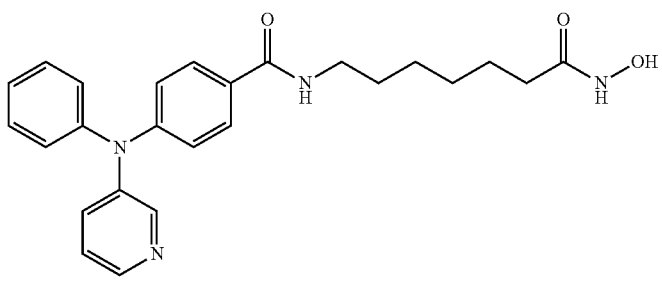

N-(7-(hydroxyamino)-7-oxoheptyl)-4-(phenyl(pyridin-3-yl)amino)benzamide
IC$_{50}$(nM) HDAC6 = 21 HDAC3 = 66

TABLE 1-continued

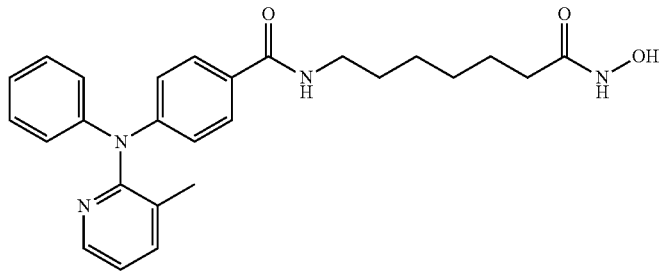

N-(7-(hydroxyamino)-7-oxoheptyl)-4-((3-methylpyridin-2-
yl)(phenyl)amino) benzamide
IC$_{50}$(nM) HDAC6 = 20 HDAC3 = 69

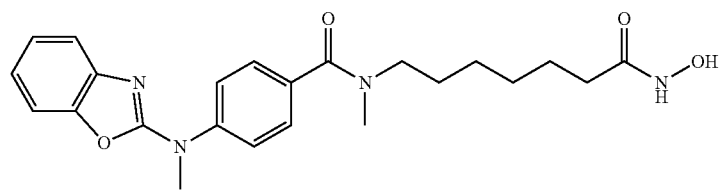

4-(benzo[d]oxazol-2-yl(methyl)amino)-N-(7-(hydroxyamino)-7-
oxoheptyl)-N-methylbenzamide
IC$_{50}$(nM) HDAC6 = 107 HDAC3 = 294

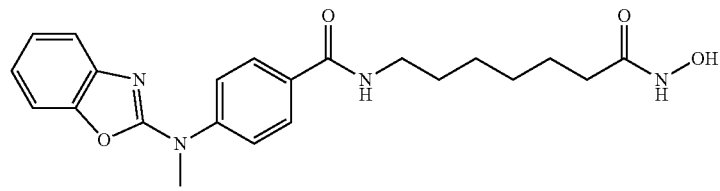

4-(benzo[d]oxazol-2-yl(methyl)amino)-N-(7-(hydroxyamino)-7-oxoheptyl)benzamide
IC$_{50}$(nM) HDAC6 = 11 HDAC3 = 83

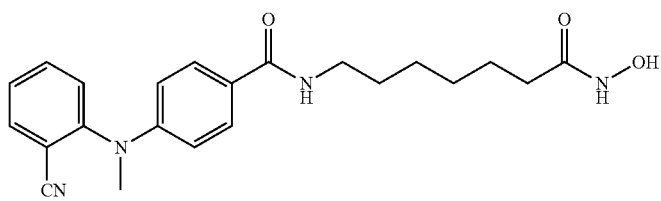

4-((2-cyanophenyl)(methyl)amino)-N-(7-(hydroxyamino)-7-oxoheptyl)benzamide
IC$_{50}$(nM) HDAC6 = 4 HDAC3 = 23

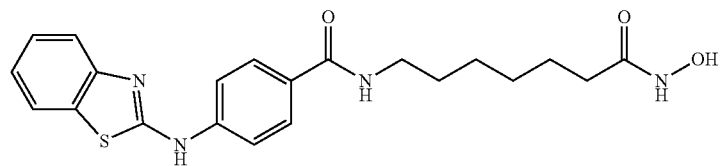

4-(benzo[d]thiazol-2-ylamino)-N-(7-(hydroxyamino)-7-oxoheptyl)benzamide
IC$_{50}$(nM) HDAC6 = 12 HDAC3 = 22

TABLE 1-continued

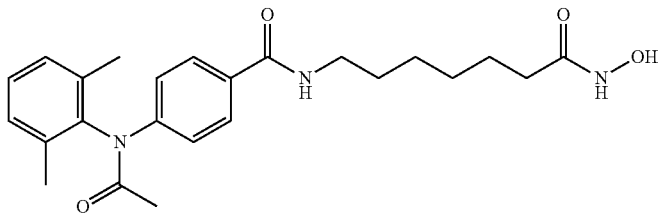

4-(N-(2,6-dimethylphenyl)acetamido)-N-(7-(hydroxyamino)-7-oxoheptyl) benzamide
IC$_{50}$(nM) HDAC6 = 22 HDAC3 = 198

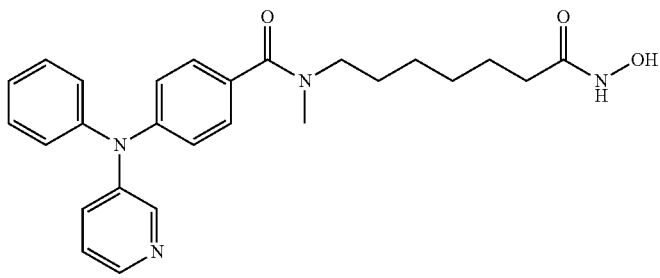

N-(7-(hydroxyamino)-7-oxoheptyl)-N-methyl-4-(phenyl(pyridin-3-yl)amino) benzamide
IC50(nM) HDAC6 = 64 HDAC3 = 85

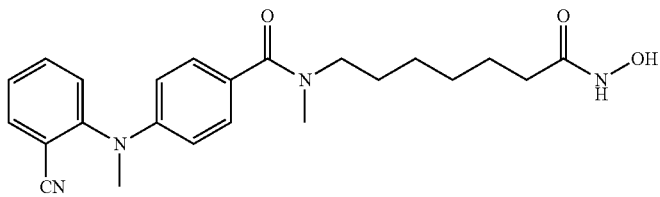

4-((2-cyanophenyl)(methyl)amino)-N-(7-(hydroxyamino)-7-oxoheptyl)-N-methylbenzamide
IC$_{50}$(nM) HDAC6 = 35 HDAC3 = 135

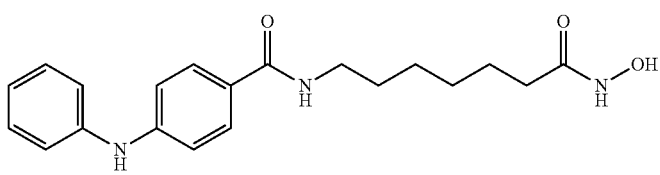

N-(7-(hydroxyamino)-7-oxoheptyl)-4-(phenylamino)benzamide
IC$_{50}$(nM) HDAC6 = 7 HDAC3 = 16

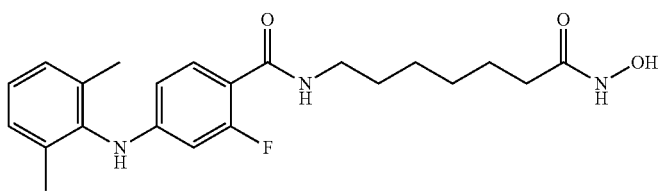

4-(2,6-dimethylphenylamino)-2-fluoro-N-(7-(hydroxyamino)-7-oxoheptyl) benzamide
IC$_{50}$(nM) HDAC6 = 3 HDAC3 = 95

TABLE 1-continued

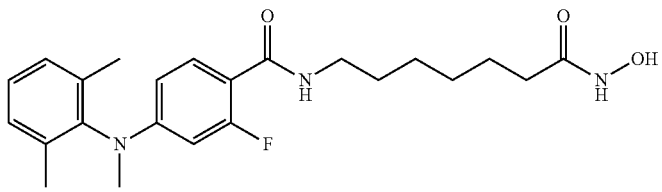

4-((2,6-dimethylphenyl)(methyl)amino)-2-fluoro-N-(7-
(hydroxyamino)-7-oxoheptyl)benzamide
IC$_{50}$(nM) HDAC6 = 5 HDAC3 = 107

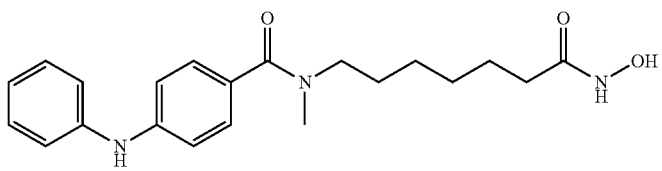

N-(7-(hydroxyamino)-7-oxoheptyl)-N-methyl-4-(phenylamino)benzamide
IC$_{50}$(nM) HDAC6 = 11 HDAC3 = 50

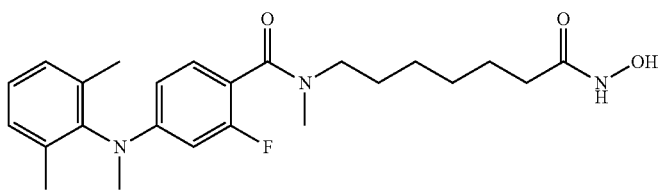

4-((2,6-dimethylphenyl)(methyl)amino)-2-fluoro-N-(7-(hydroxyamino)-7-
oxoheptyl)-N-methylbenzamide
IC$_{50}$(nM) HDAC6 = 9 HDAC3 = 148

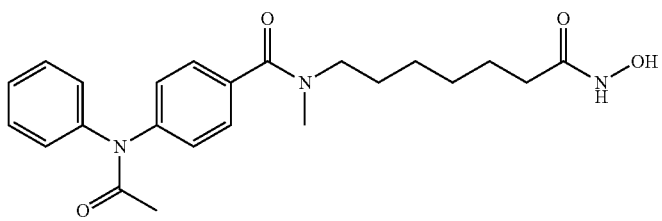

N-(7-(hydroxyamino)-7-oxoheptyl)-N-methyl-4-(N-phenylacetamido)benzamide
IC$_{50}$(nM) HDAC6 = 37 HDAC3 = 493

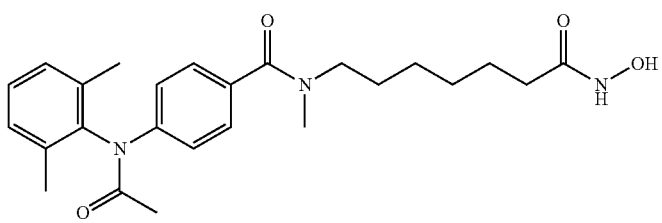

4-(N-(2,6-dimethylphenyl)acetamido-N-(7-(hydroxyamino)-7-
oxoheptyl)-N-methylbenzamide
IC$_{50}$(nM) HDAC6 = 25 HDAC3 = 528

TABLE 1-continued

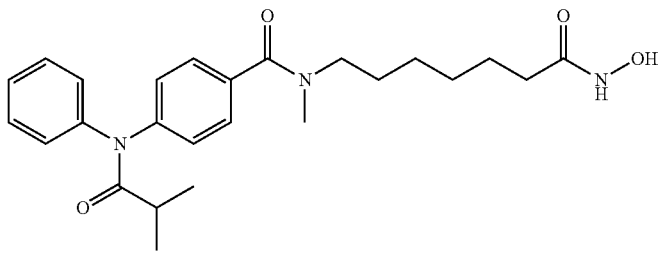

N-(7-(hydroxyamino)-7-oxoheptyl)-N-methyl-4-(N-phenylisobutyramido)benzamide
IC$_{50}$(nM) HDAC6 = 67 HDAC3 = 533

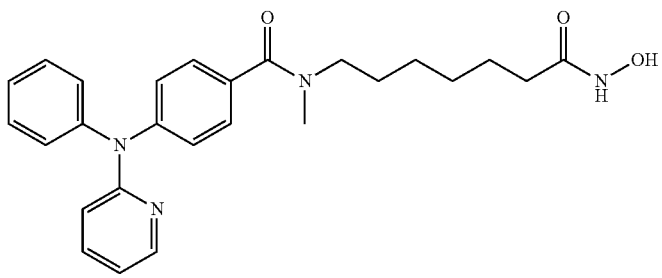

N-(7-(hydroxyamino)-7-oxoheptyl)-N-methyl-4-(phenyl(pyridin-2-yl)amino) benzamide
IC$_{50}$(nM) HDAC6 = 15 HDAC3 = 100

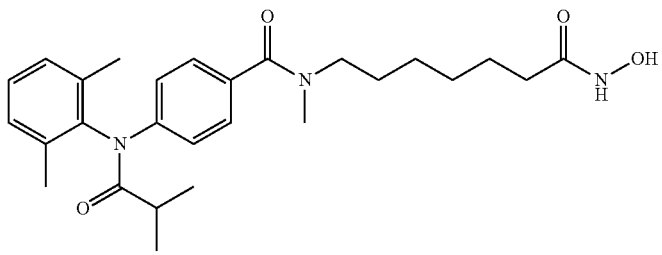

4-(N-(2,6-dimethylphenyl)isobutyramido)-N-(7-(hydroxyamino)-7-oxoheptyl)-N-methylbenzamide
IC$_{50}$(nM) HDAC6 = 37 HDAC3 = 386

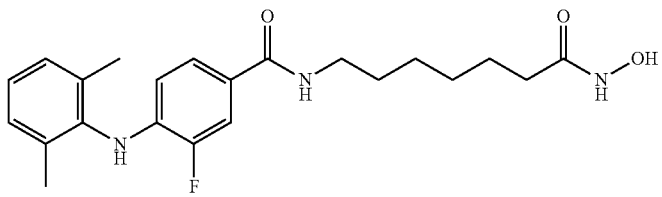

4-(2,6-dimethylphenylamino)-3-fluoro-N-(7-(hydroxyamino)-7-oxoheptyl)benzamide
IC$_{50}$(nM) HDAC6 = 4 HDAC3 = 80

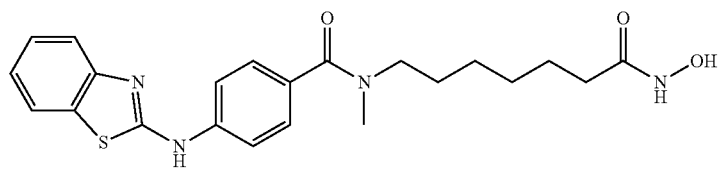

4-(benzo[d]thiazol-2-ylamino)-N-(7-(hydroxyamino)-7-oxoheptyl)-N-methylbenzamide
IC$_{50}$(nM) HDAC6 = 20 HDAC3 = 43

TABLE 1-continued

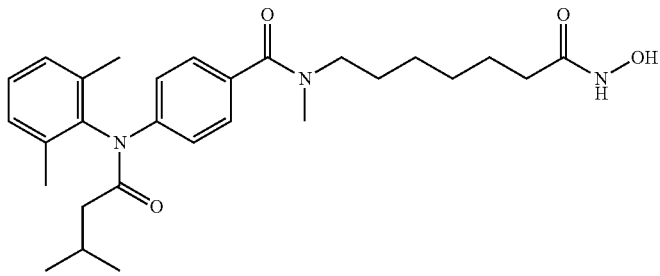

4-(N-(2,6-dimethylphenyl)-3-methylbutanamido)-N-(7-(hydroxyamino)-7-oxoheptyl)-N-methylbenzamide
IC$_{50}$(nM) HDAC6 = 66 HDAC3 = 558

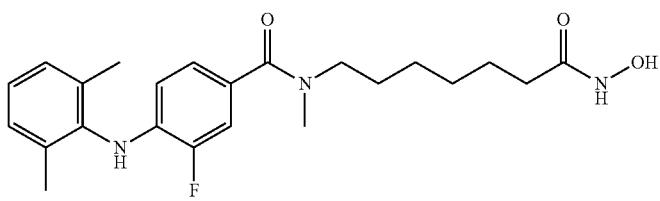

4-(2,6-dimethylphenylamino)-3-fluoro-N-(7-(hydroxyamino)-7-oxoheptyl)-N-methylbenzamide
IC$_{50}$(nM) HDAC6 = 12 HDAC3 = 204

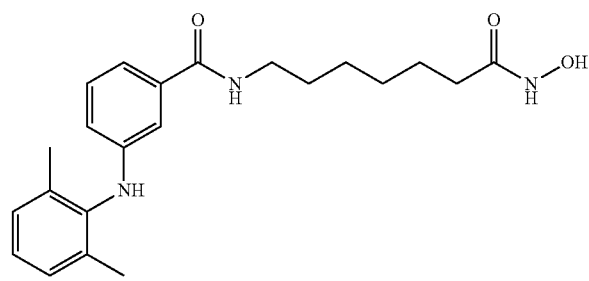

3-(2,6-dimethylphenylamino)-N-(7-(hydroxyamino)-7-oxoheptyl)benzamide
IC$_{50}$(nM) HDAC6 = 10 HDAC3 = 54

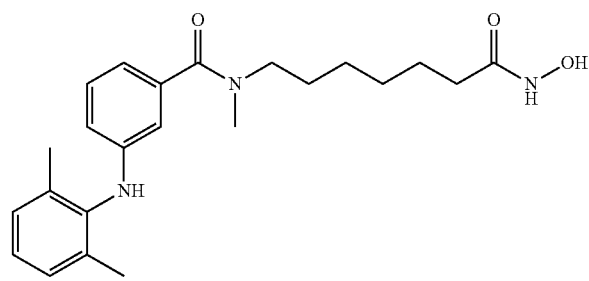

3-(2,6-dimethylphenylamino)-N-(7-(hydroxyamino)-7-oxoheptyl)-N-methylbenzamide
IC$_{50}$(nM) HDAC6 = 27 HDAC3 = 186

TABLE 1-continued

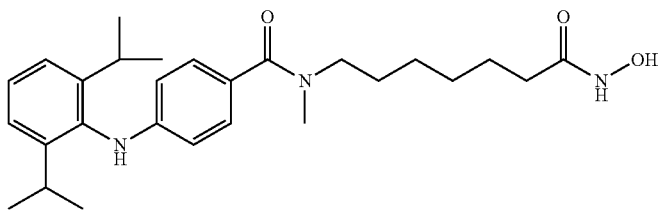

4-(2,6-diisopropylphenylamino)-N-(7-(hydroxyamino)-7-oxoheptyl)-
N-methylbenzamide
IC$_{50}$(nM) HDAC6 = 109 HDAC3 = 925

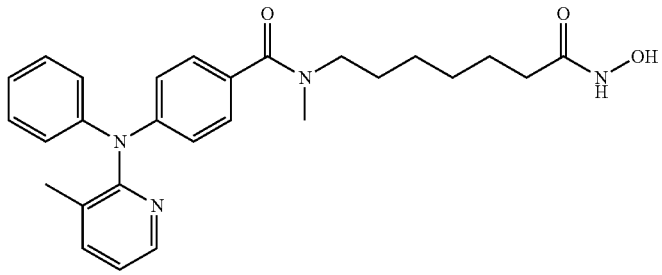

N-(7-(hydroxyamino)-7-oxoheptyl)-N-methyl-4-((3-methylpyridin-2-yl)(phenyl)
amino)benzamide
IC$_{50}$(nM) HDAC6 = 27 HDAC3 = 186

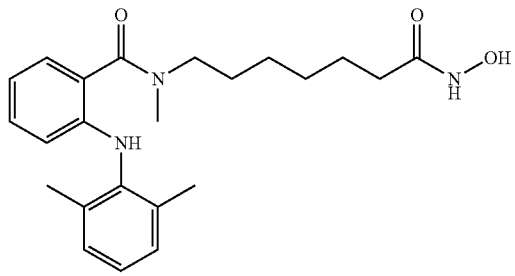

2-(2,6-dimethylphenylamino)-N-(7-(hydroxyamino)-7-oxoheptyl)-
N-methylbenzamide
IC$_{50}$(nM) HDAC6 = 48 HDAC3 = 242

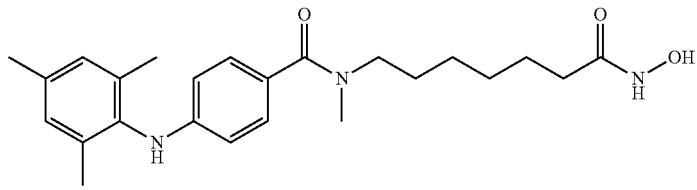

N-(7-(hydroxyamino)-7-oxoheptyl)-4-(mesitylamino)-N-methylbenzamide
IC$_{50}$(nM) HDAC6 = 35 HDAC3 = 347

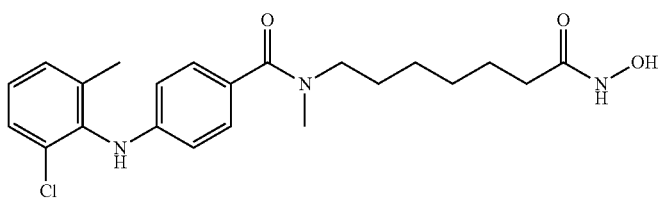

4-(2-chloro-6-methylphenylamino)-N-(7-(hydroxyamino)-7-oxoheptyl)-
N-methylbenzamide
IC$_{50}$(nM) HDAC6 = 11 HDAC3 = 132

TABLE 1-continued

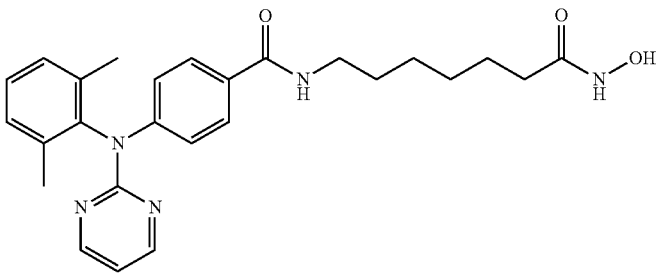

4-((2,6-dimethylphenyl)(pyrimidin-2-yl)amino)-N-(7-(hydroxyamino)-7-
oxoheptyl)benzamide
IC$_{50}$(nM) HDAC6 = 4 HDAC3 = 85

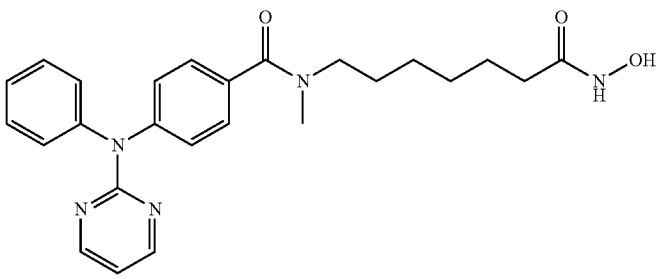

N-(7-(hydroxyamino)-7-oxoheptyl)-N-methyl-4-(phenyl(pyrimidin-
2-yl)amino)benzamide
IC$_{50}$(nM) HDAC6 = 18 HDAC3 = 170

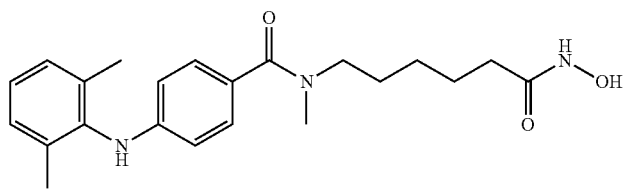

4-(2,6-dimethylphenylamino)-N-(6-(hydroxyamino)-6-oxohexyl)-
N-methylbenzamide
IC$_{50}$(nM) HDAC6 = 46 HDAC3 = 304

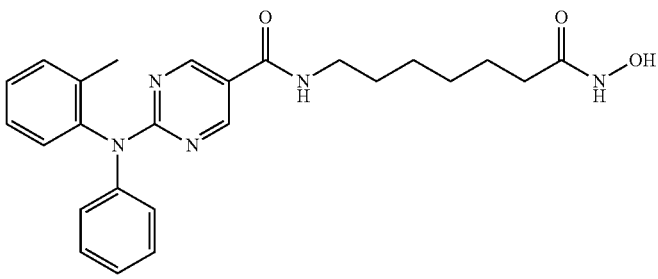

N-(7-(hydroxyamino)-7-oxoheptyl)-2-(phenyl(o-tolyl)amino)pyrimidine-
5-carboxamide
IC$_{50}$(nM) HDAC6 = 9 HDAC3 = 144

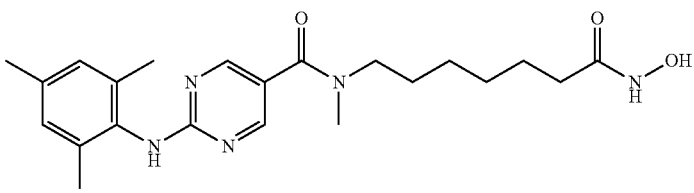

N-(7-(hydroxyamino)-7-oxoheptyl)-2-(mesitylamino)-N-methylpyrimidine-5-carboxamide
IC$_{50}$(nM) HDAC6 = 38 HDAC3 = 478

TABLE 1-continued

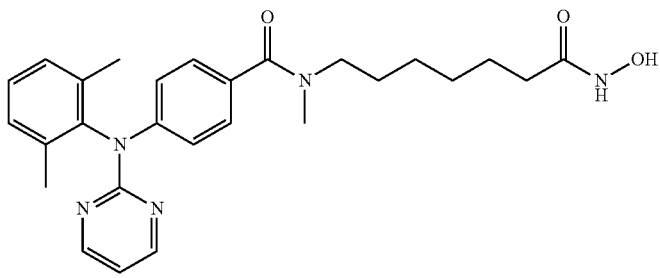

4-((2,6-dimethylphenyl)(pyrimidin-2-yl)amino)-N-(7-(hydroxyamino)-7-oxoheptyl)-
N-methylbenzamide
IC$_{50}$(nM) HDAC6 = 24 HDAC3 = 297

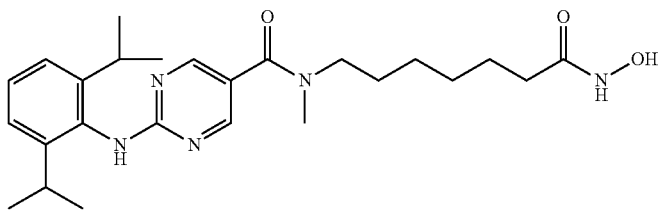

2-(2,6-diisopropylphenylamino)-N-(7-(hydroxyamino)-7-oxoheptyl)-N-
methylpyrimidine-5-carboxamide
IC$_{50}$(nM) HDAC6 = 51 HDAC3 = 421

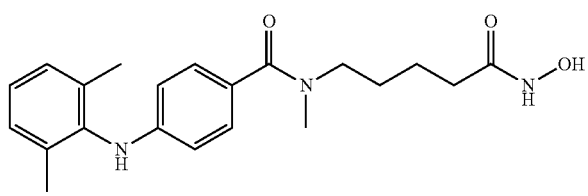

4-(2,6-dimethylphenylamino)-N-(5-(hydroxyamino)-5-oxopentyl)-N-
methylbenzamide
IC$_{50}$(nM) HDAC6 = 363 HDAC3 = 2066

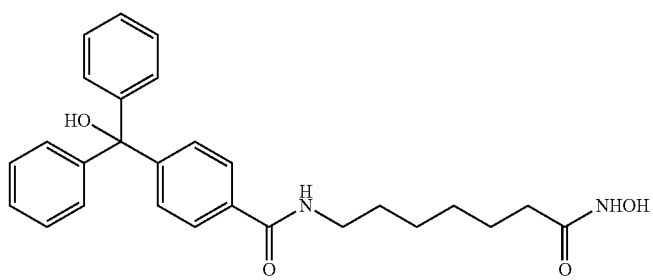

N-(7-(hydroxyamino)-7-oxoheptyl)-4-(hydroxydiphenylmethyl)benzamide
IC$_{50}$(nM) HDAC6 = 10 HDAC3 = 160

TABLE 1-continued
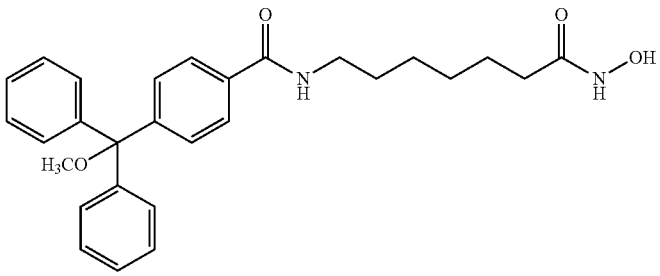
N-(7-(hydroxyamino)-7-oxoheptyl)-4-(methoxydiphenylmethyl)benzamide
IC$_{50}$(nM) HDAC6 = 7 HDAC3 = 243
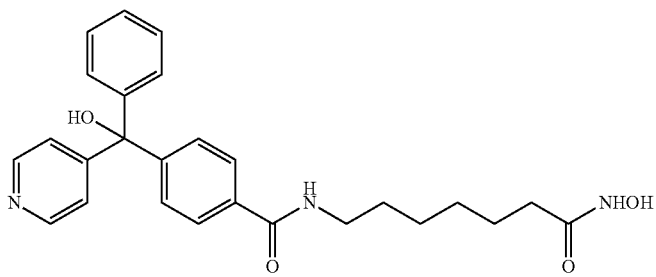
4-(hydroxy(phenyl)(pyridin-4-yl)methyl)-N-(7-(hydroxyamino)-
7-oxoheptyl) benzamide
IC$_{50}$(nM) HDAC6 = 4 HDAC3 = 78
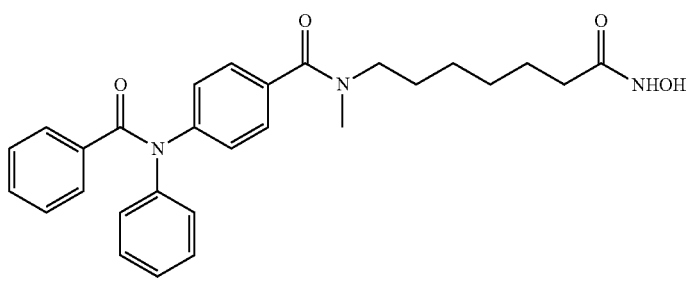
N-(7-(hydroxyamino)-7-oxoheptyl)-N-methyl-4-(N-phenylbenzamido)benzamide
IC$_{50}$(nM) HDAC6 = 27 HDAC3 = 378
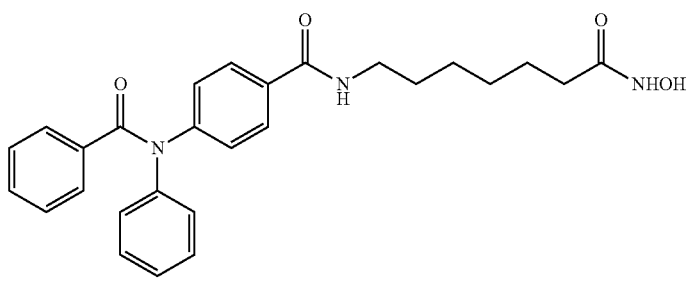
N-(4-(7-(hydroxyamino)-7-oxoheptylcarbamoyl)phenyl)-N-phenylbenzamide
IC$_{50}$(nM) HDAC6 = 2 HDAC3 = 67

TABLE 1-continued

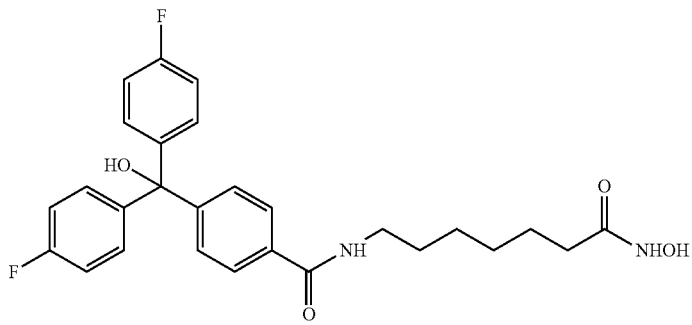

4-(bis(4-fluorophenyl)(hydroxy)methyl)-N-(7-(hydroxyamino)-7-oxoheptyl)benzamide
IC$_{50}$(nM) HDAC6 = 3 HDAC3 = 121

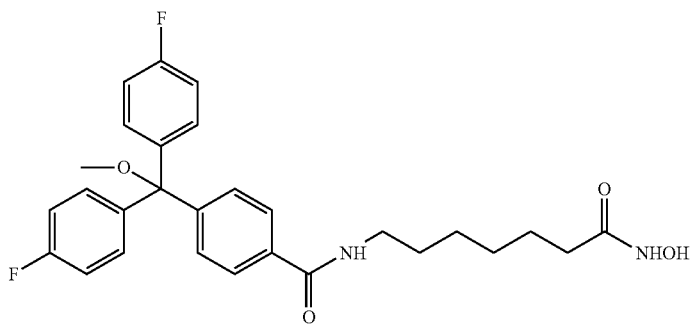

4-(bis(4-fluorophenyl)(methoxy)methyl)-N-(7-(hydroxyamino)-7-oxoheptyl) benzamide
IC$_{50}$(nM) HDAC6 = 13 HDAC3 = 1225

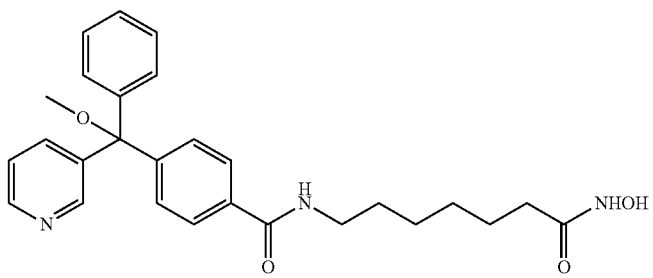

N-(7-(hydroxyamino)-7-oxoheptyl)-4-(methoxy(phenyl)(pyridin-3-yl)methyl)benzamide
IC$_{50}$(nM) HDAC6 = 3 HDAC3 = 73

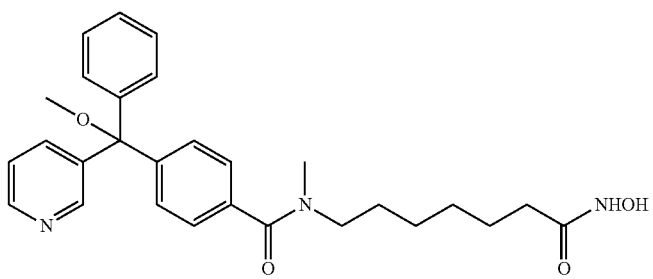

N-(7-(hydroxyamino)-7-oxoheptyl)-4-(methoxy(phenyl)(pyridin-3-yl)methyl)-N-methylbenzamide
IC$_{50}$(nM) HDAC6 = 19 HDAC3 = 319

TABLE 1-continued

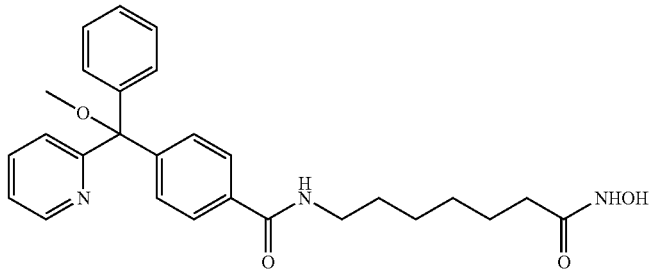

N-(7-(hydroxyamino)-7-oxoheptyl)-4-(methoxy(phenyl)(pyridin-2-yl)methyl)benzamide
IC$_{50}$(nM) HDAC6 = 3   HDAC3 = 130

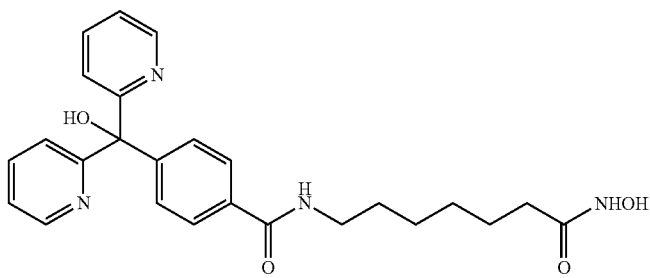

N-(7-(hydroxyamino)-7-oxoheptyl)-4-(hydroxydipyridin-2-ylmethyl)benzamide
IC$_{50}$(nM) HDAC6 = 4   HDAC3 = 123

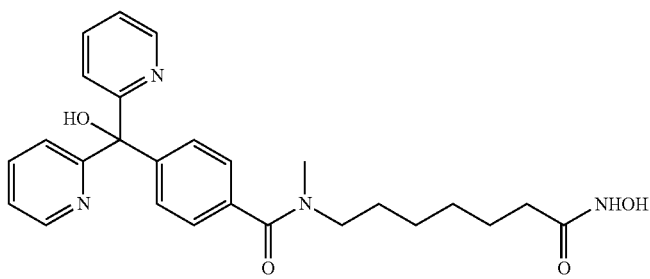

N-(7-(hydroxyamino)-7-oxoheptyl)-4-(hydroxydipyridin-2-ylmethyl)-N-methyl benzamide
IC$_{50}$(nM) HDAC6 = 36   HDAC3 = 550

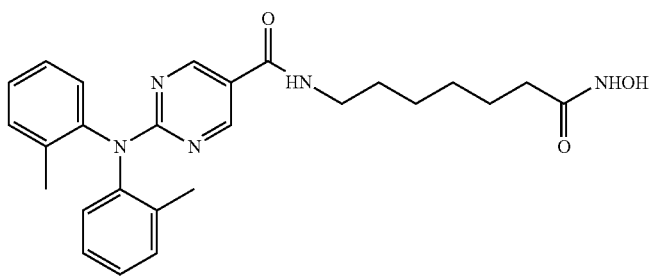

2-(di-o-tolylamino)-N-(7-(hydroxyamino)-7-oxoheptyl)pyrimidine-5-carboxamide
IC$_{50}$(nM) HDAC6 = 9   HDAC3 = 138

TABLE 1-continued

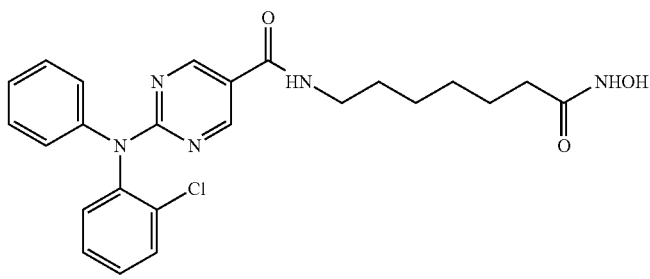

2-((2-chlorophenyl)(phenyl)amino)-N-(7-(hydroxyamino)-7-oxoheptyl)pyrimidine-5-carboxamide
IC$_{50}$(nM) HDAC6 = 4 HDAC3 = 76

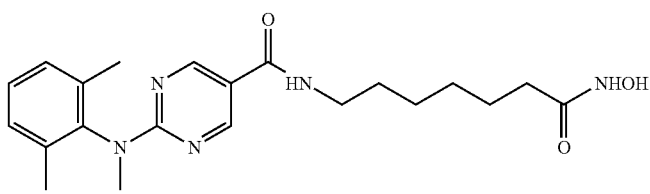

2-((2,6-dimethylphenyl)(phenyl)amino)-N-(7-(hydroxyamino)-7-oxoheptyl)pyrimidine-5-carboxamide
IC$_{50}$(nM) HDAC6 = 5 HDAC3 = 137

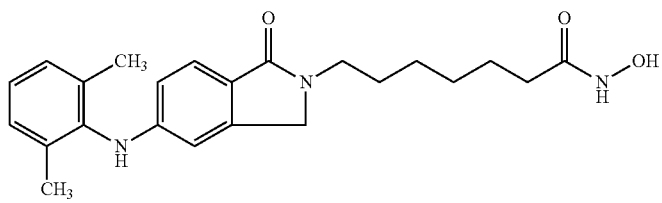

7-(5-(2,6-dimethylphenylamino)-1-oxoisoindolin-2-yl)-N-hydroxyheptanamide
IC$_{50}$(nM) HDAC6 = 3 HDAC3 = 37

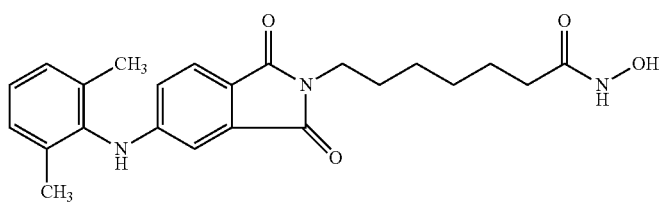

7-(5-(2,6-dimethylphenylamino)-1,3-dioxoisoindolin-2-yl)-N-hydroxyheptanamide
IC$_{50}$(nM) HDAC6 = TBD HDAC3 = TBD

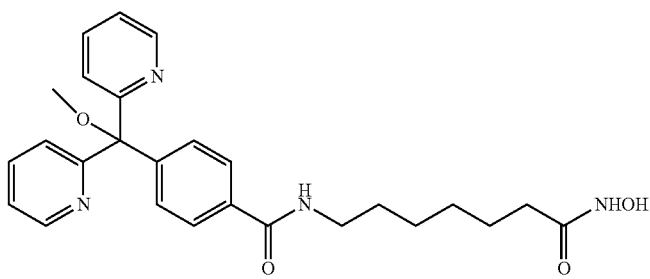

N-(7-(hydroxyamino)-7-oxoheptyl)-4-(methoxydipyridin-2-ylmethyl)benzamide
IC$_{50}$(nM) HDAC6 = TBD HDAC3 = TBD TABLE 1-continued

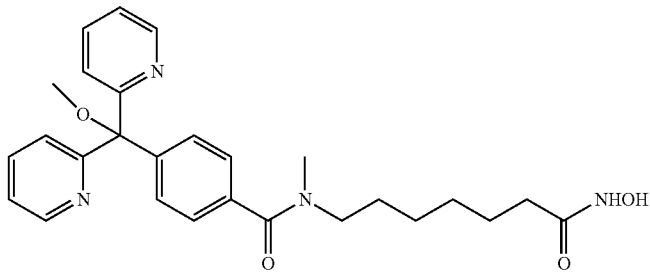

N-(7-(hydroxyamino)-7-oxoheptyl)-4-(methoxydipyridin-2-ylmethyl)-N-
methylbenzamide
IC$_{50}$(nM) HDAC6 = TBD HDAC3 = TBD

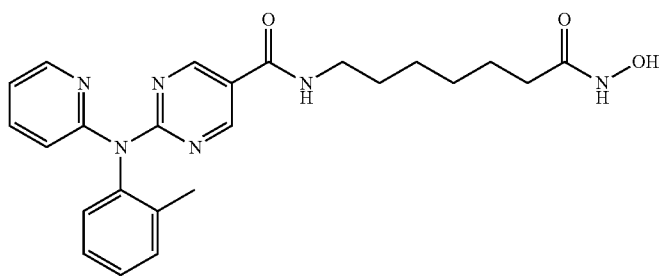

N-(7-(hydroxyamino)-7-oxoheptyl)-2-(pyridin-2-yl(o-tolyl)amino)pyrimidine-
5-carboxamide
IC$_{50}$(nM) HDAC6 = TBD HDAC3 = TBD

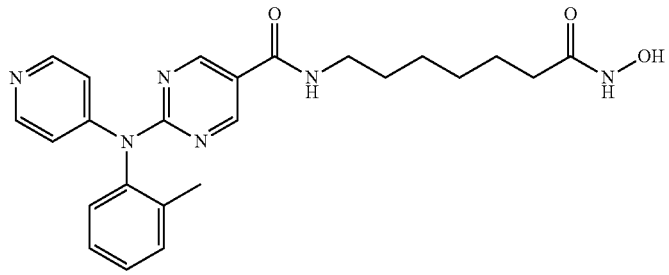

N-(7-(hydroxyamino)-7-oxoheptyl)-2-(pyridin-4-yl(o-tolyl)amino)pyrimidine-
5-carboxamide
IC$_{50}$(nM) HDAC6 = TBD HDAC3 = TBD

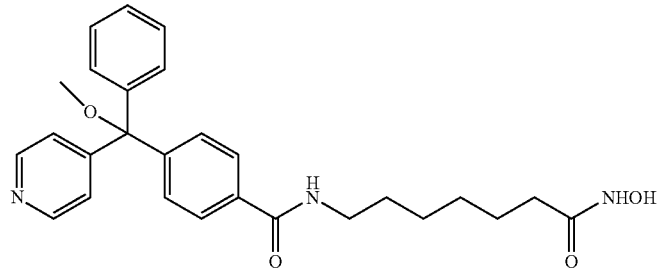

N-(7-(hydroxyamino)-7-oxoheptyl)-4-(methoxy(phenyl)(pyridin-4-
yl)methyl)benzamide
IC$_{50}$(nM) HDAC6 = 3 HDAC3 = 78

TABLE 1-continued
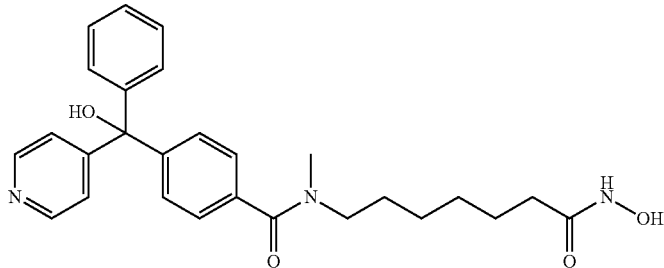
4-(hydroxy(phenyl)(pyridin-4-yl)methyl)-N-(7-(hydroxyamino)-7-oxoheptyl)-
N-methylbenzamide
IC$_{50}$(nM) HDAC6 = 18 HDAC3 = 221
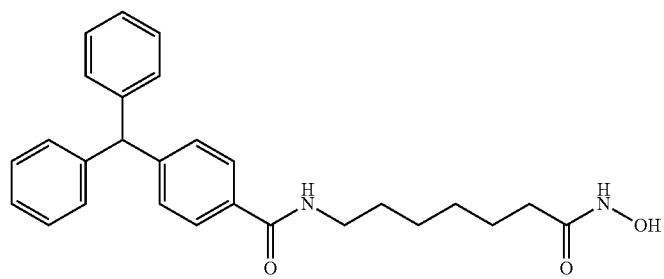
4-benzhydryl-N-(7-(hydroxyamino)-7-oxoheptyl)benzamide
IC$_{50}$(nM) HDAC6 = 22 HDAC3 = 370
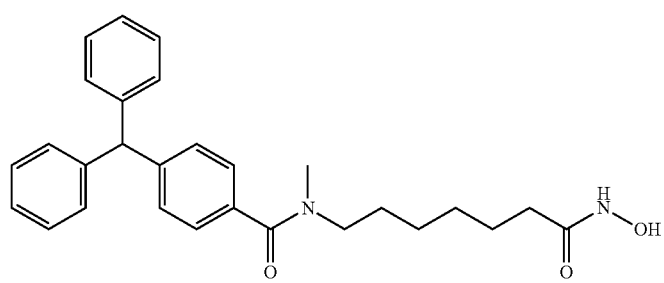
4-benzhydryl-N-(7-(hydroxyamino)-7-oxoheptyl)-N-methylbenzamide
IC$_{50}$(nM) HDAC6 = 47 HDAC3 = 544
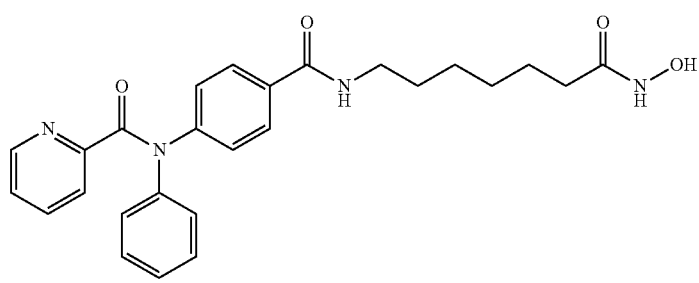
N-(4-(7-(hydroxyamino)-7-oxoheptylcarbamoyl)phenyl)-N-phenylpicolinamide
IC$_{50}$(nM) HDAC6 = 5 HDAC3 = 68

TABLE 1-continued

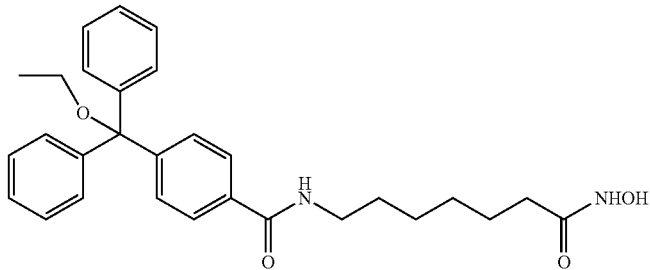

4-(ethoxydiphenylmethyl)-N-(7-(hydroxyamino)-7-oxoheptyl)benzamide
IC$_{50}$(nM) HDAC6 = 13 HDAC3 = 705

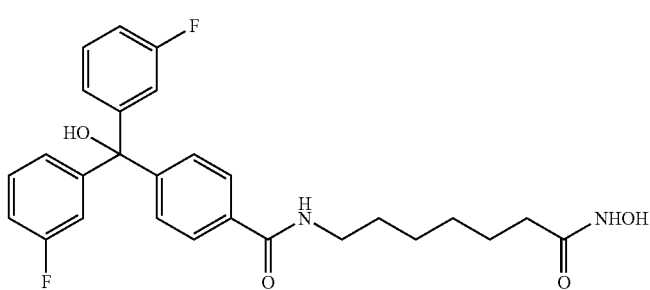

4-(bis(3-fluorophenyl)(hydroxy)methyl)-N-(7-(hydroxyamino)-
7-oxoheptyl)benzamide
IC$_{50}$(nM) HDAC6 = 5 HDAC3 = 186

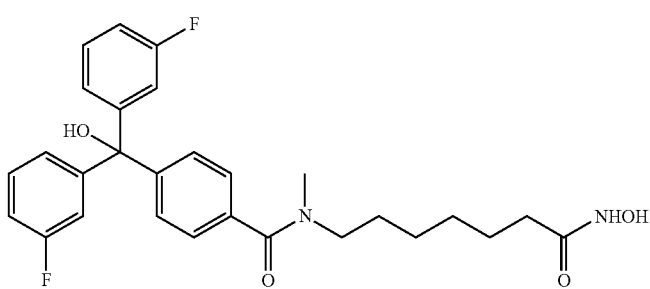

4-(bis(3-fluorophenyl)(hydroxy)methyl)-N-(7-(hydroxyamino)-7-oxoheptyl)-
N-methylbenzamide
IC$_{50}$(nM) HDAC6 = 10 HDAC3 = 319

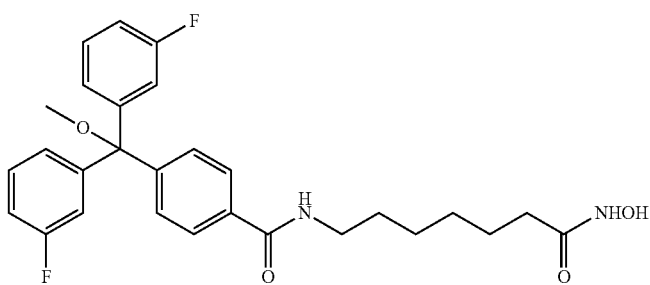

4-(bis(3-fluorophenyl)(methoxy)methyl)-N-(7-(hydroxyamino)-7-
oxoheptyl)benzamide
IC$_{50}$(nM) HDAC6 = 15 HDAC3 = 1261

TABLE 1-continued

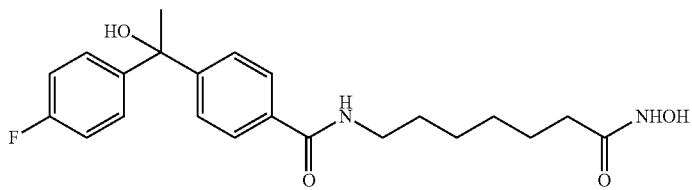

4-(1-(4-fluorophenyl)-1-hydroxyethyl)-N-(7-(hydroxyamino)-7-oxoheptyl)benzamide
IC$_{50}$(nM) HDAC6 = 3 HDAC3 = 42

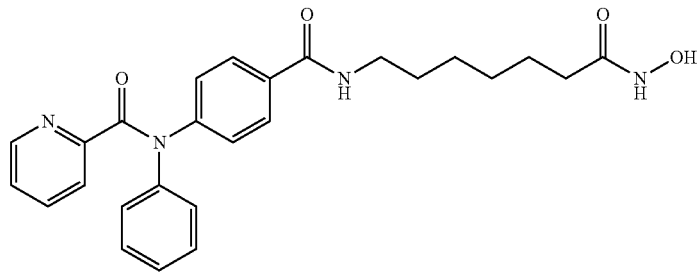

N-(4-(7-(hydroxyamino)-7-oxoheptylcarbamoyl)phenyl)-N-phenylpicolinamide
IC$_{50}$(nM) HDAC6 = 5 HDAC3 = 68

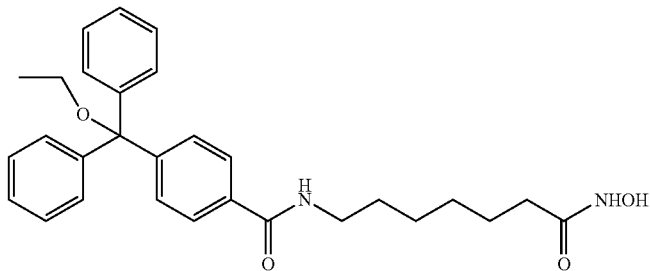

4-(ethoxydiphenylmethyl)-N-(7-(hydroxyamino)-7-oxoheptyl)benzamide
IC$_{50}$(nM) HDAC6 = 13 HDAC3 = 705

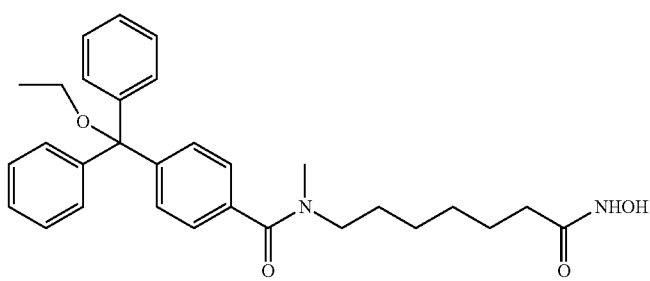

4-(ethoxydiphenylmethyl)-N-(7-(hydroxyamino)-7-oxoheptyl)-N-methylbenzamide
IC$_{50}$(nM) HDAC6 = 36 HDAC3 = 899

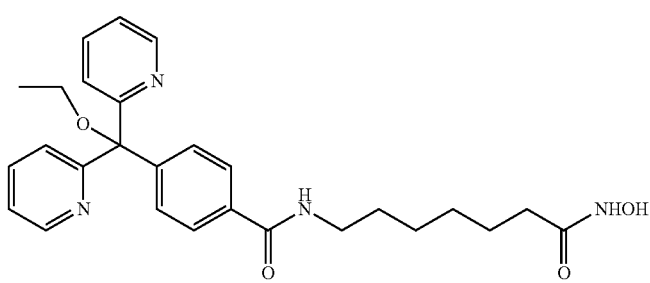

4-(ethoxydipyridin-2-ylmethyl)-N-(7-(hydroxyamino)-7-oxoheptyl)benzamide
IC$_{50}$(nM) HDAC6 = 6 HDAC3 = 138

TABLE 1-continued

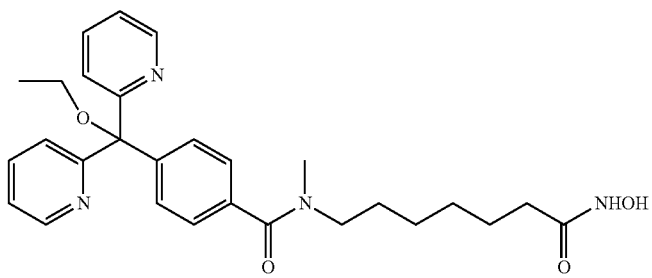

4-(ethoxydipyridin-2-ylmethyl)-N-(7-(hydroxyamino)-7-oxoheptyl)-
N-methylbenzamide
IC$_{50}$(nM) HDAC6 = 45 HDAC3 = 443

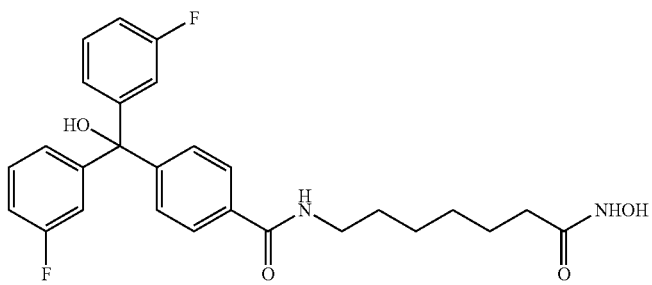

4-(bis(3-fluorophenyl)(hydroxy)methyl)-N-(7-(hydroxyamino)-7-
oxoheptyl)benzamide
IC$_{50}$(nM) HDAC6 = 5 HDAC3 = 186

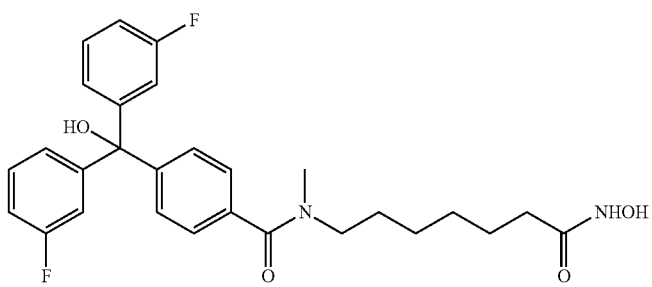

4-(bis(3-fluorophenyl)(hydroxy)methyl)-N-(7-(hydroxyamino)-7-oxoheptyl)-
N-methyl benzamide IC$_{50}$(nM) HDAC6 = 10 HDAC3 = 319

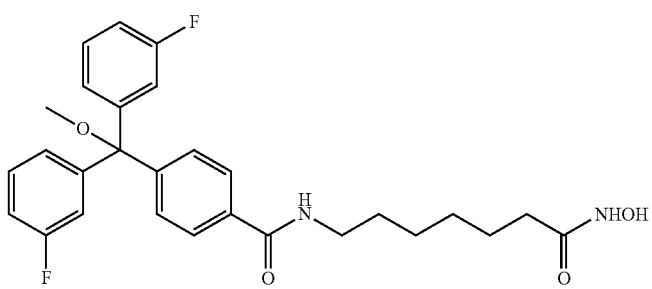

4-(bis(3-fluorophenyl)(methoxy)methyl)-N-(7-(hydroxyamino)-7-
oxoheptyl)benzamide IC$_{50}$(nM) HDAC6 = 15 HDAC3 = 1281

TABLE 1-continued

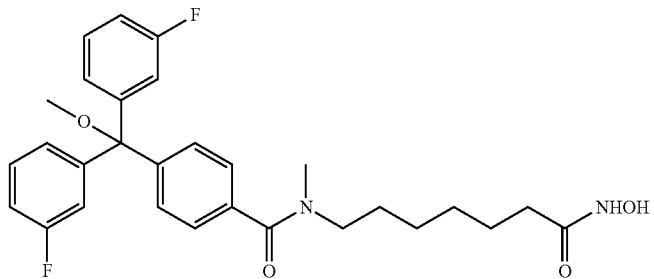

4-(bis(3-fluorophenyl)(methoxy)methyl)-N-(7-(hydroxyamino)-7-
oxoheptyl)-N-methylbenzamide
IC$_{50}$(nM) HDAC6 = 47 HDAC3 = 805

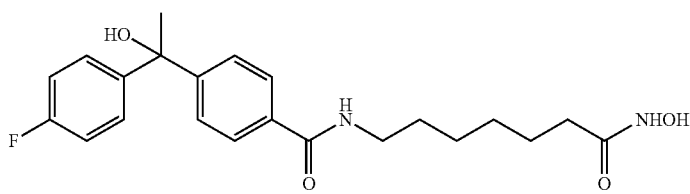

4-(1-(4-fluorophenyl)-1-hydroxyethyl)-N-(7-(hydroxyamino)-7-oxoheptyl)benzamide
IC$_{50}$(nM) HDAC6 = 3 HDAC3 = 42

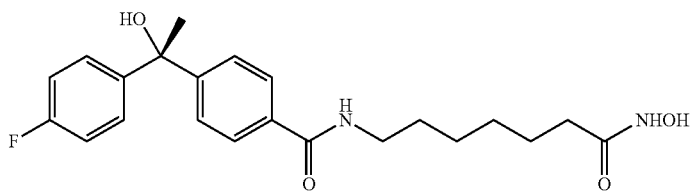

4-(1-(4-fluorophenyl)-1-hydroxyethyl)-N-(7-(hydroxyamino)-7-oxoheptyl)benzamide
IC$_{50}$(nM) HDAC6 = 3 HDAC3 = 30

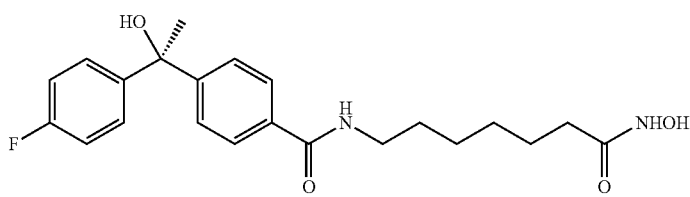

4-(1-(4-fluorophenyl)-1-hydroxyethyl)-N-(7-(hydroxyamino)-7-oxoheptyl)benzamide
IC$_{50}$(nM) HDAC6 = 3 HDAC3 = 37

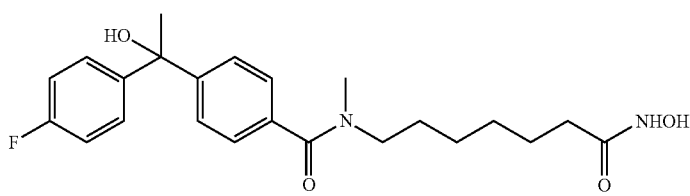

4-(1-(4-fluorophenyl)-1-hydroxyethyl)-N-(7-(hydroxyamino)-7-oxoheptyl)-N-
methylbenzamide
IC$_{50}$(nM) HDAC6 = 23 HDAC3 = 243

TABLE 1-continued

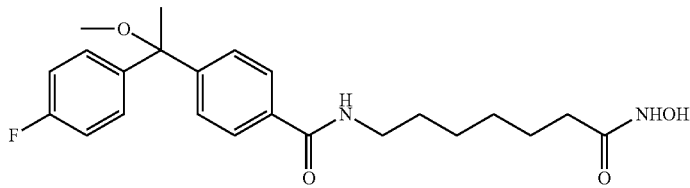

4-(1-(4-fluorophenyl)-1-methoxyethyl)-N-(7-(hydroxyamino)-7-oxoheptyl)benzamide
IC$_{50}$(nM) HDAC6 = 3  HDAC3 = 28

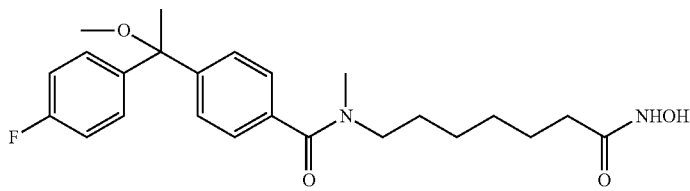

4-(1-(4-fluorophenyl)-1-methoxyethyl)-N-(7-(hydroxyamino)-7-oxoheptyl)-
N-methylbenzamide
IC$_{50}$(nM) HDAC6 = 17  HDAC3 = 187

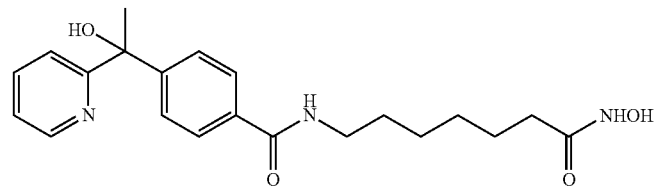

4-(1-hydroxy-1-(pyridin-2-yl)ethyl)-N-(7-(hydroxyamino)-7-oxoheptyl)benzamide
IC$_{50}$(nM) HDAC6 = 7  HDAC3 = 134

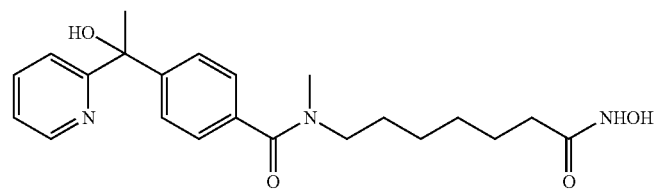

4-(1-hydroxy-1-(pyridin-2-yl)ethyl)-N-(7-(hydroxyamino)-7-
oxoheptyl)-N-methylbenzamide
IC$_{50}$(nM) HDAC6 = 36  HDAC3 = 501

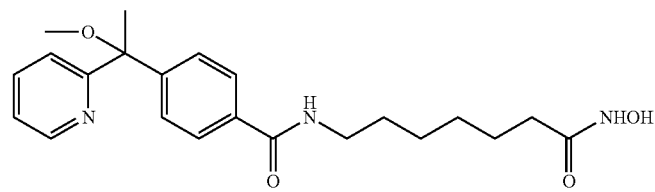

N-(7-(hydroxyamino)-7-oxoheptyl)-4-(1-methoxy-1-(pyridin-2-yl)ethyl)benzamide
IC$_{50}$(nM) HDA6 = 4  HDAC3 = 53

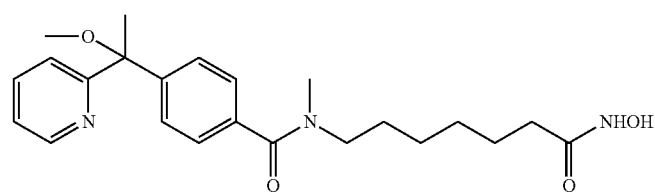

N-(7-(hydroxyamino)-7-oxoheptyl)-4-(1-methoxy-1-(pyridin-2-yl)ethyl)-
N-methylbenzamide
IC$_{50}$(nM) HDAC6 = 42  HDAC3 = 433

TABLE 1-continued

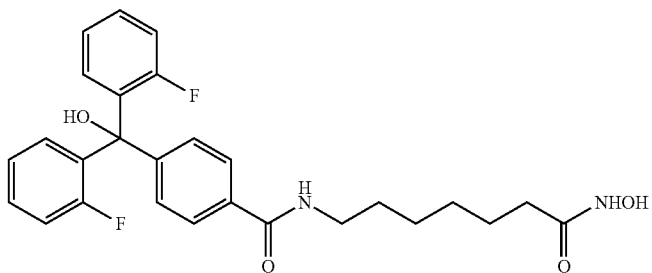

4-(bis(2-fluorophenyl)(hydroxy)methyl)-N-(7-(hydroxyamino)-7-
oxoheptyl)benzamide
IC$_{50}$(nM) HDAC6 = 3 HDAC3 = 74

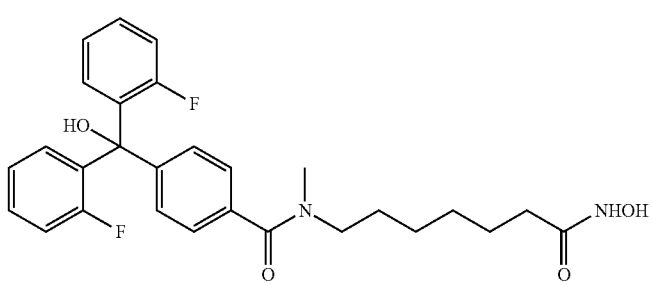

4-(bis(2-fluorophenyl)(hydroxy)methyl)-N-(7-(hydroxyamino)-7-oxoheptyl)-
N-methylbenzamide
IC$_{50}$(nM) HDAC6 = 9 HDAC3 = 132

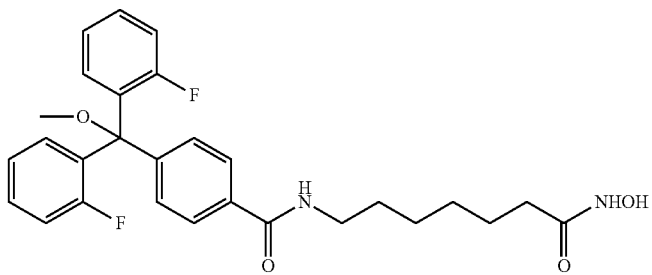

4-(bis(2-fluorophenyl)(methoxy)methyl)-N-(7-(hydroxyamino)-7-
oxoheptyl)benzamide
IC$_{50}$(nM) HDAC6 = 6 HDAC3 = 184

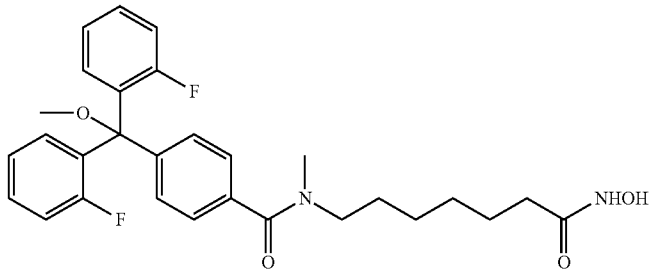

4-(bis(2-fluorophenyl)(methoxy)methyl)-N-(7-(hydroxyamino)-
7-oxoheptyl)-N-methylbenzamide
IC$_{50}$(nM) HDAC6 = 17 HDAC3 = 396

TABLE 1-continued

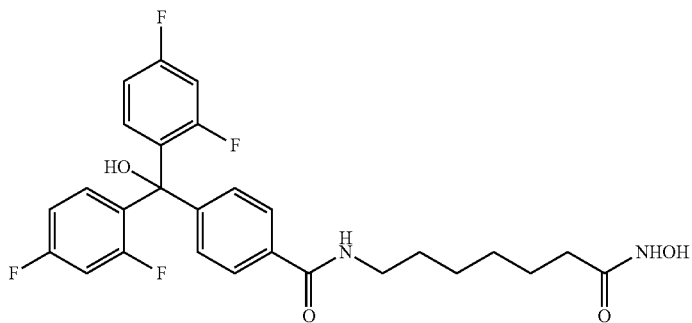

4-(bis(2,4-difluorophenyl)(hydroxy)methyl)-N-(7-(hydroxyamino)7-oxoheptyl)benzamide
IC$_{50}$(nM) HDAC6 = 5 HDAC3 = 137

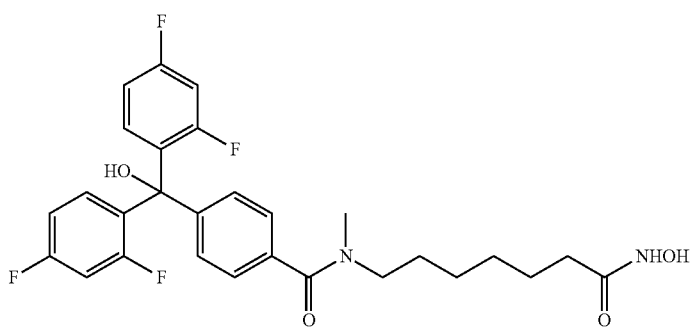

4-(bis(2,4-difluorophenyl)(hydroxy)methyl)-N-(7-(hydroxyamino)-7-oxoheptyl)-N-methylbenzamide
IC$_{50}$(nM) HDAC6 = 13 HDAC3 = 172

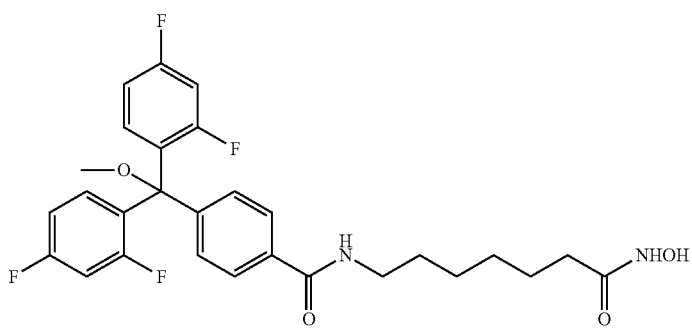

4-(bis(2,4-difluorophenyl)(methoxy)methyl)-N-(7-(hydroxyamino)-7-oxoheptyl)benzamide
IC$_{50}$(nM) HDAC6 = 20 HDAC3 = 495

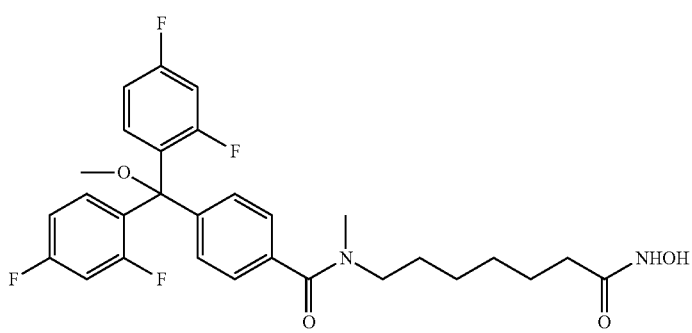

4-(bis(2,4-difluorophenyl)(methoxy)methyl)-N-(7-(hydroxyamino)-7-oxoheptyl)-N-methylbenzamide
IC$_{50}$(nM) HDAC6 = 26 HDAC3 = 1335

TABLE 1-continued

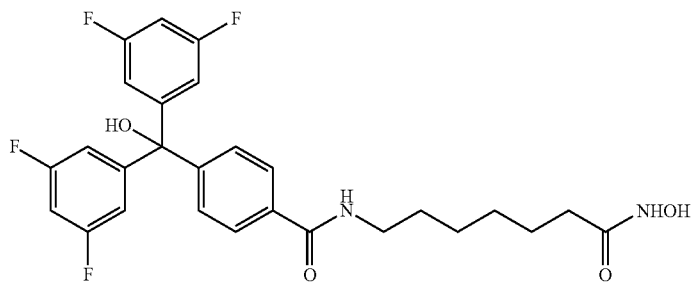

4-(bis(3,5-difluorophenyl)(hydroxy)methyl)-N-(7-(hydroxyamino)-7-
oxoheptyl)benzamide
IC$_{50}$(nM) HDAC6 = 4 HDAC3 = 208

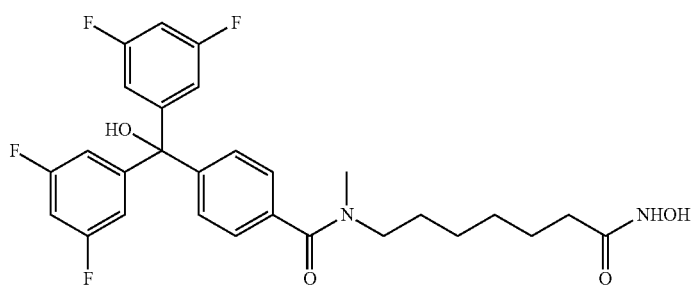

4-(bis(3,5-difluorophenyl)(hydroxy)methyl)-N-(7-(hydroxyamino)-7-
oxoheptyl)-N-methylbenzamide
IC$_{50}$(nM) HDAC6 = 15 HDAC3 = 186

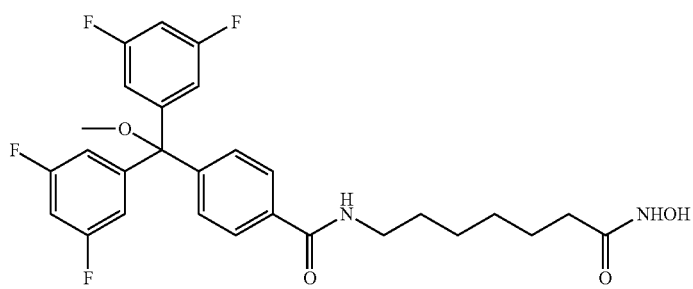

4-(bis(3,5-difluorophenyl)(methoxy)methyl)-N-(7-(hydroxyamino)-7-
oxoheptyl)benzamide
IC$_{50}$(nM) HDAC6 = 20 HDAC3 = 679

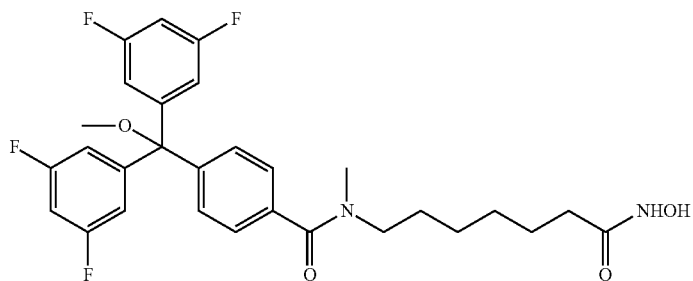

4-(bis(3,5-difluorophenyl)(methoxy)methyl)-N-(7-(hydroxyamino)-7-
oxoheptyl)-N-methylbenzamide
IC$_{50}$(nM) HDAC6 = 17 HDAC3 = 873

TABLE 1-continued

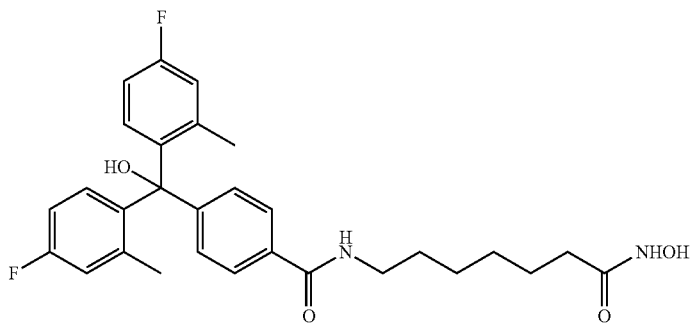

4-(bis(4-fluoro-2-methylphenyl)(hydroxy)methyl)-N-(7-(hydroxyamino)-7-oxoheptyl)benzamide
IC$_{50}$(nM) HDAC6 = 59 HDAC3 = 854

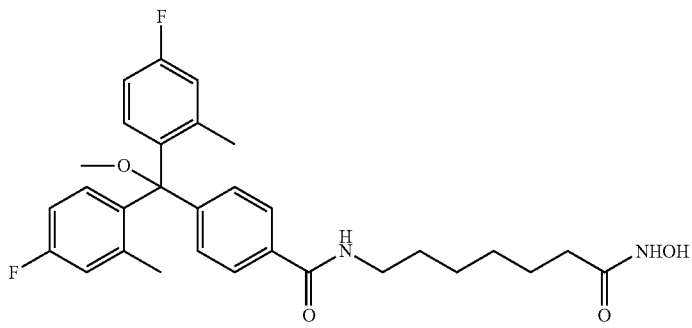

4-(bis(4-fluoro-2-methylphenyl)(methoxy)methyl)-N-(7-(hydroxyamino)-7-oxoheptyl)benzamide
IC$_{50}$(nM) HDAC6 = 127 HDAC3 = 2361

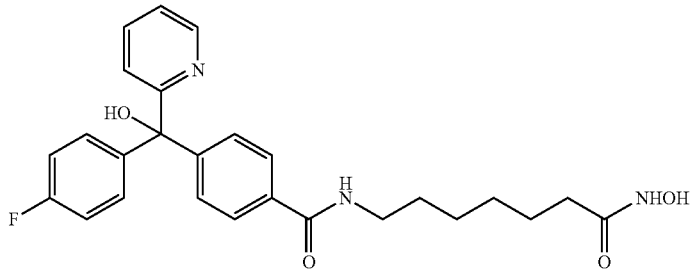

4-((4-fluorophenyl)(hydroxy)(pyridin-2-yl)methyl)-N-(7-(hydroxyamino)-7-oxoheptyl)benzamide
IC$_{50}$(nM) HDAC6 = 3 HDAC3 = 80

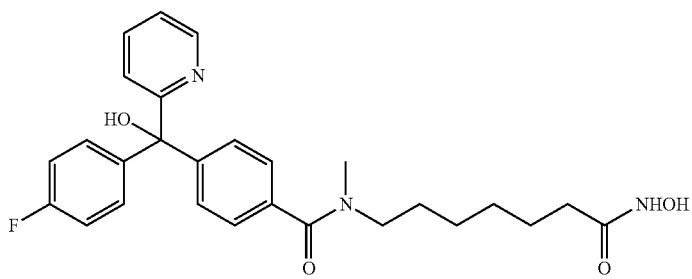

4-((4-fluorophenyl)(hydroxy)(pyridin-2-yl)methyl)-N-(7-(hydroxyamino)-7-oxoheptyl)-N-methylbenzamide
IC$_{50}$(nM) HDAC6 = 24 HDAC3 = 284

TABLE 1-continued

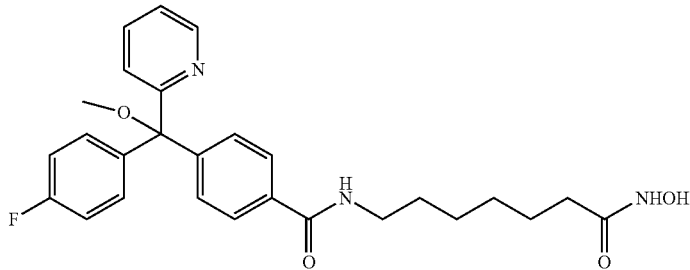

4-((4-fluorophenyl)(methoxy)(pyridin-2-yl)methyl)-N-(7-(hydroxyamino)-
7-oxoheptyl)benzamide
IC$_{50}$(nM) HDAC6 = 3 HDAC3 = 80

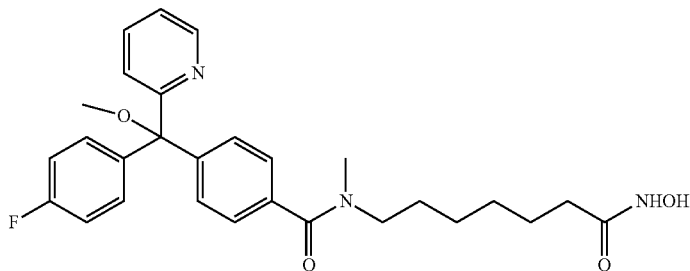

4-((4-fluorophenyl)(methoxy)(pyridin-2-yl)methyl)-N-(7-(hydroxyamino)-
7-oxoheptyl)-N-methylbenzamide
IC$_{50}$(nM) HDAC6 = 23 HDAC3 = 361

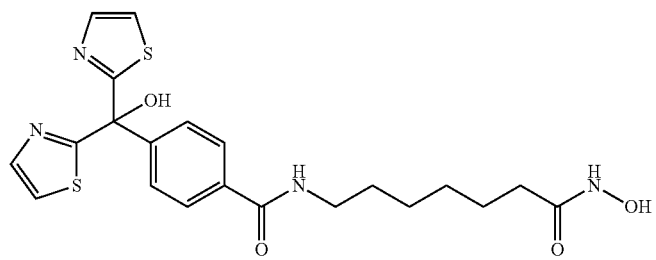

N-(7-(hydroxyamino)-7-oxoheptyl)-4-(hydroxydithiazol-2-ylmethyl)benzamide
IC$_{50}$(nM) HDAC6 = 5 HDAC3 = 141

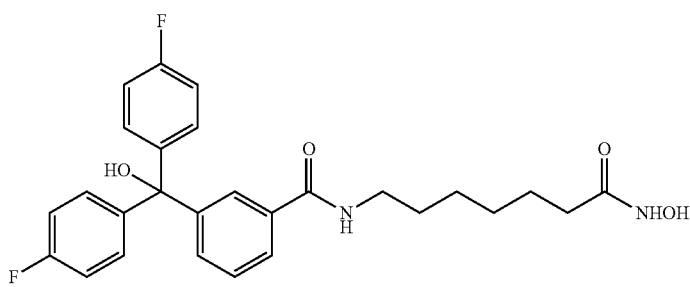

3-(bis(4-fluorophenyl)(hydroxy)methyl)-N-(7-(hydroxyamino)-7-oxoheptyl)benzamide
IC$_{50}$(nM) HDAC6 = 18 HDAC3 = 63

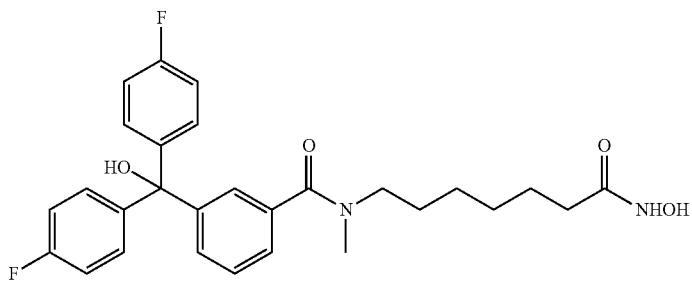

3-(bis(4-fluorophenyl)(hydroxy)methyl)-N-(7-(hydroxyamino)-7-
oxoheptyl)-N-methylbenzamide
IC$_{50}$(nM) HDAC6 = 72 HDAC3 = 349

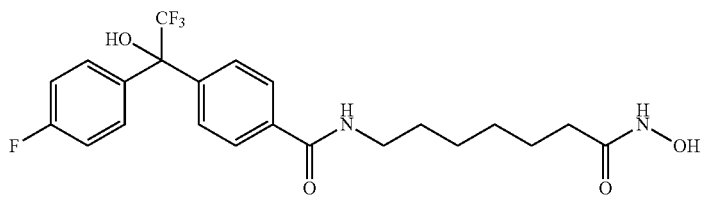

N-(7-(hydroxyamino)-7-oxoheptyl)-4-(2,2,2-trifluoro-1-(4-fluorophenyl)-
1-hydroxyethyl)benzamide
IC$_{50}$(nM) HDAC6 = 5 HDAC3 = 50

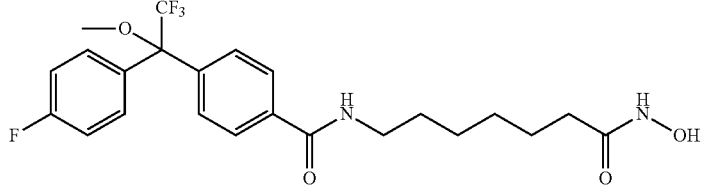

N-(7-(hydroxyamino)-7-oxoheptyl)-4-(2,2,2-trifluoro-1-(4-fluorophenyl)-1-
methoxyethyl)benzamide
IC$_{50}$(nM) HDAC6 = 10 HDAC3 = 174

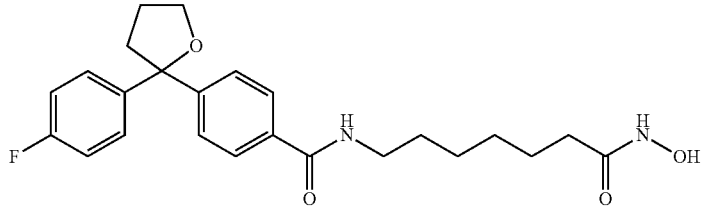

4-(2-(4-fluorophenyl)tetrahydrofuran-2-yl)-N-(7-(hydroxyamino)-7-oxoheptyl) benzamide
IC$_{50}$(nM) HDAC6 = 3 HDAC3 = 47

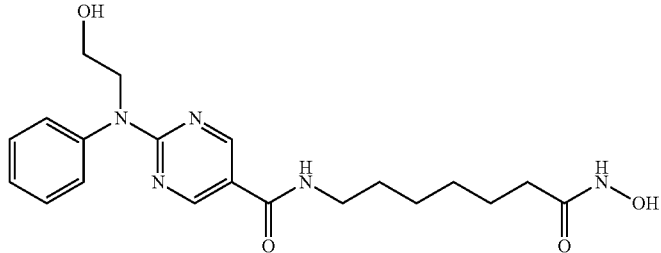

N-(7-(hydroxyamino)-7-oxoheptyl)-2-((2-hydroxyethyl)(phenyl)amino)
pyrimidine-5-carboxamide
IC$_{50}$(nM) HDAC6 = 8 HDAC3 = 75

TABLE 1-continued

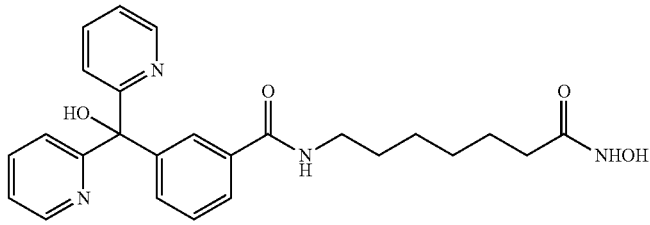

N-(7-(hydroxyamino)-7-oxoheptyl)-3-(hydroxydipyridin-2-ylmethyl)benzamide
IC$_{50}$(nM) HDAC6 = 41 HDAC3 = 285

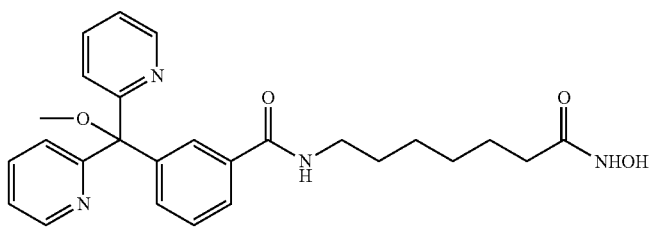

N-(7-(hydroxyamino)-7-oxoheptyl)-3-(methoxydipyridin-2-ylmethyl)benzamide
IC$_{50}$(nM) HDAC6 = 20 HDAC3 = 217

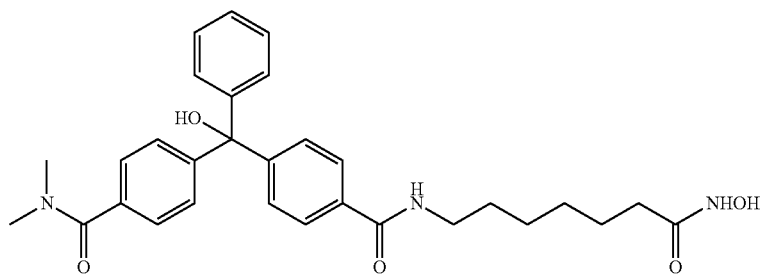

4-(hydroxy(4-(7-(hydroxyamino)-7-oxoheptylcarbamoyl)phenyl)(phenyl)methyl)-
N,N-dimethylbenzamide
IC$_{50}$(nM) HDAC6 = 4 HDAC3 = 86

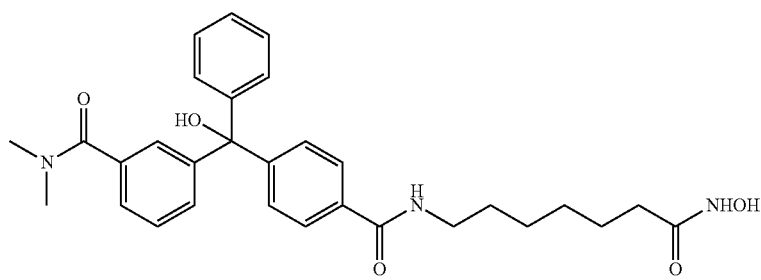

3-(hydroxy(4-(7-(hydroxyamino)-7-oxoheptylcarbamoyl)phenyl)(phenyl)methyl)-
N,N-dimethylbenzamide
IC$_{50}$(nM) HDAC6 = 3 HDAC3 = 90

TABLE 1-continued

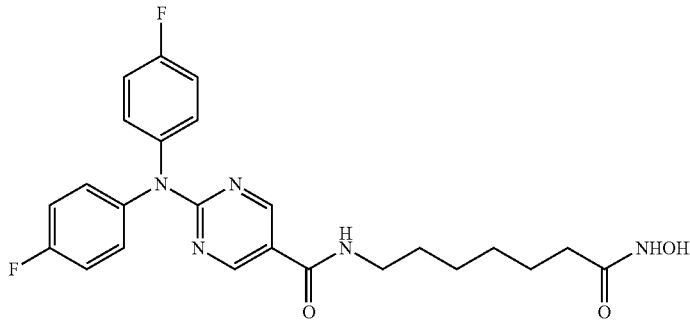

2-(bis(4-fluorophenyl)amino)-N-(7-(hydroxyamino)-7-oxoheptyl)pyrimidine-
5-carboxamide
IC$_{50}$(nM) HDAC6 = 12 HDAC3 = 124

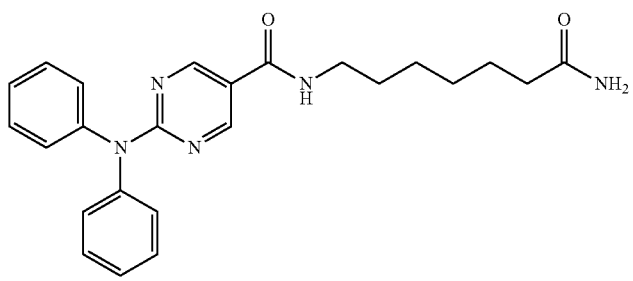

N-(7-amino-7-oxoheptyl)-2-(diphenylamino)pyrimidine-5-carboxamide
IC$_{50}$(nM) HDAC6 = >50 μM HDAC3 = >50 μM

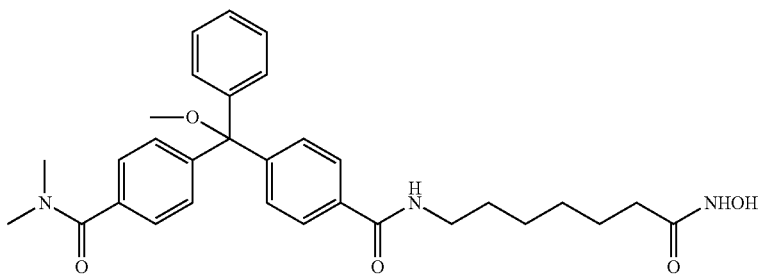

4-((4-(7-(hydroxyamino)-7-oxoheptylcarbamoyl)phenyl)(methoxy)(phenyl)methyl)-
N,N-dimethylbenzamide
IC$_{50}$(nM) HDAC6 = 4 HDAC3 = 103

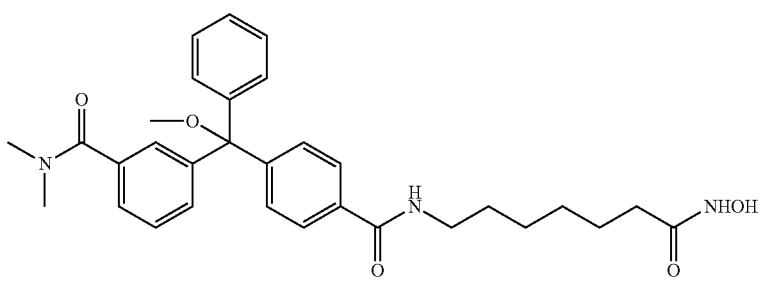

3-((4-(7-(hydroxyamino)-7-oxoheptylcarbamoyl)phenyl)(methoxy)(phenyl)methyl)-
N,N-dimethylbenzamide
IC$_{50}$(nM) HDAC6 = 3 HDAC3 = 85

TABLE 1-continued

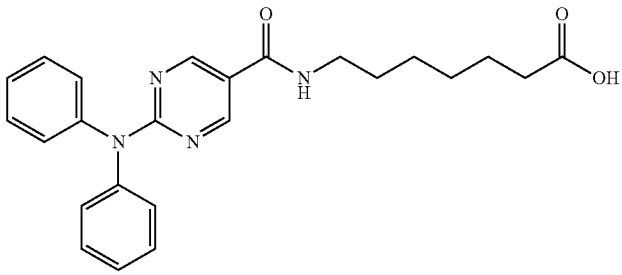

7-(2-(diphenylamino)pyrimidine-5-carboxamido)heptanoic acid
IC$_{50}$(nM) HDAC6 = 1251 HDAC3 = 19512

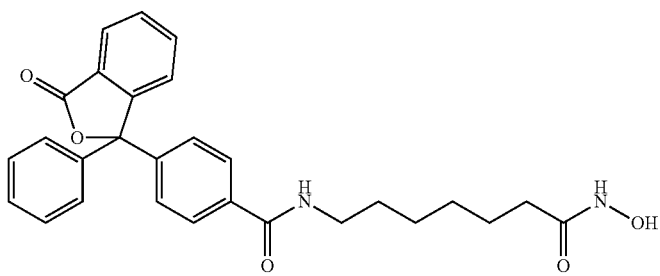

N-(7-(hydroxyamino)-7-oxoheptyl)-4-(3-oxo-1-phenyl-1,3-dihydroisobenzofuran-
1-yl)benzamide
IC$_{50}$(nM) HDAC6 = 11 HDAC3 = 153

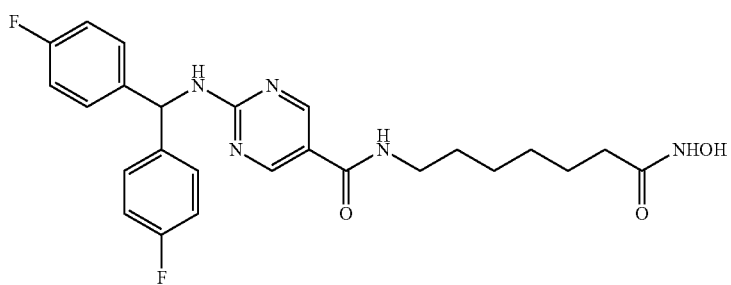

2-(bis(4-fluorophenyl)methylamino)-N-(7-(hydroxyamino)-7-oxoheptyl)pyrimidine-
5-carboxamide
IC$_{50}$(nM) HDAC6 = 5 HDAC3 = 65

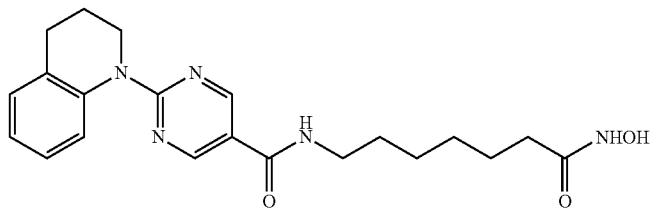

2-(3,4-dihydroquinolin-1(2H)-yl)-N-(7-(hydroxyamino)-7-oxoheptyl)pyrimidine-
5-carboxamide
IC$_{50}$(nM) HDAC6 = 6 HDAC3 = 50

TABLE 1-continued

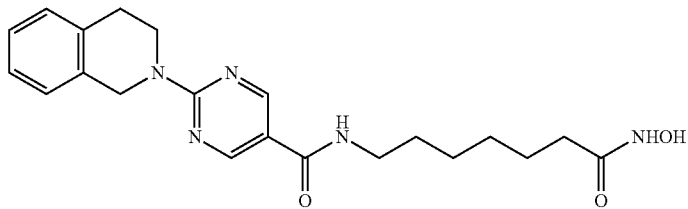

2-(3,4-dihydroisoquinolin-2(1H)-yl)-N-(7-(hydroxyamino)-7-
oxoheptyl)pyrimidine-5-carboxamide
IC$_{50}$(nM) HDAC6 = 3 HDAC3 = 53

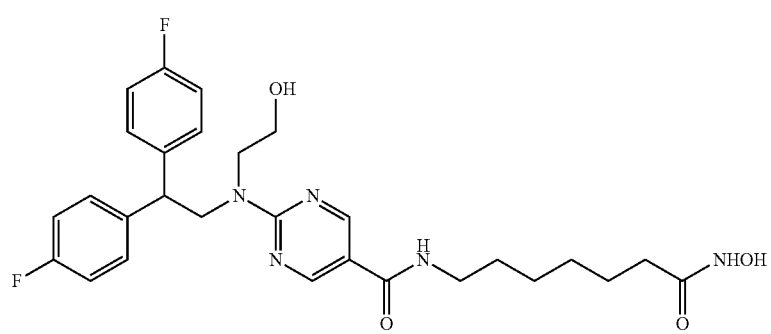

2-((2,2-bis(4-fluorophenyl)ethyl)(2-hydroxyethyl)amino)-N-(7-(hydroxyamino)-
7-oxoheptyl)pyrimidine-5-carboxamide
IC$_{50}$(nM) HDAC6 = 8 HDAC3 = 64

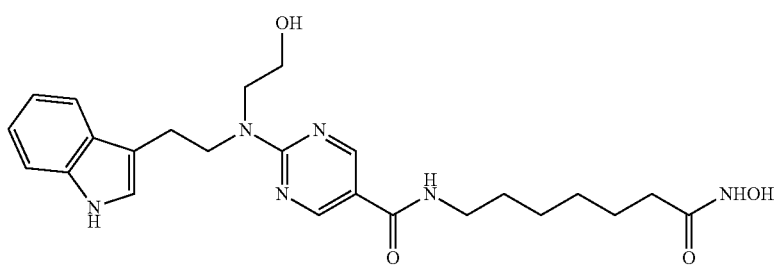

2-((2-(1H-indol-3-yl)ethyl)(2-hydroxyethyl)amino)-N-(7-(hydroxyamino)-7-
oxoheptyl)pyrimidine-5-carboxamide
IC$_{50}$(nM) HDAC6 = 3 HDAC3 = 35

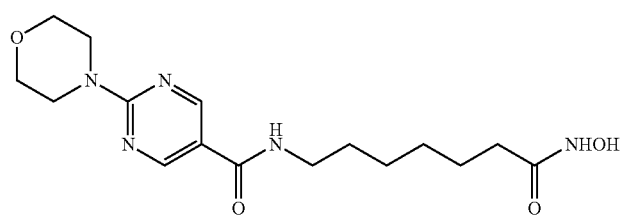

N-(7-(hydroxyamino)-7-oxoheptyl)-2-morpholinopyrimidine-5-carboxamide
IC$_{50}$(nM) HDAC6 = 8 HDAC3 = 51

TABLE 1-continued

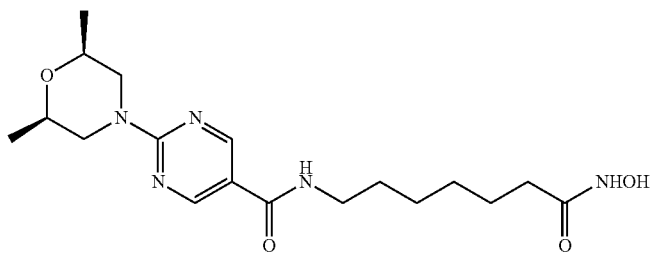

2-((2S,6R)-2,6-dimethylmorpholino)-N-(7-(hydroxyamino)-7-
oxoheptyl)pyrimidine-5-carboxamide
IC$_{50}$(nM) HDAC6 = 7 HDAC3 = 70

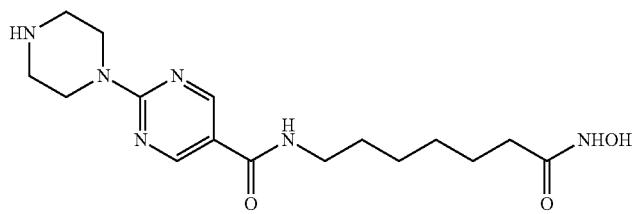

N-(7-(hydroxyamino)-7-oxoheptyl)-2-(piperazin-1-yl)pyrimidine-5-carboxamide
IC$_{50}$(nM) HDAC6 = 21 HDAC3 = 43

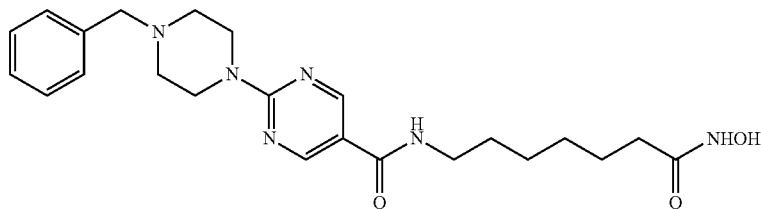

2-(4-benzylpiperazin-1-yl)-N-(7-(hydroxyamino)-7-oxoheptyl)pyrimidine-5-carboxamide
IC$_{50}$(nM) HDAC6 = 6 HDAC3 = 100

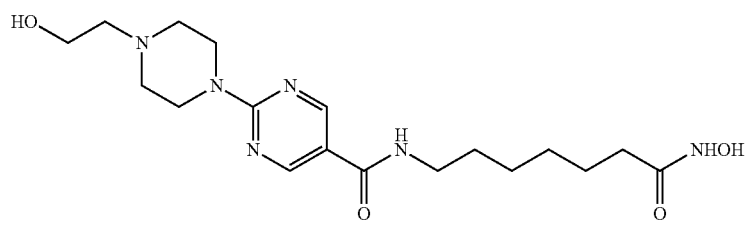

N-(7-(hydroxyamino)-7-oxoheptyl)-2-(4-(2-hydroxyethyl)piperazin-1-yl)pyrimidine-
5-carboxamide
IC$_{50}$(nM) HDAC6 = 13 HDAC3 = 58

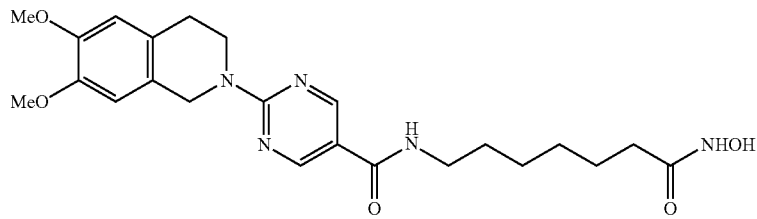

2-(6,7-dimethoxy-3,4-dihydroisoquinolin-2(1H)-yl)-N-(7-(hydroxyamino)-7-
oxoheptyl)pyrimidine-5-carboxamide
IC$_{50}$(nM) HDAC6 = 2 HDAC3 = 46

TABLE 1-continued

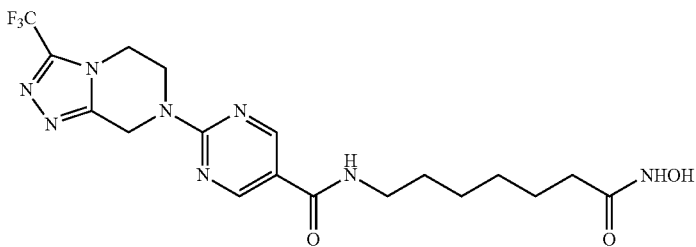

N-(7-(hydroxyamino)-7-oxoheptyl)-2-(3-(trifluoromethyl)-5,6-dihydro-
[1,2,4]triazolo[4,3-a]pyrazin-7(8H)-yl)pyrimidine-5-carboxamide
$IC_{50}$(nM) HDAC6 = 14 HDAC3 = 149

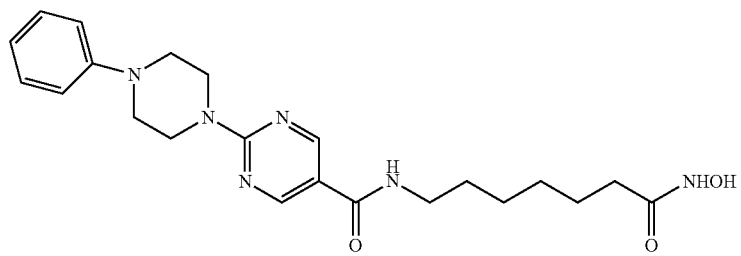

N-(7-(hydroxyamino)-7-oxoheptyl)-2-(4-phenylpiperazin-1-yl)pyrimidine-5-carboxamide
$IC_{50}$(nM) HDAC6 = 4 HDAC3 = 57

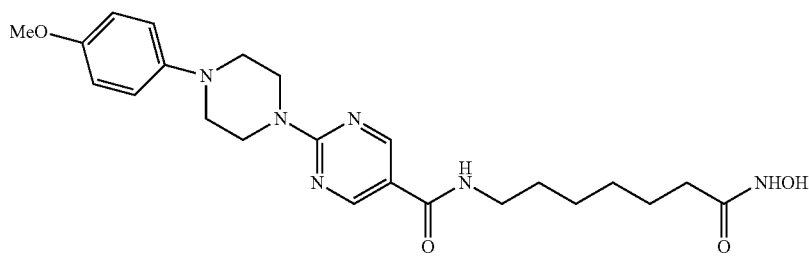

N-(7-(hydroxyamino)-7-oxoheptyl)-2-(4-(4-methoxyphenyl)piperazin-1-yl)pyrimidine-5-carboxamide
$IC_{50}$(nM) HDAC6 = 4 HDAC3 = 58

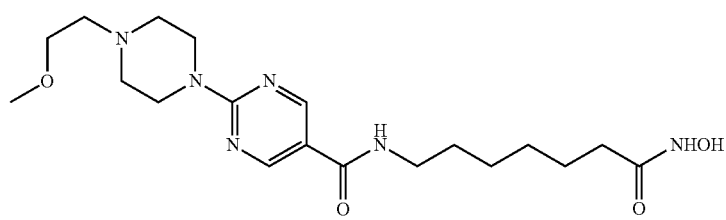

N-(7-(hydroxyamino)-7-oxoheptyl)-2-(4-(2-methoxyethyl)piperazin-1-yl)pyrimidine-5-
carboxamide
$IC_{50}$(nM) HDAC6 = 13 HDAC3 = 133

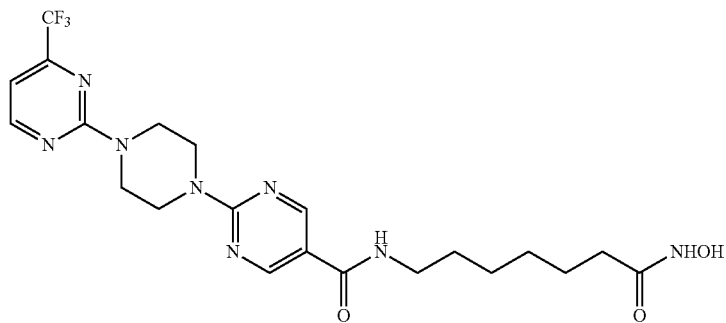

N-(7-(hydroxyamino)-7-oxoheptyl)-2-(4-(4-(trifluoromethyl)pyrimidin-2-yl)piperazin-1-yl)pyrimidine-5-carboxamide
IC$_{50}$(nM) HDAC6 = 7 HDAC3 = 54

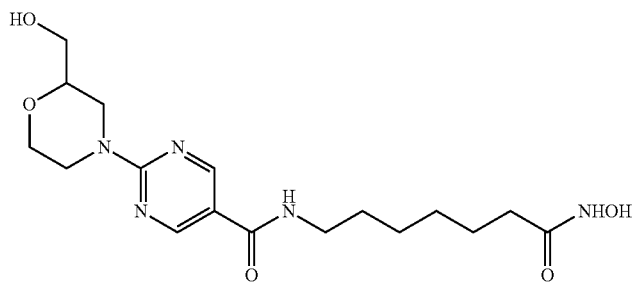

N-(7-(hydroxyamino)-7-oxoheptyl)-2-(2-(hydroxymethyl)morpholino)pyrimidine-5-carboxamide
IC$_{50}$(nM) HDAC6 = 7 HDAC3 = 34

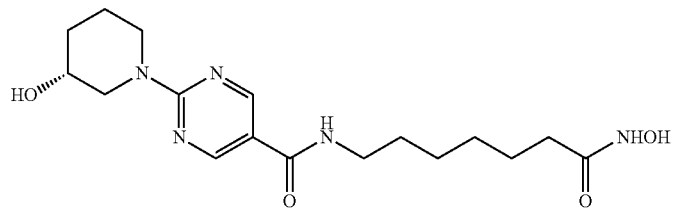

(R)-N-(7-(hydroxyamino)-7-oxoheptyl)-2-(3-hydroxypiperidin-1-yl)pyrimidine-5-carboxamide
IC$_{50}$(nM) HDAC6 = 7 HDAC3 = 49

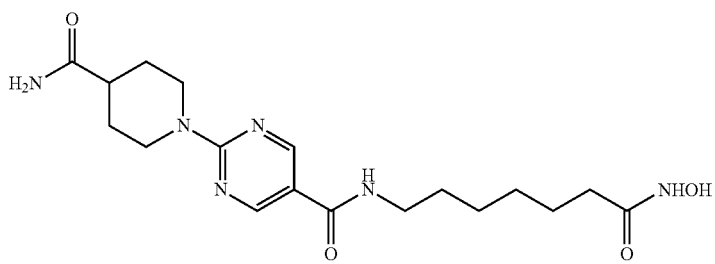

2-(4-carbamoylpiperidin-1-yl)-N-(7-(hydroxyamino)-7-oxoheptyl)pyrimidine-5-carboxamide
IC$_{50}$(nM) HDAC6 = 8 HDAC3 = 41

TABLE 1-continued

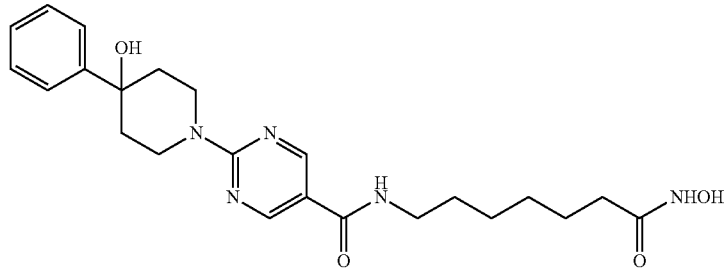

2-(4-hydroxy-4-phenylpiperidin-1-yl)-N-(7-(hydroxyamino)-7-oxoheptyl)pyrimidine-5-
carboxamide
IC$_{50}$(nM) HDAC6 = 4 HDAC3 = 39

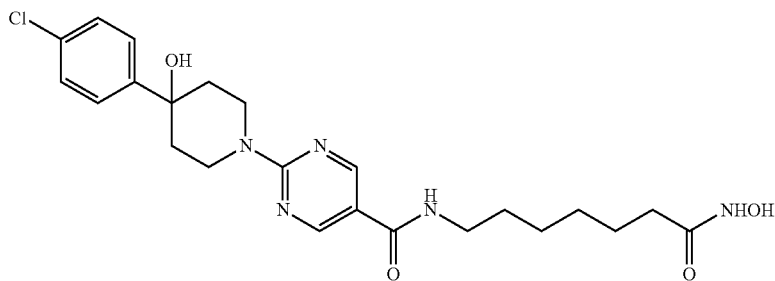

2-(4-(4-chlorophenyl)-4-hydroxypiperidin-1-yl)-N-(7-(hydroxyamino)-7-oxoheptyl)pyrimidine-
5-carboxamide
IC$_{50}$(nM) HDAC6 = 4 HDAC3 = 53

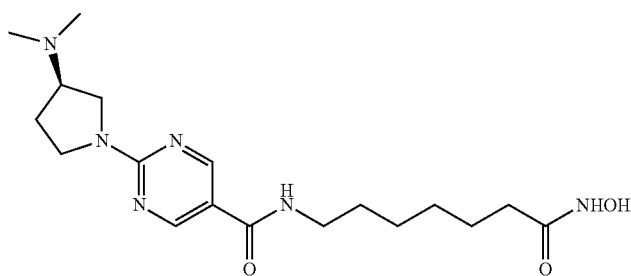

(R)-2-(3-(dimethylamino)pyrrolidin-1-yl)-N-(7-(hydroxyamino)-7-
oxoheptyl)pyrimidine-5-carboxamide
IC$_{50}$(nM) HDAC6 = 33 HDAC3 = 80

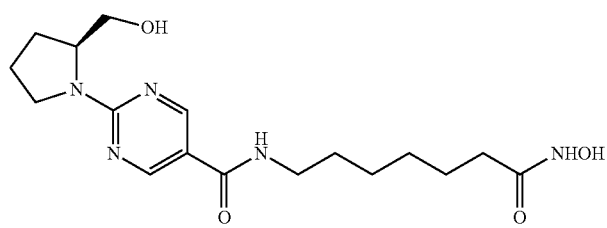

(S)-N-(7-(hydroxyamino)-7-oxoheptyl)-2-(2-(hydroxymethyl)pyrrolidin-1-
yl)pyrimidine-5-carboxamide
IC$_{50}$(nM) HDAC6 = 7 HDAC3 = 30

TABLE 1-continued

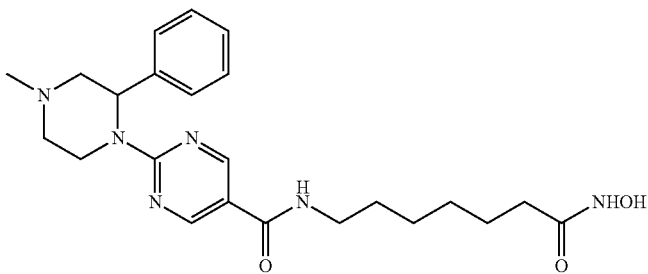

N-(7-(hydroxyamino)-7-oxoheptyl)-2-(4-methyl-2-phenylpiperazin-1-yl)pyrimidine-5-carboxamide
IC$_{50}$(nM) HDAC6 = 5 HDAC3 = 51

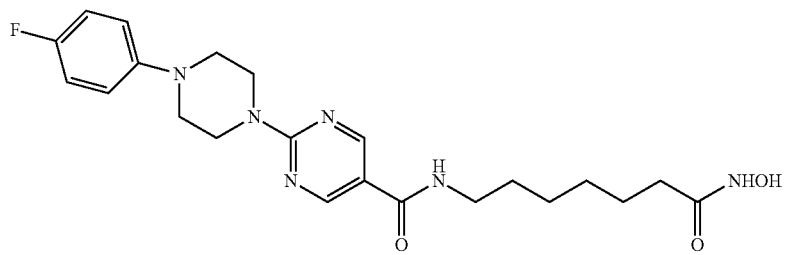

2-(4-(4-fluorophenyl)piperazin-1-yl)-N-(7-(hydroxyamino)-7-oxoheptyl)pyrimidine-5-carboxamide
IC$_{50}$(nM) HDAC6 = 5 HDAC3 = 52

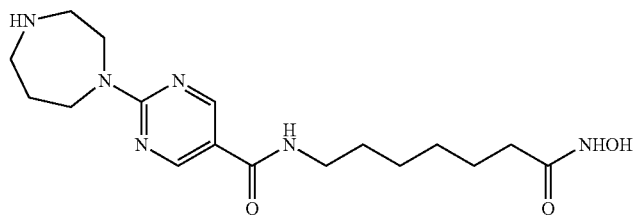

2-(1,4-diazepan-1-yl)-N-(7-(hydroxyamino)-7-oxoheptyl)pyrimidine-5-carboxamide
IC$_{50}$(nM) HDAC6 = 19 HDAC3 = 34

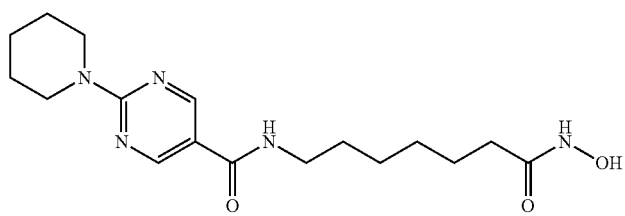

N-(7-(hydroxyamino)-7-oxoheptyl)-2-(piperidin-1-yl)pyrimidine-5-carboxamide
IC$_{50}$(nM) HDAC6 = 5 HDAC3 = 23

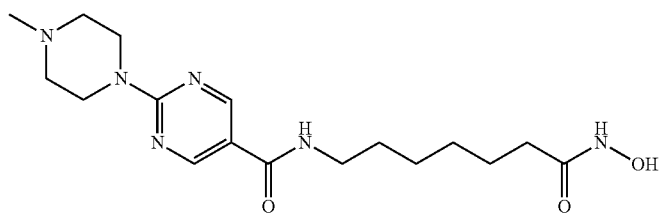

N-(7-(hydroxyamino)-7-oxoheptyl)-2-(4-methylpiperazin-1-yl)pyrimidine-5-carboxamide
IC$_{50}$(nM) HDAC6 = 18 HDAC3 = 87

In a most preferred embodiment of the invention, the HDAC6 inhibitor has the following chemical structure:

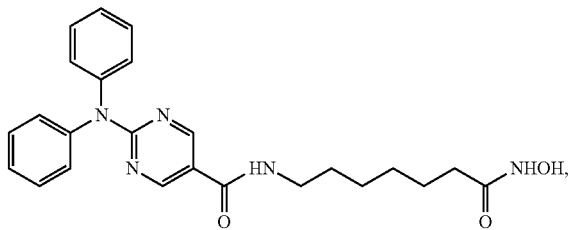

which is referred to herein as Compound A.

In preferred embodiments, a compound useful in the methods of the invention has one or more of the following properties: the compound is capable of inhibiting at least one histone deacetylase; the compound is capable of inhibiting HDAC6; the compound is a selective HDAC6 inhibitor; the compound binds to the poly-ubiquitin binding domain of HDAC6; the compound is capable of inducing apoptosis in cancer cells (especially multiple myeloma cells, non-Hodgkin's lymphoma (NML) cells, breast cancer cells, acute myelogenous leukemia (AML) cells); and/or the compound is capable of inhibiting aggresome formation.

In certain preferred embodiments, a compound useful in the methods of the invention comprises a metal binding moiety, preferably a zinc-binding moiety such as a hydroxamate. As noted above, certain hydroxamates are potent inhibitors of HDAC6 activity; without wishing to be bound by theory, it is believed that the potency of these hydroxamates is due, at least in part, to the ability of the compounds to bind zinc. In preferred embodiments, a compound useful in the methods of the invention includes at least one portion or region which can confer selectivity for a biological target implicated in the aggresome pathway, e.g., a biological target having tubulin deacetylase (TDAC) or HDAC activity, e.g., HDAC6. Thus, in certain preferred embodiments, a compound useful in the methods of the invention includes a zinc-binding moiety spaced from other portions of the molecule which are responsible for binding to the biological target.

The invention also provides for a pharmaceutical composition comprising a compound of formula I, or a pharmaceutically acceptable ester, salt, or prodrug thereof, together with a pharmaceutically acceptable carrier.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

A compound useful in the methods of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds useful in the methods of the invention can be prepared using salts of the starting materials or intermediates.

The free acid or free base forms of the compounds useful in the methods of the invention can be prepared from the corresponding base addition salt or acid addition salt from, respectively. For example a compound useful in the methods of the invention in an acid addition salt form can be converted to the corresponding free base by treating with a suitable base (e.g., ammonium hydroxide solution, sodium hydroxide, and the like). A compound useful in the methods of the invention in a base addition salt form can be converted to the corresponding free acid by treating with a suitable acid (e.g., hydrochloric acid, etc.).

Compounds useful in the methods of the present invention can be conveniently prepared, or formed during the process described herein, as solvates (e.g., hydrates). Hydrates of compounds useful in the methods of the present invention can be conveniently prepared by recrystallization from an aqueous/organic solvent mixture, using organic solvents such as dioxan, tetrahydrofuran or methanol.

In addition, some of the compounds useful in the methods of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds useful in the methods of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the methods of the present invention. All crystal forms of the compounds described herein are expressly included in the methods of the present invention.

The compounds useful in the methods of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Other Cancer Treatments

Any cancer treatment, such as a chemotherapy drug or other anti-cancer drug, may be used in combination with an HDAC inhibitor in the methods of the invention. The chemotherapy drug or other anti-cancer drug may be, for example, a small molecule organic compound, an antibody, a siRNA, an aptamer, a nucleic acid, a protein, or a peptide. Preferably, the anti-cancer drug is a proteasome inhibitor. More preferably, the proteasome inhibitor is bortezomib.

Pharmaceutical Compositions

In another aspect, the HDAC inhibitor is provided in a pharmaceutical composition comprising a compound of formula I, or a pharmaceutically acceptable ester, salt, or prodrug thereof, together with a pharmaceutically acceptable carrier. In a further aspect, the other cancer therapy is provided in a pharmaceutical composition.

Compounds useful in the methods of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound useful in the methods of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds useful in the methods of the invention can be administered in therapeutically effective amounts in combination with one or more therapeutic agents (pharmaceutical combinations). For example, synergistic effects can occur with other anti-proliferative, anti-cancer, immunomodulatory or anti-inflammatory substances. Where the compounds of the invention are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In certain embodiments, these compositions optionally further comprise one or more additional therapeutic agents. Alternatively, a compound useful in the methods of this invention may be administered to a patient in need thereof in combination with the administration of one or more other therapeutic agents. For example, additional therapeutic agents for conjoint administration or inclusion in a pharmaceutical composition with a compound useful in the methods of this invention may be an approved chemotherapeutic agent, or it may be any one of a number of agents undergoing approval in the Food and Drug Administration that ultimately obtains approval for the treatment of any disorder associated with cellular hyperproliferation. In certain other embodiments, the additional therapeutic agent is an anticancer agent, as discussed in more detail herein. In the treatment of cancer or protein degradation disorders, the compound may be combined with a proteasome inhibitor (e.g., bortezomib, R1 15777 FTI, MG132, NPI-0052, etc.). In the treatment of cancer or protein degradation disorders, the compound may be combined with protein degradation inhibitor (e.g. another inventive compound, a tubacin-like compound, bortezomib, R1 15777 FTI, MG132, NPI-0052, SAHA, $^{166}$Ho-DOTMP, arsenic trioxide, 17-AAG, MG 132, etc.).

It will also be appreciated that the compounds and pharmaceutical compositions useful in the methods of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

It will also be appreciated that the compounds and pharmaceutical compositions useful in the methods of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the compounds useful in the methods of the present invention include, but not limited to, surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, antibodies, aptamers, siRNAs, oligonucleotides, enzyme, ion channel and receptor inhibitors or activators to name a-few), hyperthermia and cryotherapy, agents to attenuate any adverse effects (e.g., antiemetics), and other approved chemotherapeutic drugs, including, but not limited to, alkylating drugs (e.g., mechlorethamine, chlorambucil, Cyclophosphamide, Melphalan, Ifosfamide), antimetabolites (e.g., Methotrexate), purine antagonists and pyrimidine antagonists (e.g., 6-Mercaptopurine, 5-Fluorouracil, Cytarabile, Gemcitabine), spindle poisons (e.g., Vinblastine, Vincristine, Vinorelbine, Paclitaxel), podophyllotoxins (e.g., Etoposide, Irinotecan, Topotecan), antibiotics (Doxorubicin, Bleomycin, Mitomycin), nitrosoureas (e.g., Carmustine, Lomustine), inorganic ions (e.g., Cisplatin, Carboplatin), enzymes (e.g., Asparaginase), and hormones (e.g., Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www dot nci dot nih dot gov) and the Food and Drug Administration (FDA) website for a list of the FDA approved oncology drugs (www dot fda dot gov/cder/cancer/dmglistframe).

In certain embodiments, the pharmaceutical compositions useful in the methods of the present invention further comprise one or more additional therapeutically active ingredients (e.g., chemotherapeutic and/or palliative). For purposes of the invention, the term "palliative" refers to treatment that is focused on the relief of symptoms of a disease and/or side effects of a therapeutic regimen, but is not curative. For example, palliative treatment encompasses painkillers, antinausea medications, anti-pyretics, and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

The compounds and compositions can be administered together with hormonal and steroidal anti-inflammatory agents, such as but not limited to, estradiol, conjugated estrogens (e.g., PREMARIN, PREMPRO, AND PREMPHASE), 17 beta estradiol, calcitonin-salmon, levothyroxine, dexamethasone, medroxyprogesterone, prednisone, cortisone, flunisolide, and hydrocortisone; non-steroidal anti-inflammatory agents, such as but not limited to, tramadol, fentanyl, metamizole, ketoprofen, naproxen, nabumetone, ketoralac, tromethamine, loxoprofen, ibuprofen, aspirin, and acetaminophen; anti-TNF-α antibodies, such as infliximab (REMICADE™) and etanercept (ENBREL™).

The pharmaceutical compositions useful in the methods of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions useful in the methods of this invention can be administered to humans and other animals orally, rectally, parenterally, intracisternally, intravaginally, intraperitoneally, topically (as by powders, ointments, or drops), buccally, or as an oral or nasal spray.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound useful in the methods of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds useful in the methods of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds useful in the methods of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) useful in the methods of this invention per day in single or multiple doses. Therapeutic amounts or doses will also vary depending on route of administration, as well as the possibility of co-usage with other agents.

Upon improvement of a subject's condition, a maintenance dose of a compound, composition or combination useful in the methods of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions useful in the methods of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound useful in the methods of the invention and a co-agent, are both administered to a patient simultaneously in the form of a single entity or dosage. The term "non-fixed combination" means that the active ingredients, e.g., a compound useful in the methods of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Types of Cancer

The methods of the invention may be used to identify cancer patients that will or are likely to respond to treatment with an HDAC inhibitor, alone or in combination with another cancer therapy. The methods of the invention may be used to identify patients having any type of cancer. Preferably, the cancer is selected from the group consisting of: brain/neuronal cancer, breast cancer, cancer of the central nervous system, haematopoietic and lymphoid tissue cancer, kidney cancer, cancer of the large intestine, liver cancer, lung cancer, cancer of the oesophagus, pancreatic cancer, prostate cancer, skin cancer, soft tissue cancer, and stomach cancer.

Biological Samples

The methods of the invention may involve taking a biological sample from a patient in order to determine the gene mutation status of the sample or the gene expression level status of the sample. For example, the biological sample may be a from a tumor tissue, tumor biopsy, whole blood, blood serum, blood plasma, semen, urine, mucus, or other body sample. In a preferred embodiment of the invention, the biological sample is blood serum, blood plasma, tumor tissue, or tumor biopsy sample. Tumor tissue may be formalin-fixed paraffin embedded tumor tissue or fresh frozen tumor tissue.

Biomarkers

The methods of the invention may be used to identify biomarkers that can be used to identify cancer patients that will or are likely to respond to treatment with a HDAC inhibitor, alone or in combination with another cancer treatment. For example, gene mutations that are correlated with cell sensitivities to one or more cancer drugs may be used as biomarkers. In addition, gene expression levels of genes that are correlated with cell sensitivities to one or more cancer drugs may be used as biomarkers.

Preferably, the biomarkers are selected from the group consisting of human epidermal growth factor receptor 2 (Her2); erythroblastic leukemia viral oncogene homolog 2 (ERBB2); SMAD family member 4 (SMAD4); phosphatase and tensin homolog (PTEN); epidermal growth factor receptor oncogene (EGFR); histone-lysine N-methyltransferase (EZH2); SET domain containing 2 (SETD2); von Hippel-Lindau tumor suppressor (VHL); pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (S. cerevisiae) (DCUN1D4); ras-related C3 botulinum toxin substrate 2 (RAC2); acyl-Coenzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); abhydrolase domain containing 14A (ABHD14A); UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3). Each of these genes or gene mutations is well known in the art.

The invention also includes mutations, mutants, or variants of the above biomarker proteins or genes. In those mutations, mutants, or variants, the native sequence of the biomarker protein or gene is changed by one or more substitutions, modifications, deletions, or insertions of one or more amino acids or nucleic acids in the protein or gene. In addition, those mutations, mutants, or variants may also encompass gene amplification, chromosomal translocation, protein overexpression, protein underexpression, gene overexpression, and gene underexpression. The term "native sequence" refers to an amino acid sequence or a nucleic acid sequence that is identical to a wild-type or native form of a biomarker protein or gene.

Kits

Certain embodiments of the invention include kits that may be used in the methods of the invention.

For example, in a certain embodiment of the invention, the invention provides a kit comprising a nucleic acid or probe that is complementary to any one of the genes, or a fragment thereof, selected from the group consisting of erythroblastic leukemia viral oncogene homolog 2 (ERBB2); SMAD family member 4 (SMAD4); phosphatase and tensin homolog (PTEN); epidermal growth factor receptor oncogene (EGFR); histone-lysine N-methyltransferase (EZH2); SET domain containing 2 (SETD2); von Hippel-Lindau tumor suppressor (VHL); pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); abhydrolase domain containing 14A (ABHD14A); UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3), and instructions for use of the nucleic acid to detect the presence of the gene or the expression level of the gene.

Another embodiment of the invention provides a kit comprising an antibody that binds to a protein produced by any one of the genes, or a fragment thereof, selected from the group consisting of erythroblastic leukemia viral oncogene homolog 2 (ERBB2); SMAD family member 4 (SMAD4); phosphatase and tensin homolog (PTEN); epidermal growth factor receptor oncogene (EGFR); histone-lysine N-methyltransferase (EZH2); SET domain containing 2 (SETD2); von Hippel-Lindau tumor suppressor (VHL); pterin-4 alpha-carbinolamine dehydratase/dimerization cofactor of hepatocyte nuclear factor 1 alpha (PCBD1); protein phosphatase 2, regulatory subunit B, gamma isoform (PPP2R2C); neural precursor cell expressed, developmentally downregulated 4 (NEDD4); prolyl 4-hydroxylase, alpha polypeptide II (P4HA2); SLC2A4 regulator (SLC2A4RG); sulfatase 2 (SULF2); lysosomal protein transmembrane 4 alpha (LAPTM4A); 3'-phosphoadenosine 5'-phosphosulfate synthase 2 (PAPSS2); aldo-keto reductase family 1, member C1 (dihydrodiol dehydrogenase 1; 20-alpha (3-alpha)-hydroxysteroid dehydrogenase) (AKR1C1); protein tyrosine phosphatase, non-receptor type 12 (PTPN12); DCN1, defective in cullin neddylation 1, domain containing 4 (*S. cerevisiae*) (DCUN1D4); ras-related C3 botulinum toxin substrate 2 (RAC2); acyl-Coexzyme A dehydrogenase, C-4 to C-112 straight chain (ACADM); Rho GTPase activating protein 4 (ARHGAP4); ATPase type 13A1 (ATP13A1); chemokine receptor 7 (CCR7); coronin 7 (CORO7); CXXC finger 4 (CXXC4); differentially expressed in FDCP 6 homolog (DEF6); KRI1 homolog (KRI1); limb region 1 homolog (LMBR1L); leukotriene B4 receptor (LTB4R); RAD54-like 2 (RAD54L2); chromosome X open reading frame 21 (CXorf21); SREBF chaperone (SCAP); selectin L (SELL); splicing factor 3a, subunit 2 (SF3A2); Lyrm7 homolog (LYRM7); O-linked N-acetylglucosamine transferase (OGT); tubulin, alpha 3c (TUBA3C); tubulin, alpha 3d (TUBA3D); KH-type splicing regulatory protein (KHSRP); DEAH (Asp-Glu-Ala-His) box polypeptide 30 (DHX30); APEX nuclease (apurinic/apyrimidinic endonuclease) 2 (APEX2); abhydrolase domain containing 14A (ABHD14A); UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3), and instructions for use of the antibody to detect the presence of the gene or the expression level of the gene.

Pharmaceutical Combinations

Compounds of the invention can be administered in therapeutically effective amounts in combination with one or more therapeutic agents (pharmaceutical combinations). In general, a combination therapy envisions administration of two or more drugs during a single cycle or course of therapy. In a particular embodiment, the compounds of the invention are administered in combination with lenalidomide (Revlimid), which has the following structure:

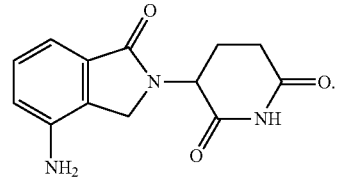 [SMILES: Nc1cccc2c1CN(C1CCC(=O)NC1=O)C2=O]

Revlimid is described, for example, in U.S. Pat. No. 5,635,517, which is incorporated herein by reference in its entirety.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In an particular embodiment, provided herein is a pharmaceutical composition comprising 2-(diphenylamino)-N-(7-(hydroxyamino)-7-oxoheptyl)pyrimidine-5-carboxamide, Revlimid, and a pharmaceutically acceptable carrier. In another embodiment, provided herein is a method of treating multiple myeloma in a subject in need thereof comprising administering to the subject 2-(diphenylamino)-N-(7-(hydroxyamino)-7-oxoheptyl)pyrimidine-5-carboxamide, and Revlimid. The agents can be administered together in one unit dose, separately but at approximately the same time, or at different times.

All patents, patent applications, and publications mentioned herein, both supra and infra, are hereby incorporated by reference in their entirety.

EXAMPLES

The following examples are provided to aid in the understanding of the invention. It is understood that modifications can be made to the procedures set forth below without departing from the spirit and scope of the invention.

Conventional techniques of molecular biology and nucleic acid chemistry, which are within the skill of the art, are explained in the literature and used in the practice of the invention. See, for example, Sambrook, J. et al., Molecular Cloning: A Laboratory Manual, Cold Spring Harbor Laboratory Press, Cold Spring Harbor, N.Y., 1989; Gait, M. J. (ed.), Oligonucleotide synthesis—a practical approach, IRL Press Limited, 1984; Hames, B. D. and Higgins, S. J. (eds.), Nucleic acid hybridisation—a practical approach, IRL Press Limited, 1985; and a series, Methods in Enzymology, Academic Press, Inc., all of which are incorporated herein by reference.

Example 1—Association Study of Cancer Types

This example describes the association study that was performed to determine which types of cancer are sensitive to treatment with Compound A alone or in combination with bortezomib.

65 cancer cell lines (including 12 of breast cancer, 11 of hematologic cancer, 9 of colorectal cancer, 6 of lung cancer, 6 of skin cancer, 4 brain cancer, 3 of renal cancer, 3 of liver cancer, 3 of prostate cancer, 3 of pancreatic cancer, 3 of ovarian cancer, and 2 of stomach cancer) were selected for analysis. Each of the cell lines was cultured and treated with the HDAC6 inhibitor, Compound A, with or without the proteasome inhibitor, bortezomib, before their cell viabilities were measured at the end of treatments. The sensitivities of the cell lines were described using the concentration of Compound A that provides 50% inhibition of cell viabilities ($IC_{50}$). In all analyses, the logarithm of drug sensitivity values (i.e., Log [IC50]) was used, which is more normally distributed than the raw $IC_{50}$ values. This is because most standard statistical tests (e.g., t-test and correlation analysis) assume the normal distribution of data points.

The results of this association study are as follows. Most cell lines were resistant to treatment with either Compound A alone or bortezomib alone. Also, cell lines of ovarian cancer were resistant to combination treatment with Compound A and bortezomib. In addition, cell lines for brain/neuron cancer, breast cancer, lymphoid cancer, kidney cancer, colon/large intestine cancer, and skin cancer were sensitive to combination treatment with Compound A and bortezomib. Further, cell lines for hematologic malignant cancer were the most sensitive to treatment with both Compound A alone, or combination treatment with Compound A and bortezomib.

Example 2—Association Study of Gene Mutations

This example describes the association study that was performed to determine which gene mutations, and hence types of cancer, are sensitive to treatment with a Compound A alone or in combination with bortezomib.

65 cancer cell lines (including 12 of breast cancer, 11 of hematologic cancer, 9 of colorectal cancer, 6 of lung cancer, 6 of skin cancer, 4 brain cancer, 3 of renal cancer, 3 of liver cancer, 3 of prostate cancer, 3 of pancreatic cancer, 3 of ovarian cancer, and 2 of stomach cancer) were selected for analysis. Each of the cell lines was cultured and treated with the HDAC6 inhibitor, Compound A, with or without the proteasome inhibitor, bortezomib, before their cell viabilities were measured at the end of treatments. The sensitivities of the cell lines were described using the concentration of Compound A that provides 50% inhibition of cell viabilities ($IC_{50}$). In all analyses, the logarithm of drug sensitivity values (i.e., Log [IC50]) was used, which is more normally distributed than the raw $IC_{50}$ values. This is because most standard statistical tests (e.g., t-test and correlation analysis) assume the normal distribution of data points.

Next, the genetic characteristics (in this example, mutations) of the tested cell lines associated with their drug responses were investigated.

For the association tests of gene mutations, 50 common oncogene/tumor suppressor genes were selected to analyze the results. Mutation profiles of the cell lines were downloaded from the Sanger COSMIC DB on the Internet: www dot sanger dot ac dot uk/cosmic. For each gene locus, the "Fisher's Exact Test" was used to calculate statistical significance ($p<0.05$) of association between the genotype and the cell sensitivities to the treatments. The genotypes of eight gene mutations were identified in these tests.

Overexpression of the human epidermal growth factor receptor 2 (Her2) protein, as compared to a normalized protein expression level of the protein, caused by erythroblastic leukemia viral oncogene homolog 2 (ERBB2) gene amplification or by any other means, in the breast cancer cell lines was sensitive to treatment with Compound A.

Basal-type or triple negative mutations (estrogen receptor-negative, progesterone receptor-negative and HER2/neu-negative) in the breast cancer cell lines were resistant to treatment with Compound A.

A gene mutation in the SMAD4 gene in colorectal cancer cell lines was sensitive to combination treatment with Compound A and bortezomib.

A gene mutation in the phosphatase and tensin homolog gene, PTEN, in all tested cancer cell lines was sensitive to combination treatment with Compound A and bortezomib.

A gene mutation in the histone-lysine N-methyltransferase gene, EZH2, in all tested cancer cell lines was sensitive to combination treatment with Compound A and bortezomib.

A gene mutation in the epidermal growth factor receptor oncogene, EGFR, in all tested cancer cell lines was sensitive to combination treatment with Compound A and bortezomib.

A gene mutation in the SET domain containing 2 gene, SETD2, in all tested cancer cell lines was sensitive to combination treatment with Compound A and bortezomib.

A gene mutation in the Von Hippel-Lindau tumor suppressor gene, VHL, in all tested cancer cell lines was sensitive to combination treatment with Compound A and bortezomib.

Example 3—Association Study of Gene Expression Levels

This example describes the association study that was performed to determine which gene expression profiles, and hence types of cancer, are sensitive to treatment with Compound A alone or in combination with bortezomib.

65 cancer cell lines (including 12 of breast cancer, 11 of hematologic cancer, 9 of colorectal cancer, 6 of lung cancer, 6 of skin cancer, 4 brain cancer, 3 of renal cancer, 3 of liver cancer, 3 of prostate cancer, 3 of pancreatic cancer, 3 of ovarian cancer, and 2 of stomach cancer) were selected for analysis. Each of the cell lines was cultured and treated with the HDAC6 inhibitor, Compound A, with or without the proteasome inhibitor, bortezomib, before their cell viabilities were measured at the end of treatments. The sensitivities of the cell lines were described using the concentration of Compound A that provides 50% inhibition of cell viabilities ($IC_{50}$). In all analyses, the logarithm of drug sensitivity values (i.e., Log [IC50]) was used, which is more normally distributed than the raw $IC_{50}$ values. This is because most standard statistical tests (e.g., t-test and correlation analysis) assume the normal distribution of data points.

Next, the genetic characteristics (in this example, gene expression levels) of the tested cell lines associated with their drug responses were investigated.

For the association tests of gene expression levels, the gene-expression profiles of the cell lines were obtained from two independent sources: the ArrayExpress (AE) database on the Internet: <URL: http://www.ebi.ac.uk/arrayexpress/>, which is maintained by the European Bioinformatics Institute, and the caArray database on the Internet: <URL: https://cabig.nci.nih.gov/caArray_GSKdata/>, which is from NIH. In addition, the Affymetrix CEL files, which contain the expression intensity of individual genes from these public databases, were downloaded, and then the R/BioConductor packages on the Internet: <URL:http://bioconductor.org> were used in order to normalize the gene-expression values between individual cell lines. The correlation coefficient and its significance ($p<0.001$) were calculated using the CORTEST function of R package between the $IC_{50}$ values and the normalized gene expression levels for each probe-set. For validation, only genes with all probe sets showing significant correlations were reported; genes were removed if any of its probe-sets were non-significant.

In total, the expression levels of 48 genes showed significant association with the cell sensitivities to the treatments.

Thirty-five of these forty-eight genes were associated with sensitivities to treatment with Compound A alone. Eleven genes, PCBD1, PPP2R2C, NEDD4, P4HA2, SLC2A4RG, SULF2, LAPTM4A, PAPSS2, AKR1C1, PTPN12, and DCUN1D4 had expression levels that were positively associated with the $IC_{50}$ values (i.e., the higher the gene expression level, the more resistant the cell is to the treatment; or the lower the gene expression level, the more sensitive the cell is to the treatment). Twenty-four genes, RAC2, ACADM, ARHGAP4, ATP13A1, CCR7, CORO7, CXXC4, DEF6, KRI1, LMBR1L, LTB4R, RAD54L2, CXorf21, SCAP, SELL, SF3A2, LYRM7, OGT, TUBA3C, TUBA3D, KHSRP, DHX30, APEX2, and ABHD14A had expression levels that were negatively associated with the $IC_{50}$ values (i.e., the higher the gene expression level, the more sensitive the cell is to the treatment; or the lower the gene expression level, the more resistant the cell is to the treatment).

Thirteen of these forty-eight genes were associated with sensitivities to combination treatment with Compound A and bortezomib. Five genes UGDH, H2AFY2, MYO5C, NPNT, and KIAA1598, had expression levels that were positively associated with the $IC_{50}$ values (i.e., the higher the gene expression level, the more resistant the cell is to the treatment; or the lower the gene expression level, the more sensitive the cell is to the treatment). Eight genes, SRGN, COL6A3, GPSM3, HSD11B1, PEX6, RAC2, SSX5, and ACBD3, had expression levels that were negatively associated the $IC_{50}$ values (i.e., the higher the gene expression level, the more sensitive the cell is to the treatment; or the lower the gene expression level, the more resistant the cell is to the treatment).

Example 4: Gene Signatures Associated with Compound A Sensitivity

These new groups of genes have been identified to be associated with cytotoxic sensitivity to Compound A after analyzing Compound A cytotoxic activity data using a different gene expression profile database—CCLE (Cancer Cell Line Encyclopedia). Two independent data analysis methods were used to identify gene signatures associated with Compound A sensitivity, i.e., the t-test and multi-regression methods.

In t-tests, the gene expression data were grouped from either sensitive or resistant cells in the database and compared them to the general data pool, respectively, in order to identify the gene signature specifically associated with either a sensitive (group 1) or resistant (group 2) phenotype. In the multi-regression method, whole experimental IC50 data was used to generate an IC50 prediction curve, which was comprised of 31 genes (group 3) expression data using the multi-regression algorithm. The prediction curve will be used to predict the sensitivity (IC50) of any given cells based on its gene expression data. Both methods have been popularly used to generate gene expression signatures and the results from both methods for future experimental validation are included here.

Comparing with the previous gene list, there are two overlapped genes, NEDD4 and PAPSS2 (in (3) below).

(1) A gene expression signature comprised of these 28 genes has been found by t-test in those cells which are sensitive to Compound A:
TFP1, DDX60, MYL9, EREG, IL18, LOC253039, PLAU, CXCL2, FOXQ1, PYCARD, TSTD1, AHNAK2, LHFP, LEPREL1, UCP2, IL1RAP, SNAI2, RHOF, FZD5, PRTFDC1, MXRA7, STEAP2, C15orf48, SMARCA1, PTGES, EGFR, SATB2, LOC100288092, (2) A gene expression signature comprised of these 25 genes have been found by t-test in those cells which are resistant to Compound A:
EREG, GDPD5, IFITM1, LOC100129502, INHBB, S100A10, S100A6, SCML1, ABCC4, THRB, GNG12, SDCBP, PTGR1, GSTA4, MGST1, CELSR2, SEPT10, ARNTL2, SMARCA1, MSN, FAM43A, PROCR, ELOVL7, CAPG, ANXA1, (3) A Compound A sensitivity prediction curve comprised of these 31 genes expression data using multi-regression method:
SMARCA1, CNKSR3, TFPI, FBXO17, NEDD4, ITGAV, COL18A1, WWTR1, LOC100130776, HECTD2, SLC26A2, ADM, GJC1, RBPMS, PAPSS2, LAMB1, TXNIP, FSCN1, ARHGDIB, TRAPPC2, DRAM1, CRIM1, NME4. UGDH, FAM57A, AGPAT9, FMNL2, FAM114A1, GPR125, GALNT2, SLC7A11.

Example 5: Large-Scale Cancer Cell Line Screening with the Selective HDAC-6 Inhibitor Compound A Identifies Potential Cancer Targets and Candidate Predictive Biomarkers Compound A is a selective inhibitor of HDAC6 (Histone Deacetylase 6) currently in Phase 1 clinical trials as a single agent and in combination with bortezomib (Velcade) or lenalidomide (Revlimid) in relapsed and refractory multiple myeloma. Inhibitors of HDACs have been shown to exhibit potent anti-cancer activity mediated by increased level of acetylation of both histone and non-histone proteins, resulting in growth arrest, cell differentiation and apoptosis. In the present example, the broader anti-tumor activity of Compound A was investigated with a panel of 65 human tumor cell lines derived from the major cancer types to define additional oncology indications for potential clinical development and to identify potential biomarkers of tumor sensitivity and drug resistance.

Among the tumor types examined, a number of lymphoma and leukemia cell lines have shown substantial sensitivity to Compound A treatment. Two gene signatures have been identified for either sensitive or resistant cells, respectively, through the combination of cell viability, underlying genetics, and baseline gene expression data from cell line panels and correlation of $IC_{50}$ values with gene expression levels as reported in the *Cancer Cell Line Encyclopedia* (*CCLE*). These genetic signatures include genes in the ErbB signaling pathway, chromatin remodeling and protein ubiquitination. Biological pathway analysis using the gene signatures indicated an over-representation of certain signaling pathways including the caspase cascade in apoptosis, PDGFR-alpha, S1P3, and ErbB4 signaling. Some of these results support a proposed cytotoxic activity of selective HDAC6 inhibition through blocking of misfolded protein clearance, while other findings suggest further novel pathways that are impacted by the HDAC6 selective inhibitor Compound A.

Confirmation of predicted sensitive and resistant cell lines using the gene signatures will lead to the development of predictive biomarkers and selection of tumor type(s) for further in vitro and in vivo validation with Compound A in combination with approved standard of care therapeutics.

Example 6—Development of a 58 Gene Signature Prediction Model for Breast Cancer 65 cancer cell lines were analyzed using the HDAC inhibitor Compound A. Lymphoma cells were identified as the most sensitive cell group to Compound A. A gene expression profile signature and several gene mutations were demonstrated to be tightly associated with Compound A sensitivity, and can be used as biomarkers to predict a cancer's sensitivity to the HDAC inhibitor Compound A.

Among the cancer cell groups that were studied, the breast cancer cell group comprised of 16 breast cancer cell lines was the only one that produced a confident 58 gene signature prediction model using a correlation analysis of their IC50 values and their gene expression data published at the CCLE database (www dot broad institute dot org/ccle/home). None of the other three other groups, lung cancer, AML, and lymphoma, were able to produce a confident model because of either: 1) the data set size, or 2) the narrow range of the IC50 values.

For the 58 genes in the "signature", 35 low expression and 23 high expression genes related to the "sensitive" signature, while 35 high expression and 23 low expression related to the "resistant" signature (see FIG. 1). The names of the 58 genes are: transforming growth factor beta-3 (TGFB3); CD44 molecule (Indian blood group) (CD44); cytochrome p450, family 4, subfamily Z, polypeptide 2 pseudogene (CYP4Z2P); interferon-induced protein 44 (IFI44); solute carrier family 9, subfamily A (NHE6, cation proton antiporter 6), member 6 (SLC9A6); v-erb-b2 erythroblastic leukemia viral oncogene homolog 2, neuro/glioblastoma derived oncogene homolog (avian) (ERBB2); v-yes-1 Yamaguchi sarcoma viral related oncogene homolog (LYN); pleckstrin homology-like domain, family A, member 1 (PHLDA1); peroxisome proliferator-activated receptor gamma (PPARG); dicarbonyl/L-xylulose reductase (DCXR); uridine phosphorylase 1 (UPP1); ATP-binding cassette, subfamily C (CFTR/MRP), member 11 (ABCC11); aldo-keto reductase family 1, member C2 (dihydrodiol dehydrogenase 2; bile acid binding protein; 3-alpha hydroxysteroid dehydrogenase, type III) (AKR1C2); BCL2-associated athanogene 2 (BAG2); TLR4 interactor with leucine-rich repeats (TRIL); uncharacterized LOC440335 (LOC440335); inhibin, beta B (INHBB); dickkopf 1 homolog (*Xenopus laevis*) (DKK1); insulin receptor substrate 2 (IRS2); chromosome 17 open reading frame 28 (C17orf28); LIM domain kinase 2 (LIMK2); like-glycosyltransferase (LARGE); coiled-coil domain containing 82 (CCDC82); solute carrier family 40 (iron-regulated transporter), member 1 (SLC40A1); interferon-induced protein with tetratricopeptide repeats 1 (IFIT1); formin-like 2 (FMNL2); leukemia inhibitory factor (LIF); transforming growth factor, beta recetor 2 (70/80 kDa) (TGFBR2); G protein-coupled receptor 160 (GPR160); cytokine inducible SH2-containing protein (CISH); phospholipase C, beta 4 (PLCB4); B-cell linker (BLNK); phospholipase C, gamma 2 (phosphatidylinositol-specific) (PLCG2); caveolin 2 (CAV2); proline dehydrogenase (oxidase) 1 (PRODH); ras homolog family member B (RHOB); interferon-induced protein with tetratricopeptide repeats 3 (IFIT3); calbindin 2 (CALB2); TSPY-like 5 (TSPYL5); chromosome X open reading frame 61 (CXorf61); hematopoietically expressed homeobox (HHEX); cAMP responsive element binding protein 3-like4 (CREB3L4); X-box binding protein 1 (XBP1); SAM pointed domain containing ets trsanscription factor (SPDEF); nuclear receptor coactivator 7 (NCOA7); galanin prepropeptide (GAL); HECT and RLD domain containing E3 ubiquitin protein ligase 5 (HERC5); major histocompatibility complex, class I, A (HLA-A); centromere protein V (CENPV); frequently rearranged in advanced T-cell lymphomas 2 (FRAT2); phospholipase B domain containing 1 (PLBD1); adenosine A2b receptor (ADORA2B); G protein-coupled receptor, family C, group 5, member A (GPRC5A); enoyl CoA hydratase domain containing 1 (ECHDC1); guanylate binding protein 1, interferon-inducible (GBP1); sulfatase 2 (SULF2), uncharacterized LOC100507463 (LOC100507463), and KIAA1324 (KIAA1324).

Of the 58 genes above, the following high expression genes are related to the "sensitive" signature: TGFB3, CYP4Z2P, ERBB2, DCXR, ABCC11, TRIL, LOC440335, INHBB, C17orf28, LIMK2, LARGE, SLC40A1, GPR160, CISH, PLCB4, BLNK, PRODH, RHOB, CREB3L4, XBP1, SPDEF, FRAT2, and KIAA1324; and the following low expression genes are related to the "sensitive" signature: CD44, IFI44, SLC9A6, LYN, PHLDA1, PPARG, UPP1, AKR1C2, BAG2, DKK1, IRS2, IFIT1, FMNL2, LIF, TGFBR2, PLCG2, CAV2, IFIT3, CALB2, TSPYL5, CXorf61, HHEX, NCOA7, GAL, HERC5, HLA-A, CENPV, PLBD1, ADORA2B, GPRC5A, ECHDC1, GBP1, SULF2, and LOC100507463.

Of the 58 genes above, the following low expression genes are related to the "resistant" signature: TGFB3, CYP4Z2P, ERBB2, DCXR, ABCC11, TRIL, LOC440335, INHBB, C17orf28, LIMK2, LARGE, SLC40A1, GPR160, CISH, PLCB4, BLNK, PRODH, RHOB, CREB3L4, XBP1, SPDEF, FRAT2, and KIAA1324; and the following high expression genes are related to the "resistant" signature: CD44, IFI44, SLC9A6, LYN, PHLDA1, PPARG, UPP1, AKR1C2, BAG2, DKK1, IRS2, IFIT1, FMNL2, LIF, TGFBR2, PLCG2, CAV2, IFIT3, CALB2, TSPYL5, CXorf61, HHEX, NCOA7, GAL, HERC5, HLA-A, CENPV, PLBD1, ADORA2B, GPRC5A, ECHDC1, GBP1, SULF2, and LOC100507463.

Figure 2:
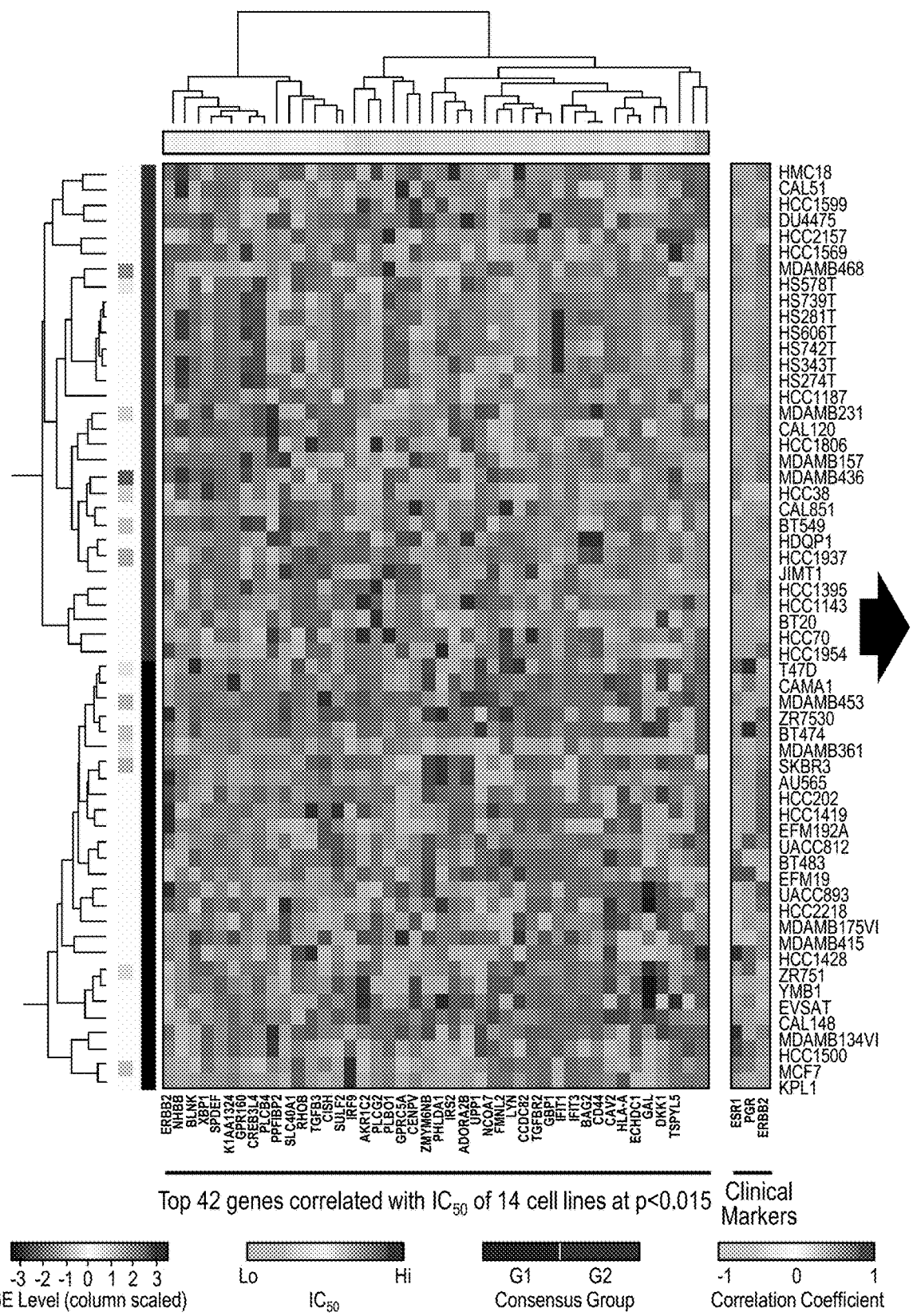
FIGS. 2 (A and B) are pictures of heatmaps showing a correlation between Compound A breast cancer sensitivity biomarkers from 59 cell lines (A) to 352 breast tumors (B).
Figure 2:
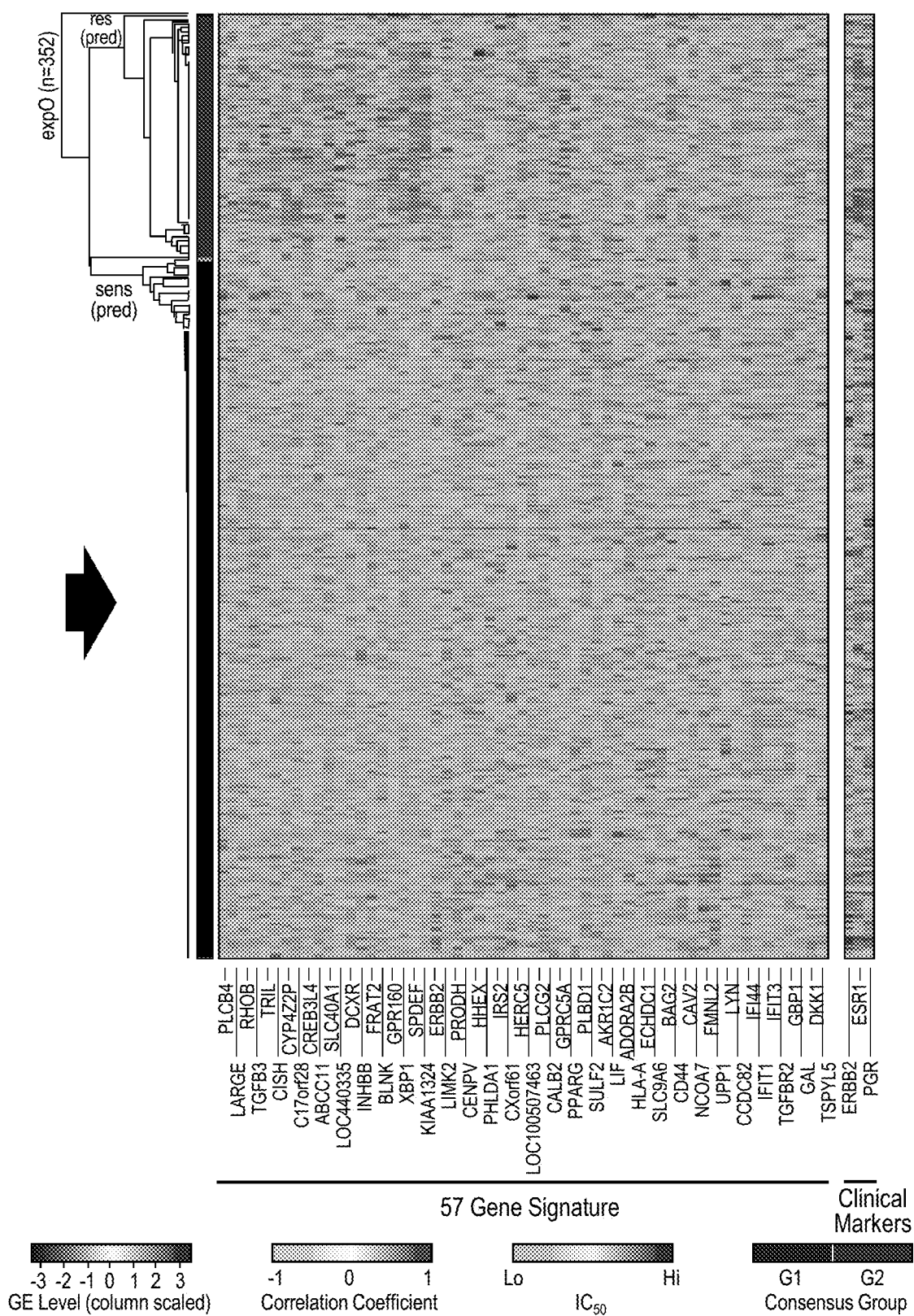

Compound A sensitivity of 59 breast cell lines was predicted based upon their gene expression profile data published at the CCLE site using the 58 gene signature (see FIG. 2). Two statistically well-supported groups were identified. The first group (32 cell lines) was associated with sensitive cells, which were defined as having an IC50<5 µM. The second group (27 cell lines) was associated with resistant cells, which were defined as having an IC50>5 µM. In order to validate the Compound A sensitivity prediction power of the model, tested 4 new breast cancer cell lines were tested, and their IC50 values fit well to the established model.

Figure 3:
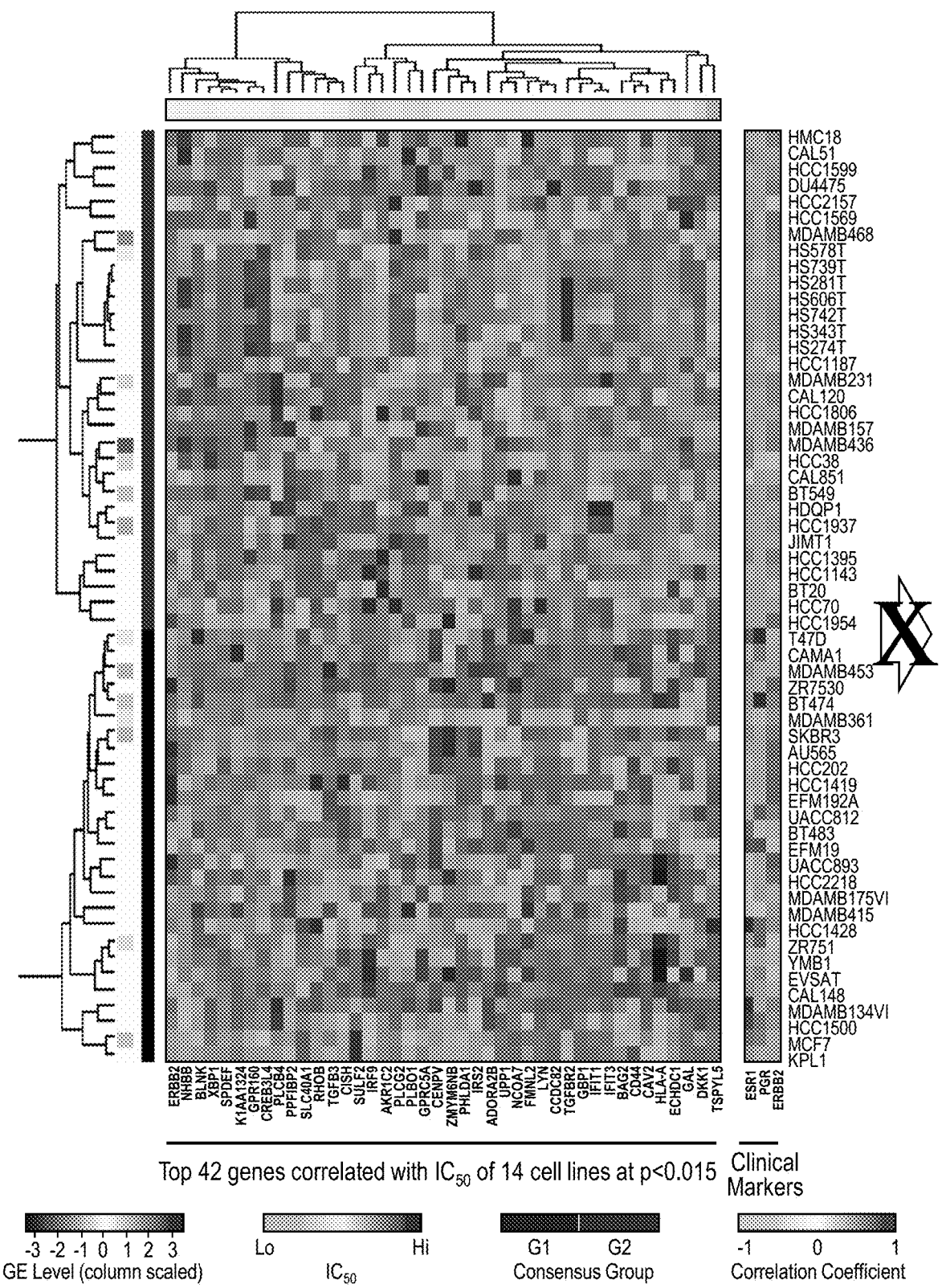
FIGS. 3 (A and B) are pictures of heatmaps showing a lack of a correlation between Compound A breast cancer sensitivity biomarkers from 59 cell lines (A) to 293 colon tumors (B).
Figure 3:
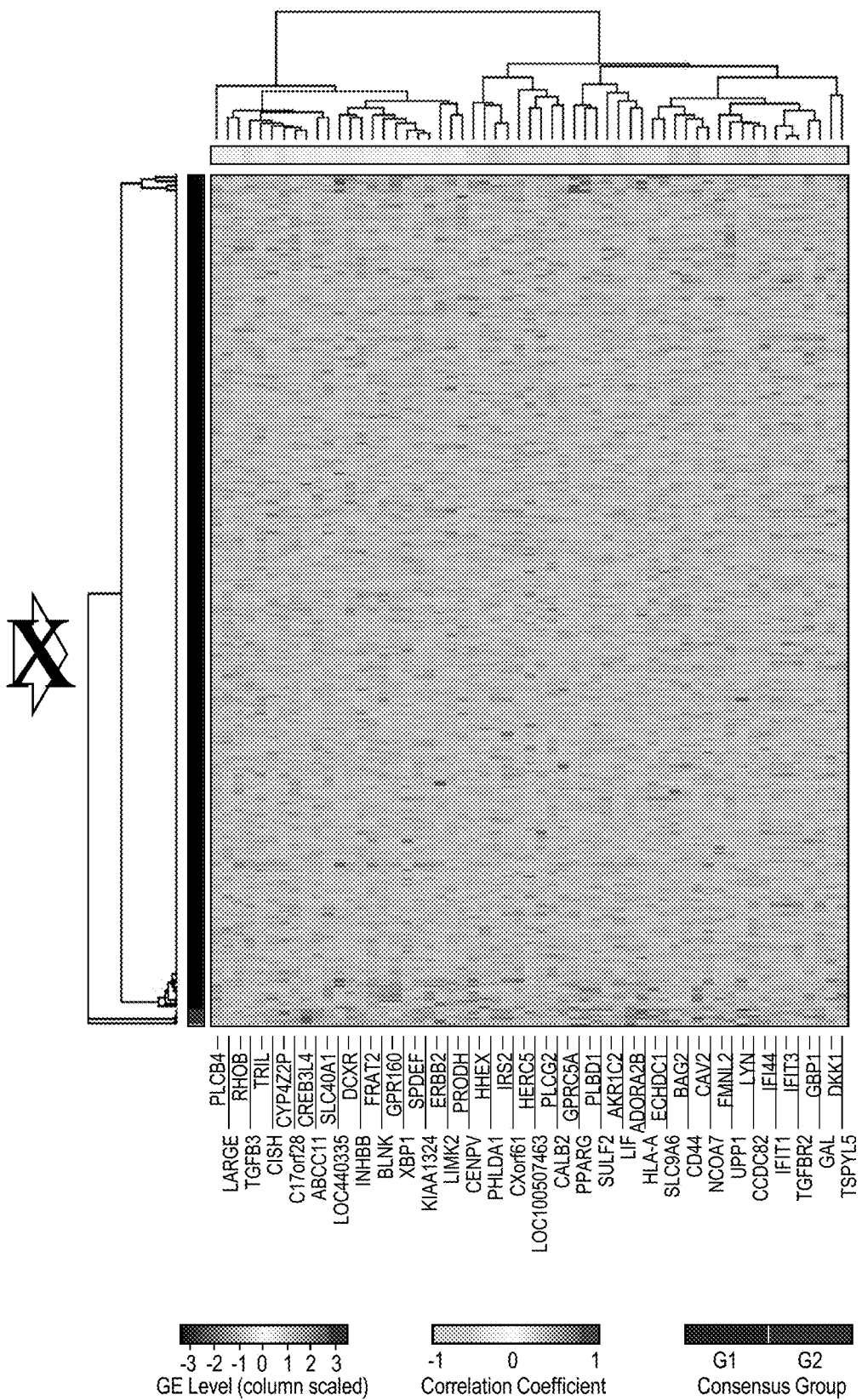

The same procedure above was applied to 352 primary breast tumor tissues in the expO database (www dot intgen dot org/expo/). The sensitivity of these primary cells to Compound A was predicted by testing the correlation of their gene expression with the gene expression of the two CCLE groups (sensitive and resistant) (see FIG. 2). Two stable consensus groups were identified within the tested breast tumors (260 predicted sensitive tissues, 90 predicted resistant tissues, with 2 unclassified). One stable consensus group (260 predicted sensitive tissues) was found to be similar to the sensitive CCLE breast cancer cell group, and the other stable consensus group (90 predicted resistant tissues) was found to be similar to the resistant CCLE breast cancer cell group. No significantly distinct groups were identified within either lung or colon tumor tissues (see FIG. 3).

Figure 4:
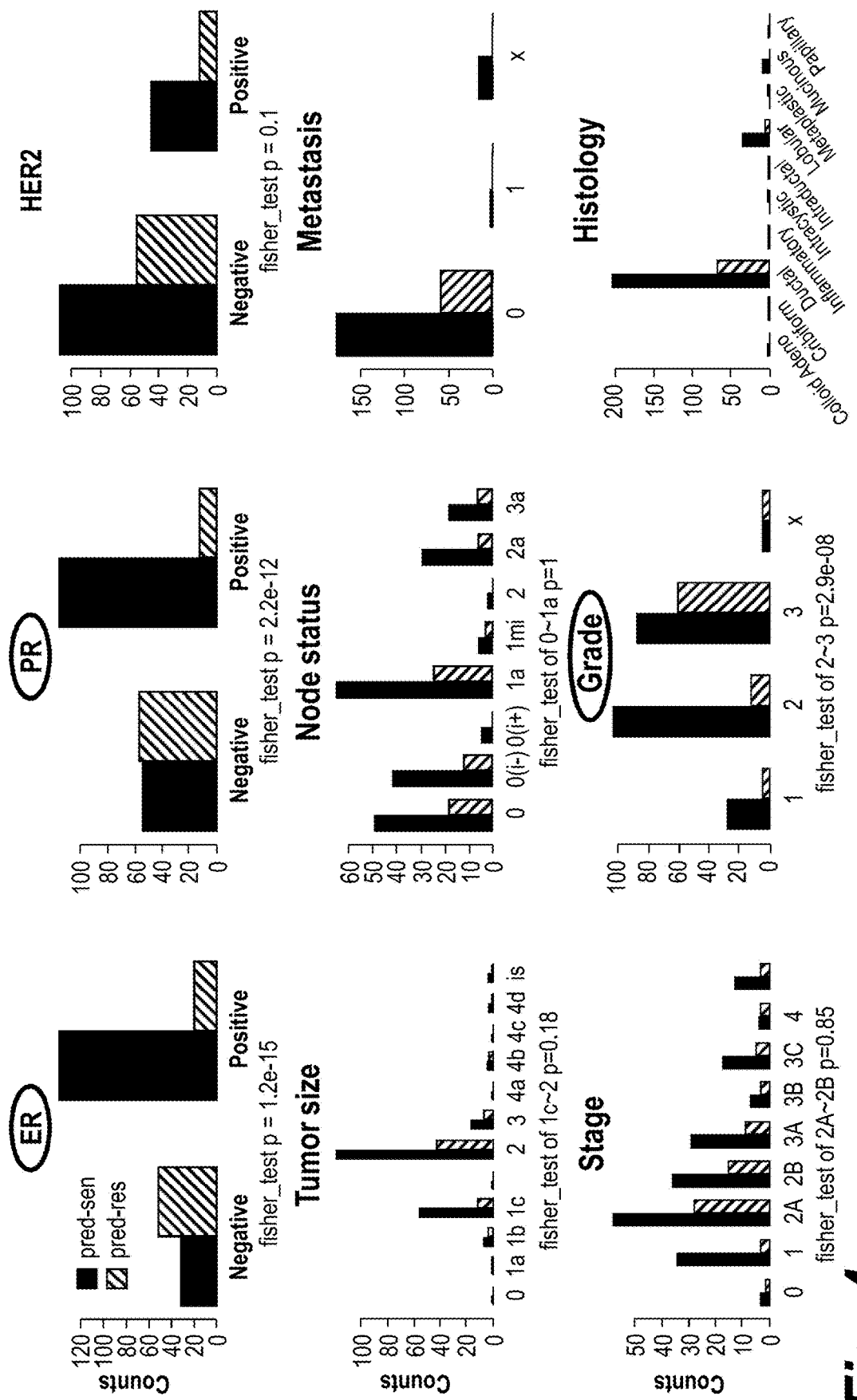
FIGS. 4 (A, B, C, D, E, F, G, H, and I) shows graphs of clinical markers for Compound A breast cancer sensitivity biomarkers. ER means estrogen receptor; PR means progesterone receptor; HER2 means human epidermal growth factor receptor 2, which is also known as Neu, ErbB-2, CD340, or p185.

The sensitive group of breast tumor tissues was enriched for three clinical breast cancer diagnosis markers: ER positive, PR positive, and low grade breast tumors. The resistant group of breast tumor tissues was associated with a triple negative (ER—PR-Her2/neu-) marker. See FIG. 4.

In conclusion, a stable gene expression signature was identified that could predict Compound A sensitivity in breast cancer.

Example 7: Summary of the 16 Breast Cancer Cell Line IC50 Data

Table 1 shows a summary of the 16 breast cancer cell line IC50 data, which were used to model the predictive gene expression biomarkers (Note: Only 14 of these 16 were found in the CCLE data and used in the modeling).

Among many genetic markers of these cells, the ERBB2 (gene for Her2) amplification genotype was tightly associated with Compound A sensitivity phenotype (Table 1). Actually, ERBB2 is one of the 58 genes in the model itself. Although ESR1 (gene for ER) and PSR (gene for PR) were not picked in the top 58 gene list during the cell line data analysis, however, when using this 58-gene signature to analyze the 352 clinical breast tumor data in expO data, both ER+ and PR+ were significantly associated with the "predicted sensitive" group.

TABLE 1

| Cells | ERBB2 | Compound A IC$_{50}$ (µM) |
|---|---|---|
| MDA-MB-453 | Amplified | 1.25 |
| SK-BR-3 | Amplified | 1.94 |
| BT 474 | Amplified | 2.32 |
| ZR-75-1 | | 3.57 |
| MDA-MB-361 | Amplified | 4.51 |
| T-47D* | | 5.00 |
| Hs578T | | 5.57 |
| MX-1 | | 6.38 |
| MDA-MB-231 | | 7.49 |
| Bcap-37 | | 7.66 |
| HCC38 | | 7.76 |
| MCF-7 | | 8.95 |
| BT-549 | | 8.97 |
| HCC1937 | | 11.25 |
| MDA-MB-468 | | 14.92 |
| MDA-MB-436 | | 25.66 |

Example 8: Synthesis of 2-(diphenylamino)-N-(7-(hydroxyamino)-7-oxoheptyl)pyrimidine-5-carboxamide (Compound A)

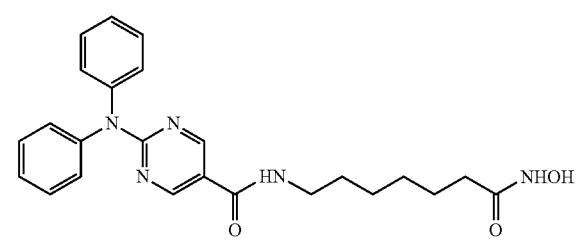

Reaction Scheme

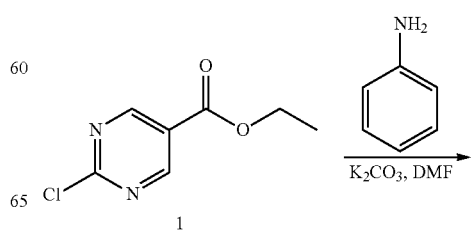

-continued

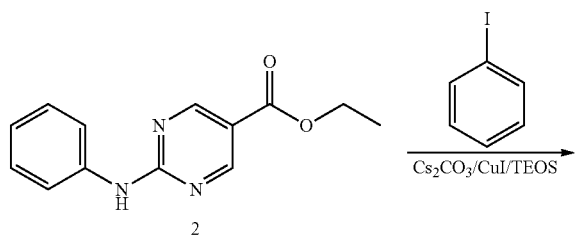

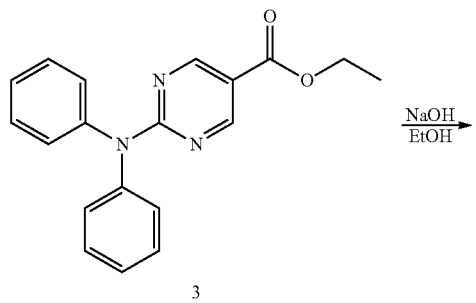

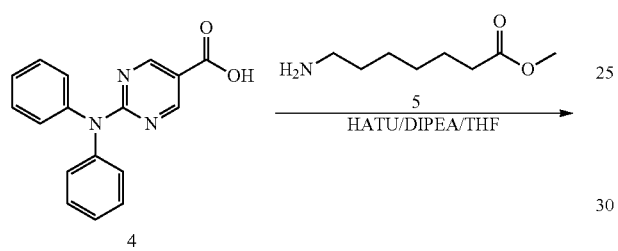

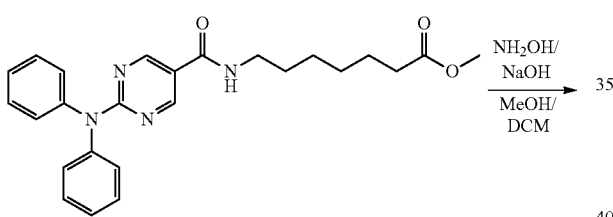

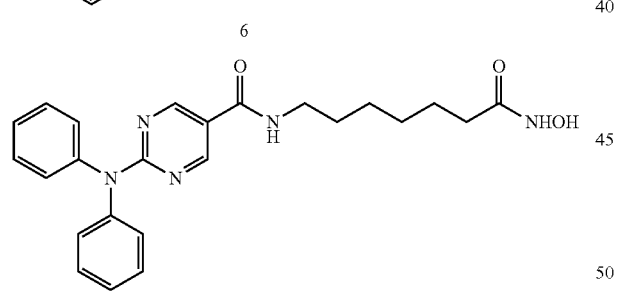

Synthesis of Intermediate 2

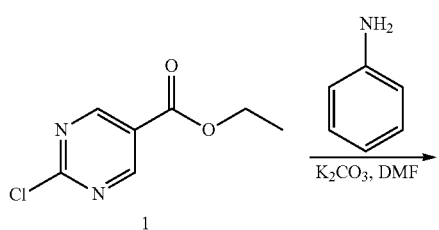

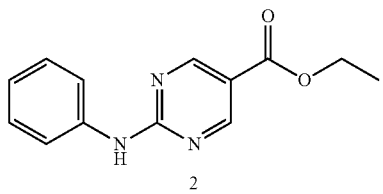

A mixture of aniline (3.7 g, 40 mmol), ethyl 2-chloropyrimidine-5-carboxylate 1 (7.5 g, 40 mmol), K₂CO₃ (11 g, 80 mmol) in DMF (100 ml) was degassed and stirred at 120° C. under N₂ overnight. The reaction mixture was cooled to rt and diluted with EtOAc (200 ml), then washed with saturated brine (200 ml×3). The organic layer was separated and dried over Na₂SO₄, evaporated to dryness and purified by silica gel chromatography (petroleum ethers/EtOAc=10/1) to give the desired product as a white solid (6.2 g, 64%).

Synthesis of Intermediate 3

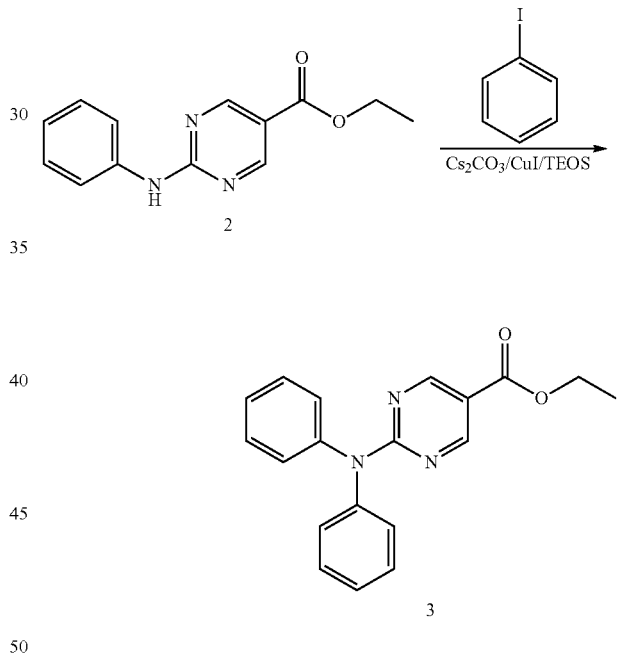

A mixture of the compound 2 (6.2 g, 25 mmol), iodobenzene (6.12 g, 30 mmol), CuI (955 mg, 5.0 mmol), Cs₂CO₃ (16.3 g, 50 mmol) in TEOS (200 ml) was degassed and purged with nitrogen. The resulting mixture was stirred at 140° C. for 14 h. After cooling to rt, the residue was diluted with EtOAc (200 ml) and 95% EtOH (200 ml), NH₄F—H₂O on silica gel [50 g, pre-prepared by the addition of NH₄F (100 g) in water (1500 ml) to silica gel (500 g, 100-200mesh)] was added, and the resulting mixture was kept at rt for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

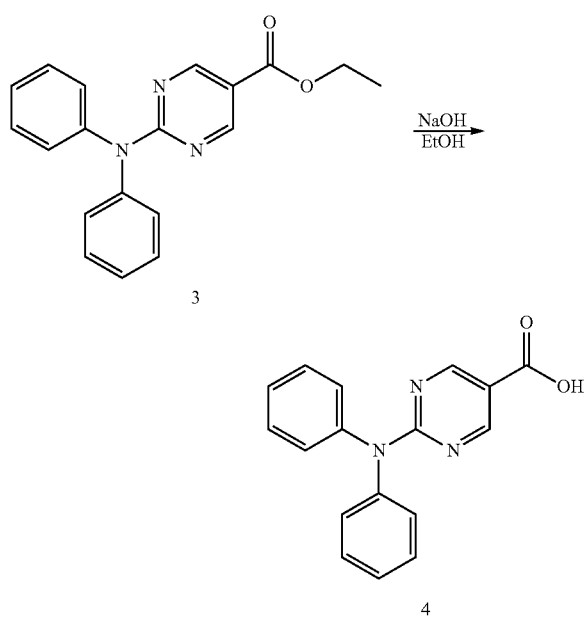

2N NaOH (200 ml) was added to a solution of the compound 3 (3.0 g, 9.4 mmol) in EtOH (200 ml). The mixture was stirred at 60° C. for 30 min After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 6

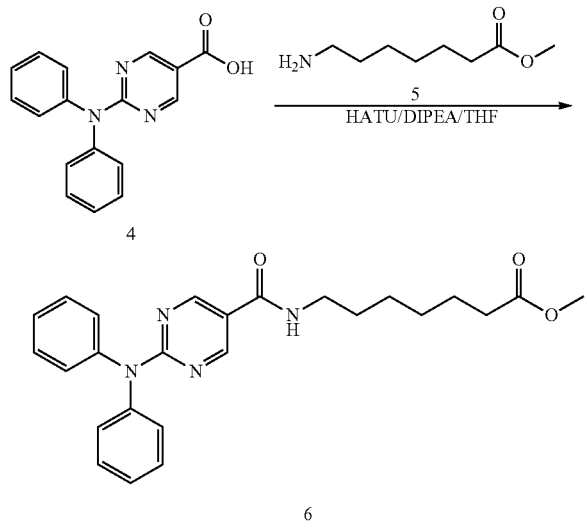

A mixture of compound 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at rt overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide

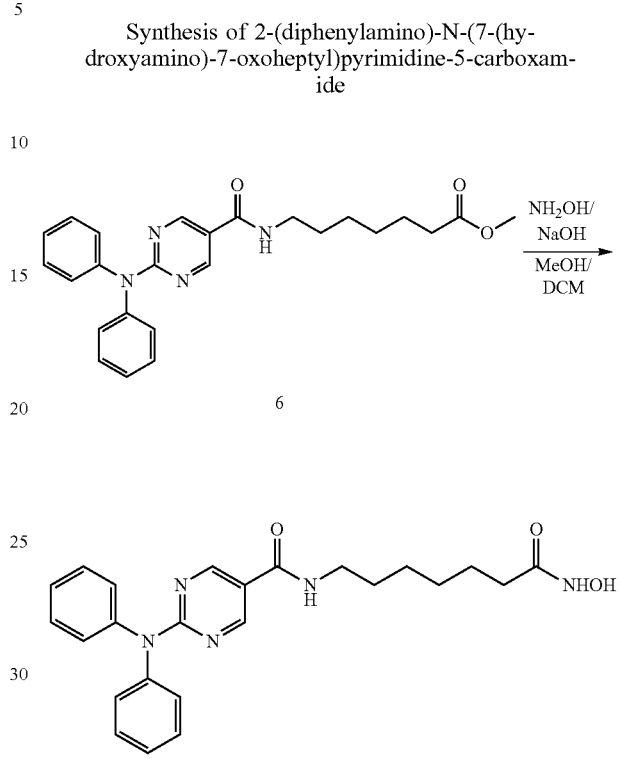

A mixture of the compound 6 (2.0 g, 4.6 mmol), sodium hydroxide (2N, 20 mL) in MeOH (50 ml) and DCM (25 ml) was stirred at 0° C. for 10 min Hydroxylamine (50%) (10 ml) was cooled to 0° C. and added to the mixture. The resulting mixture was stirred at rt for 20 min After removal of the solvent, the mixture was neutralized with 1M HCl to give a white precipitate. The crude product was filtered and purified by pre-HPLC to give a white solid (950 mg, 48%).

What is claimed is:

1. A method for predicting whether a cancer patient will respond to combination treatment with a histone deacetylase-6 (HDAC6) inhibitor and a proteasome inhibitor comprising the steps of:
   a) measuring the expression level of a gene selected from the group consisting of UDP-glucose dehydrogenase (UGDH); H2A histone family, member Y2 (H2AFY2); myosin VC (MYO5C); nephronectin (NPNT); KIAA1598 (KIAA1598); serglycin (SRGN); collagen, type VI, alpha 3 (COL6A3); G-protein signaling modulator 3 (GPSM3); hydroxysteroid dehydrogenase 1 (HSD11B1); peroxisomal biogenesis factor 6 (PEX6); ras-related C3 botulinum toxin substrate 2 (RAC2); synovial sarcoma, X breakpoint 5 (SSX5); and acyl-Coenzyme A binding domain containing 3 (ACBD3); in a biological sample from the cancer patient; and
   b) correlating a low expression level, as compared to a normalized gene expression level of the gene, of any one or more of the genes UGDH, H2AFY2, MYO5C, NPNT, and KIAA1598 as an indication that the patient will respond to such treatment; or correlating a high expression level of the gene, as compared to a normalized gene expression level, of any one or more of the genes SRGN, COL6A3, GPSM3, HSD11B1, PEX6, RAC2, SSX5, and ACBD3 as an indication that the patient will respond to such treatment; and c) administering to the patient a therapeutically effective amount of a HDAC6 inhibitor and a proteasome inhibitor.

2. The method of claim 1, wherein the cancer is selected from the group consisting of: brain/neuronal cancer, breast cancer, cancer of the central nervous system, haematopoietic and lymphoid tissue cancer, kidney cancer, cancer of the large intestine, liver cancer, lung cancer, cancer of the oesophagus, pancreatic cancer, prostate cancer, skin cancer, soft tissue cancer, and stomach cancer.

3. The method of claim 1, wherein the HDAC6 inhibitor is a compound of formula I:

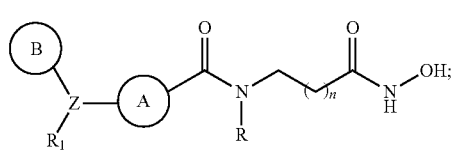

or a pharmaceutically acceptable salt, ester or prodrug thereof.

4. The method of claim 3, wherein the compound of formula I is

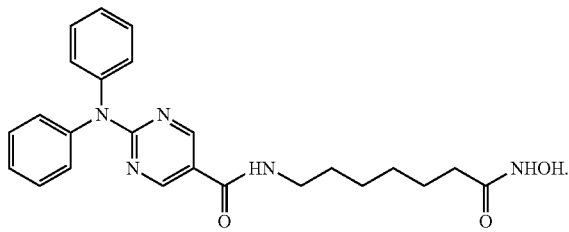

5. The method of claim 1, wherein the proteasome inhibitor is bortezomib.

6. The method of claim 1, wherein the biological sample is a biopsy sample.

7. The method of claim 3, wherein the compound of formula I is

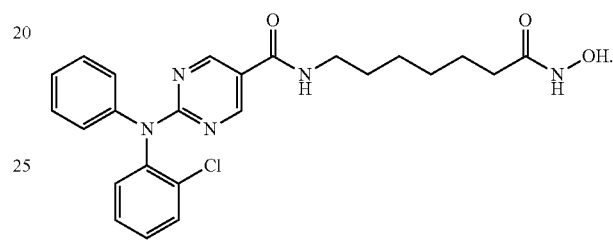

* * * * *